(12) United States Patent
Lamberth et al.

(10) Patent No.: US 11,629,129 B2
(45) Date of Patent: Apr. 18, 2023

(54) MICROBIOCIDAL PICOLINAMIDE DERIVATIVES

(71) Applicant: SYNGENTA PARTICIPATIONS AG, Basel (CH)

(72) Inventors: Clemens Lamberth, Stein (CH); Stefano Rendine, Stein (CH); Mattia Riccardo Monaco, Stein (CH); David Burns, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 198 days.

(21) Appl. No.: 17/058,361

(22) PCT Filed: May 20, 2019

(86) PCT No.: PCT/EP2019/062995
§ 371 (c)(1),
(2) Date: Nov. 24, 2020

(87) PCT Pub. No.: WO2019/224160
PCT Pub. Date: Nov. 28, 2019

(65) Prior Publication Data
US 2021/0114984 A1    Apr. 22, 2021

(30) Foreign Application Priority Data
May 25, 2018 (EP) .................................. 18174406

(51) Int. Cl.
*C07D 213/81* (2006.01)
*A01N 43/40* (2006.01)
*C07D 401/12* (2006.01)
*C07D 409/12* (2006.01)

(52) U.S. Cl.
CPC ........... *C07D 213/81* (2013.01); *A01N 43/40* (2013.01); *C07D 401/12* (2013.01); *C07D 409/12* (2013.01)

(58) Field of Classification Search
CPC .............. C07D 213/81; C07D 401/12; C07D 409/12; A01N 43/40
See application file for complete search history.

(56) References Cited

U.S. PATENT DOCUMENTS 11,395,489 B2 *   7/2022   Rendine ................. A01N 43/40

FOREIGN PATENT DOCUMENTS

| CN | 103539731 A * | 1/2014 | ........... C07D 213/81 |
| WO | 2000076979 A1 | 12/2000 | |
| WO | WO-0076979 A1 * | 12/2000 | ............. A01N 43/40 |
| WO | 2016109288 A1 | 7/2016 | |
| WO | 2016109300 A1 | 7/2016 | |
| WO | 2016122802 A1 | 8/2016 | |
| WO | WO-2021146522 A1 * | 7/2021 | ........... C07D 213/69 |

OTHER PUBLICATIONS

European Search report for European Patent Application No. 18174406.1 dated Jul. 9, 2018.
Written Opinion of the International Authority and International Search Report for International Patent Application No. PCT/EP2019/062995 dated Jul. 1, 2019.

* cited by examiner

*Primary Examiner* — Amanda L. Aguirre
(74) *Attorney, Agent, or Firm* — BakerHostetler; Toni-Junell Herbert

(57) ABSTRACT

Compounds of the formula (I), wherein the substituents are as defined in claim 1, useful as pesticides, and especially fungicides.

15 Claims, No Drawings

MICROBIOCIDAL PICOLINAMIDE DERIVATIVES

CROSS-REFERENCE TO RELATED APPLICATIONS

This application is a 371 National Stage application of International Application No. PCT/EP2019/062995 filed May 20, 2019 which claims priority to EP 18174406.1, filed May 25, 2018.

The present invention relates to microbiocidal picolinamide derivatives, e.g., as active ingredients, which have microbiocidal activity, in particular fungicidal activity. The invention also relates to the preparation of these picolinamide derivatives, to agrochemical compositions which comprise at least one of the picolinamide derivatives and to uses of the picolinamide derivatives or compositions thereof in agriculture or horticulture for controlling or preventing the infestation of plants, harvested food crops, seeds or non-living materials by phytopathogenic microorganisms, preferably fungi.

Picolinamide compounds as fungicidal agents are described in WO 2016/109288, WO 2016/109289, WO 2016/109300, WO 2016/109301, WO 2016/109302 and WO 2016/109303.

According to the present invention, there is provided a compound of formula (I):

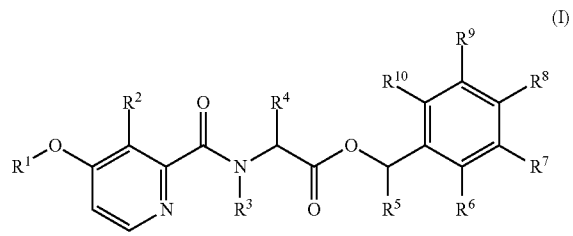

wherein, $R^1$ is $C_1$-$C_6$alkyl or $C_1$-$C_6$haloalkyl;

$R^2$ is hydroxy, $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy or $C_2$-$C_6$acyloxy$C_1$-$C_6$haloalkoxy;

$R^3$ is hydrogen, $C_1$-$C_6$alkoxy or $C_3$-$C_6$cycloalkyl;

$R^4$ and $R^5$ are each independently $C_1$-$C_6$alkyl, $C_3$-$C_6$cycloalkyl or $C_1$-$C_6$haloalkyl;

$R^6$, $R^9$ and $R^{10}$ are each independently hydrogen, halogen or $C_1$-$C_6$alkyl;

$R^7$ and $R^8$ are each independently hydrogen, aryl, heteroaryl, aryl$C_1$-$C_3$alkyl, heteroaryl$C_1$-$C_3$alkyl, aryloxy or heteroaryloxy, wherein the heteroaryl moiety is a 5- or 6-membered aromatic ring which comprises 1, 2, 3 or 4 heteroatoms individually selected from N, O and S, and wherein the aryl and heteroaryl moieties are each optionally substituted by 1, 2 or 3 substituents, which may be the same or different, selected from $R^{11}$:

$R^{11}$ is halogen, cyano, $C_1$-$C_6$alkyl, $C_3$-$C_6$cycloalkyl, $C_1$-$C_6$haloalkyl, $C_1$-$C_6$alkoxy, $C_1$-$C_6$alkoxy$C_1$-$C_6$alkyl, $C_1$-$C_4$haloalkoxy, or $C_1$-$C_6$alkylcarbonyl;

or a salt or an N-oxide thereof.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I) according to the present invention. Such an agricultural composition may further comprise at least one additional active ingredient and/or an agrochemically-acceptable diluent or carrier.

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may exclude methods for the treatment of the human or animal body by surgery or therapy.

Where substituents are indicated as being "optionally substituted", this means that they may or may not carry one or more identical or different substituents, e.g., one, two or three $R^{11}$ substituents. For example, $C_1$-$C_6$alkyl substituted by 1, 2 or 3 halogens, may include, but not be limited to, —$CH_2Cl$, —$CHCl_2$, —$CCl_3$, —$CH_2F$, —$CHF_2$, —$CF_3$, —$CH_2CF_3$ or —$CF_2CH_3$ groups. As another example, $C_1$-$C_6$alkoxy substituted by 1, 2 or 3 halogens, may include, but not be limited to, $CH_2ClO$—, $CHCl_2O$—, $CCl_3O$—, $CH_2FO$—, $CHF_2$—, $CF_3O$—, $CF_3CH_2O$— or $CH_3CF_2O$— groups.

As used herein, the term "hydroxyl" or "hydroxy" means a —OH group.

As used herein, the term "cyano" means a —CN group.

As used herein, =O means an oxo group, e.g., as found in a carbonyl (—C(=O)—) group.

As used herein, the term "halogen" refers to fluorine (fluoro), chlorine (chloro), bromine (bromo) or iodine (iodo).

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_1$-$C_4$alkyl" is to be construed accordingly. Examples of $C_1$-$C_6$alkyl include, but are not limited to, methyl, ethyl, n-propyl, n-butyl, n-pentyl, n-hexyl and the isomers thereof, for example, iso-propyl, iso-butyl, sec-butyl, tert-butyl or iso-amyl. A "$C_1$-$C_6$alkylene" group refers to the corresponding definition of $C_1$-$C_6$alkyl, except that such radical is attached to the rest of the molecule by two single bonds. The term "$C_1$-$C_2$alkylene" is to be construed accordingly. Examples of $C_1$-$C_6$alkylene, include, but are not limited to, —$CH_2$—, —$CH_2CH_2$— and —$(CH_2)_3$—.

As used herein, the term "$C_3$-$C_8$cycloalkyl" refers to a radical which is a monocyclic saturated ring system and which contains 3 to 8 carbon atoms. The term "$C_3$-$C_6$cycloalkyl" is to be construed accordingly. Examples of $C_3$-$C_6$cycloalkyl include, but are not limited to, cyclopropyl, 1-methylcyclopropyl, 2-methylcyclopropyl, cyclobutyl, cyclopentyl, cyclohexyl, cycloheptyl and cyclooctyl.

As used herein, the term "$C_1$-$C_6$haloalkyl" refers to $C_1$-$C_6$alkyl radical as generally defined above substituted by one or more of the same or different halogen atoms. The terms "$C_1$-$C_4$haloalkyl" and "$C_1$-$C_2$haloalkyl" are to be construed accordingly. Examples of $C_1$-$C_6$haloalkyl include, but are not limited to fluoromethyl, fluoroethyl, difluoromethyl, trifluoromethyl, and 2,2,2-trifluoroethyl.

As used herein, the term "$C_1$-$C_6$alkoxy" refers to a radical of the formula —$OR_a$ where $R_a$ is a $C_1$-$C_6$alkyl radical as generally defined above. The term "$C_1$-$C_4$alkoxy" is to be construed accordingly. Examples of $C_1$-$C_6$alkoxy include, but are not limited to, methoxy, ethoxy, 1-methylethoxy (iso-propoxy), propoxy, butoxy, 1-methylpropoxy, and 2-methylpropoxy.

As used herein, the term "$C_1$-$C_6$alkoxy$C_1$-$C_6$alkyl" refers to a radical of the formula $R_b$O—$R_a$— where $R_b$ is a $C_1$-$C_6$alkyl radical as generally defined above, and $R_a$ is a $C_1$-$C_6$alkylene radical as generally defined above. Examples of "$C_1$-$C_6$alkoxy$C_1$-$C_6$alkyl" include, but are not limited to methoxymethyl, ethoxymethyl and methoxyethyl.

As used herein, the term "$C_1$-$C_6$alkoxy$C_1$-$C_6$alkoxy" refers to a radical of the formula $R_a$O—$R_b$O— where $R_a$ is a $C_1$-$C_6$alkyl radical as generally defined above, and $R_b$ is a $C_1$-$C_6$alkylene radical as generally defined above. Examples of $C_1$-$C_6$alkoxy$C_1$-$C_6$alkoxy include, but are not limited to, methoxymethoxy, ethoxymethoxy and methoxyethoxy.

As used herein, the term "$C_1$-$C_6$haloalkoxy$C_1$-$C_6$alkoxy" refers to a radical of the formula $R_a$O—$R_b$O—, where $R_a$ is a $C_1$-$C_6$alkyl radical as generally defined above substituted by one or more of the same or different halogen atoms, and $R_b$ is a $C_1$-$C_6$alkylene radical as generally defined above. Examples of $C_1$-$C_6$haloalkoxy$C_1$-$C_6$alkoxy groups include, but not limited to trifluoromethoxymethoxy.

As used herein, the term "$C_1$-$C_6$alkoxy$C_1$-$C_6$haloalkoxy" refers to a radical of the formula $R_a$O—$R_b$O—, where $R_a$ is a $C_1$-$C_6$alkyl radical as generally defined above and $R_b$ is a $C_1$-$C_6$alkylene radical as generally defined above substituted by one or more of the same or different halogen atoms. Examples of $C_1$-$C_6$alkoxy$C_1$-$C_6$haloalkoxy groups include, but not limited to methoxydifluoromethoxy.

As used herein, the term "$C_2$-$C_6$acyl" refers to a radical $R_a$C(=O)—, where $R_a$ is a $C_1$-$C_6$alkyl as generally defined above. Acyl groups include, but are not limited to, acetyl and propanoyl.

As used herein, the term "$C_2$-$C_6$acyloxy" refers to a radical of the formula —$OR_a$ where $R_a$ is a $C_2$-$C_6$acyl radical as generally defined above. $C_2$-$C_6$acyloxy groups include, but are not limited to, acetoxy, propanoyloxy, isopropanoyloxy, and butanoyloxy.

As used herein, the term "$C_2$-$C_6$haloacyloxy" refers to a radical of the formula $R_a$C(=O)O—, where $R_a$ is $C_1$-$C_5$alkyl radical as generally defined above substituted by one or more of the same or different halogen atoms. $C_2$-$C_6$haloacyloxy groups include, but are not limited to trifluoroacetoxy.

As used herein, the term "$C_2$-$C_6$acyloxy$C_1$-$C_6$alkoxy" refers to a radical of the formula $R_a$C(=O)O$R_b$O— where $R_a$ is a $C_1$-$C_5$alkyl radical as generally defined above and where $R_b$ is a $C_1$-$C_6$alkylene radical as generally defined above.

As used herein, the term "$C_2$-$C_6$haloacyloxy$C_1$-$C_6$alkoxy" refers to a radical of the formula $R_a$C(=O)O$R_b$O— where $R_a$ is a $C_1$-$C_5$alkyl radical as generally defined above substituted by one or more of the same or different halogen atoms, and $R_b$ is a $C_1$-$C_6$alkylene radical as generally defined above.

As used herein, the term "$C_2$-$C_6$acyloxy$C_1$-$C_6$haloalkoxy" refers to a radical of the formula $R_a$C(=O)O$R_b$O— where $R_a$ is a $C_1$-$C_5$alkyl radical as generally defined above, and $R_b$ is a $C_1$-$C_6$alkylene radical as generally defined above substituted by one or more of the same or different halogen atoms.

As used herein, the term "$C_1$-$C_6$alkylcarbonyl" refers to a radical of the formula —C(O)$R_a$ where $R_a$ is a $C_1$-$C_6$alkyl radical as generally defined above. The term "$C_1$-$C_4$alkylcarbonyl" is to be construed accordingly. Examples of $C_1$-$C_6$alkylcarbonyl include, but are not limited to, methylcarbonyl, ethylcarbonyl, n-propylcarbonyl, n-butylcarbonyl, n-pentylcarbonyl, n-hexylcarbonyl and the isomers thereof, for example, iso-propylcarbonyl, iso-butylcarbonyl, sec-butylcarbonyl, tert-butylcarbonyl or iso-amylcarbonyl.

As used herein, the term "aryl" refers to an aromatic ring system consisting solely of carbon and hydrogen atoms which may be mono-, bi- or tricyclic. Examples of such ring systems include phenyl, naphthalenyl, anthracenyl, indenyl or phenanthrenyl.

As used herein, the term "aryl$C_1$-$C_3$alkyl" refers to an aryl ring attached to the rest of the molecule by a $C_1$-$C_3$alkylene radical as defined above. Examples of aryl$C_1$-$C_3$alkyl include, but are not limited to benzyl.

As used herein, the term "heteroaryl" refers to a 5- or 6-membered aromatic monocyclic ring radical which comprises 1, 2, 3 or 4 heteroatoms individually selected from N, O and S. The heteroaryl radical may be bonded to the rest of the molecule via a carbon atom or heteroatom. Examples of heteroaryl include, but are not limited to, furanyl, benzofuranyl, thienyl, benzothienyl, benzothiazolyl, imidazolyl, benzimidazolyl, oxadiazolyl, pyridyl, pyrrolyl, quinolinyl, isoquinolinyl, indolyl, isoindolyl, indazolyl, pyrazolyl, thiazolyl, oxazolyl, benzoxazolyl, pyridazinyl, cinnolinyl, pyrimidinyl, and quinazolinyl.

As used herein, the term "heteroaryl$C_1$-$C_3$alkyl" refers to a heteroaryl ring attached to the rest of the molecule by a $C_1$-$C_3$alkylene radical as defined above.

As used herein, the term "heteroaryloxy" refers to a radical of the formula —$OR_a$ where $R_a$ is a heteroaryl radical as generally defined above. Examples of heteroaryloxy include, but are not limited to, pyridyloxy and quinolinyloxy.

The presence of one or more possible asymmetric carbon atoms in a compound of formula (I) means that the compounds may occur in optically isomeric forms, i.e., enantiomeric or diastereomeric forms. Also, atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as an N-oxide, or in salt form, e.g., an agronomically usable salt form.

N-oxides are oxidized forms of tertiary amines or oxidized forms of nitrogen-containing heteroaromatic compounds. They are described for instance in the book "Heterocyclic N-oxides" by A. Albini and S. Pietra, CRC Press, Boca Raton (1991).

The following list provides definitions, including preferred definitions, for substituents $R^1$, $R^2$, $R^3$, $R^4$, $R^5$, $R^6$, $R^7$, $R^8$, $R^9$, $R^{10}$ and $R^{11}$, with reference to compounds of formula (I). For any one of these substituents, any of the definitions given below may be combined with any definition of any other substituent given below or elsewhere in this document.

$R^1$ is $C_1$-$C_6$alkyl or $C_1$-$C_6$haloalkyl. Preferably, $R^1$ is $C_1$-$C_6$alkyl or $C_1$-$C_4$haloalkyl, more preferably, $C_1$-$C_4$alkyl or $C_1$-$C_2$haloalkyl, and even more preferably, $C_1$-$C_3$alkyl (including methyl or ethyl), difluoromethyl or trifluoromethyl. Particularly preferably, $R^1$ is methyl or ethyl, and most preferably methyl.

$R^2$ is hydroxy, $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$haloalkoxy or $C_2$-$C_6$acyloxy$C_1$-$C_6$haloalkoxy. Preferably, $R^2$ is hydroxy, $C_2$-$C_4$acyloxy, $C_2$-$C_4$haloacyloxy, $C_1$-$C_4$alkoxy$C_2$-$C_4$alkoxy, $C_1$-$C_4$haloalkoxy$C_1$-$C_4$alkoxy, $C_1$-$C_4$alkoxy$C_1$-$C_4$haloalkoxy, $C_2$-$C_4$acyloxy$C_1$-$C_4$alkoxy, $C_2$-$C_4$haloacyloxy$C_1$-$C_4$alkoxy or $C_2$-$C_4$acyloxy$C_1$-$C_4$haloalkoxy. More preferably, $R^2$ is hydroxy, acetoxy, propanoyloxy, acetoxymethoxy, propanoyloxymethoxy or 2-methyl-propanoyloxymethoxy. More preferably still, $R^2$ is hydroxy, acetoxy or 2-methylpropanoyloxymethoxy, and most preferably, $R^2$ is hydroxy or acetoxy.

$R^3$ is hydrogen, $C_1$-$C_6$alkoxy or $C_3$-$C_8$cycloalkyl. Preferably, $R^3$ is hydrogen, $C_1$-$C_3$alkoxy or $C_3$-$C_6$cycloalkyl. More preferably, $R^3$ is hydrogen, methoxy, or cyclopropyl. Even more preferably, $R^3$ is hydrogen or methoxy, and most preferably, $R^3$ is hydrogen.

$R^4$ and $R^5$ are each independently $C_1$-$C_6$alkyl, $C_3$-$C_6$cycloalkyl or $C_1$-$C_6$haloalkyl. Preferably, $R^4$ and $R^5$ are each independently $C_1$-$C_3$alkyl, $C_3$-$C_6$cycloalkyl or $C_1$-$C_3$haloalkyl. More preferably, $R^4$ and $R^5$ are each independently $C_1$-$C_3$alkyl or $C_1$-$C_3$haloalkyl, even more preferably, methyl, ethyl, isopropyl, trifluoromethyl or difluoromethyl. More preferably still, $R^4$ and $R^5$ are each independently methyl, ethyl or trifluoromethyl. Most preferably, $R^4$ and $R^5$ are both methyl.

$R^6$, $R^9$ and $R^{10}$ are each independently hydrogen, halogen or $C_1$-$C_6$alkyl. Preferably, $R^6$, $R^9$ and $R^{10}$ are each independently hydrogen, halogen or $C_1$-$C_4$alkyl. More preferably, $R^6$, $R^9$ and $R^{10}$ are each independently hydrogen, fluoro, chloro or methyl, even more preferably hydrogen or fluoro, and most preferably, $R^6$, $R^9$ and $R^{10}$ are all hydrogen.

$R^7$ and $R^8$ are each independently hydrogen, aryl, heteroaryl, aryl$C_1$-$C_3$alkyl, heteroaryl$C_1$-$C_3$alkyl, aryloxy or heteroaryloxy, wherein the heteroaryl moiety is a 5- or 6-membered aromatic ring which comprises 1, 2, 3 or 4 heteroatoms individually selected from N, O and S, and wherein the aryl and heteroaryl moieties are each optionally substituted by 1, 2 or 3 substituents, which may be the same or different, selected from $R^{11}$. Preferably, $R^1$ and $R^8$ are each independently hydrogen, aryl, heteroaryl, aryl$C_1$-$C_3$alkyl, heteroaryl$C_1$-$C_6$alkyl, aryloxy or heteroaryloxy, wherein the heteroaryl moiety is a 5- or 6-membered aromatic ring which comprises 1, 2 or 3 heteroatoms individually selected from N, O and S, and wherein the aryl and heteroaryl moieties are each optionally substituted by 1, 2 or 3 substituents, which may be the same or different, selected from $R^{11}$. More preferably, $R^7$ and $R^8$ are each independently hydrogen, aryl, heteroaryl, aryl$C_1$-$C_3$alkyl, heteroaryl$C_1$-$C_3$alkyl, aryloxy or heteroaryloxy, wherein the heteroaryl moiety is a 5- or 6-membered aromatic ring which comprises 1 or 2 heteroatoms individually selected from N, O and S, and wherein the aryl and heteroaryl moieties are each optionally substituted by 1, 2 or 3 substituents, which may be the same or different, selected from R.

In one set of embodiments, $R^7$ is hydrogen, aryl, aryl$C_1$-$C_3$alkyl or aryloxy, wherein the aryl moieties are each optionally substituted by 1 or 2 substituents, which may be the same or different, selected from $R^{11}$. Preferably, $R^7$ is hydrogen, phenyl, benzyl or phenoxy, wherein the phenyl moiety of each $R^7$ group is optionally substituted by 1 or 2 substituents, which may be the same or different, selected from $R^{11}$. More preferably, $R^7$ is hydrogen, phenyl, benzyl, phenoxy, 2-chlorophenyl, 2-methylphenyl, 4-fluorobenzyl, 3-chlorophenoxy or 4-chlorophenoxy. Most preferably, $R^7$ is hydrogen, phenyl, phenoxy, 2-chlorophenyl, 3-chlorophenoxy or 4-chlorophenoxy.

In one set of embodiments, $R^8$ is hydrogen, aryl, heteroaryl, aryl$C_1$-$C_3$alkyl, aryloxy or heteroaryloxy, wherein the heteroaryl moiety is a 5- or 6-membered aromatic ring which comprises 1 or 2 heteroatoms individually selected from N, O and S, and wherein the aryl and heteroaryl moieties are each optionally substituted by 1, 2 or 3 substituents, which may be the same or different, selected from $R^{11}$. Preferably, $R^8$ is hydrogen, aryl, heteroaryl, aryl$C_1$-$C_3$alkyl or aryloxy, wherein the heteroaryl moiety is a 5- or 6-membered aromatic ring which comprises 1 or 2 heteroatoms individually selected from N and S, and wherein the aryl and heteroaryl moieties are each optionally substituted by 1, 2 or 3 substituents, which may be the same or different, selected from $R^{11}$.

More preferably, $R^8$ is hydrogen, phenyl, naphthyl, pyridyl, pyridazinyl, thienyl, isothiazolyl, thiazolyl, isoxazolyl, oxazolyl, pyrazolyl, imidazolyl, benzyl or phenoxy, wherein the phenyl, naphthyl, pyridyl, pyridazinyl, thienyl, isothiazolyl, thiazolyl, isoxazolyl, oxazolyl, pyrazolyl and imidazolyl moieties are each optionally substituted by 1, 2 or 3 substituents, which may be the same or different, selected from $R^{11}$. Even more preferably, $R^8$ is hydrogen, phenyl, naphthyl, 2-chlorophenyl, 2-fluorophenyl, 2-methylphenyl, 2-ethylphenyl, 2-isopropylphenyl, 2-t-butoxymethylphenyl, 3-chlorophenyl, 3-fluorophenyl, 3-methylphenyl, 4-chlorophenyl, 4-fluorophenyl, 4-bromophenyl, 4-methylphenyl, 4-trifluoromethylphenyl, 2,3-dimethylphenyl, 2,4-dimethylphenyl, 2,5-dimethylphenyl, 4-chloro-2-methylphenyl, 4-chloro-3-methylphenyl, 3-chloropyridin-2-yl, 5-chloropyridin-2-yl, 5-chloropyridin-3-yl, 6-trifluoromethylpyridin-3-yl, 2-methoxy-pyridin-4-yl, 4-methyl-3-thienyl, 3,5-dichloropyridin-2-yl, 3,5-dimethylpyridin-2-yl, 4,6-dimethylpyridin-3-yl, 5-chloro-3-methylpyridin-2-yl, 4,5-dimethylpyrazol-4-yl, 1,3,5-trimethylpyrazol-4-yl, 4,5-trimethylthiazol-2-yl, benzyl, 4-fluorobenzyl, phenoxy, 3-chlorophenoxy, 4-chlorophenoxy, 3-trifluoromethylphenoxy, 4-trifluoromethylphenoxy, 2,4-dichlorophenoxy or 2-chloro-4-trifluoromethylphenoxy.

More preferably still, $R^8$ is hydrogen, phenyl, naphthyl, 2-chlorophenyl, 2-fluorophenyl, 2-methylphenyl, 2-ethylphenyl, 2-isopropylphenyl, 2-t-butoxymethylphenyl, 3-chlorophenyl, 3-fluorophenyl, 3-methylphenyl, 4-chlorophenyl, 4-fluorophenyl, 4-bromophenyl, 4-methylphenyl, 4-trifluoromethylphenyl, 2,3-dimethylphenyl, 2,4-dimethylphenyl, 2,5-dimethylphenyl, 4-chloro-2-methylphenyl, 4-chloro-3-methylphenyl, 3-chloropyridin-2-yl, 5-chloropyridin-3-yl, 6-trifluoromethylpyridin-3-yl, 3,5-dichloropyridin-2-yl, 3,5-dimethylpyridin-2-yl, 4,6-dimethylpyridin-3-yl, 5-chloro-3-methylpyridin-2-yl, 4,5-dimethylpyrazol-4-yl, 1,3,5-trimethylpyrazol-4-yl, 4,5-trimethylthiazol-2-yl, benzyl, 4-fluorobenzyl, phenoxy, 3-chlorophenoxy, 4-chlorophenoxy, 3-trifluoromethylphenoxy, 4-trifluoromethylphenoxy, 2,4-dichlorophenoxy or 2-chloro-4-trifluoromethylphenoxy.

Most preferably, $R^8$ is hydrogen, phenyl, naphthyl, 2-methylphenyl, 2-ethylphenyl, 2-isopropylphenyl, 2-t-butoxymethylphenyl, 3-chlorophenyl, 4-chlorophenyl, 4-bromophenyl, 4-methylphenyl, 4-trifluoromethylphenyl, 2,3-dimethylphenyl, 2,5-dimethylphenyl, 4-chloro-2-methylphenyl, 4-chloro-3-methylphenyl, phenoxy, 3-chlorophenoxy, 4-chlorophenoxy, 3-trifluoromethylphenoxy, 4-trifluoromethylphenoxy, 2,4-dichlorophenoxy or 2-chloro-4-trifluoromethylphenoxy.

In a preferred set of embodiments, $R^7$ is aryl, arylC$_1$-C$_3$alkyl or aryloxy, wherein the aryl moieties are each optionally substituted by 1 or 2 substituents, which may be the same or different, selected from $R^{11}$, and $R^8$ is hydrogen. Preferably, $R^7$ is phenyl, benzyl or phenoxy, wherein the phenyl moiety of each $R^7$ group is optionally substituted by 1 or 2 substituents, which may be the same or different, selected from $R^{11}$, and $R^8$ is hydrogen.

In a particularly preferred set of embodiments, $R^7$ is hydrogen and $R^8$ is aryl, heteroaryl, arylC$_1$-C$_3$alkyl or aryloxy, wherein the heteroaryl moiety is a 5- or 6-membered aromatic ring which comprises 1 or 2 heteroatoms individually selected from N and S, and wherein the aryl and heteroaryl moieties are each optionally substituted by 1, 2 or 3 substituents, which may be the same or different, selected from $R^{11}$. More preferably, $R^7$ is hydrogen and $R^8$ is phenyl, naphthyl, pyridyl, pyridazinyl, thienyl, isothiazolyl, thiazolyl, isoxazolyl, oxazolyl, pyrazolyl, imidazolyl, benzyl or phenoxy, more preferably, phenyl, naphthyl, pyridyl, pyridazinyl, thienyl, thiazolyl, benzyl or phenoxy, wherein the phenyl, naphthyl, pyridyl, pyridazinyl, thienyl, isothiazolyl, thiazolyl, isoxazolyl, oxazolyl, pyrazolyl and imidazolyl moieties are each optionally substituted by 1, 2 or 3 substituents, which may be the same or different, selected from $R^{11}$. Even more preferably, $R^7$ is hydrogen and $R^8$ is phenyl, naphthyl, 2-chlorophenyl, 2-fluorophenyl, 2-methylphenyl, 2-ethylphenyl, 2-isopropylphenyl, 2-t-butoxymethylphenyl, 3-chlorophenyl, 3-fluorophenyl, 3-methylphenyl, 4-chlorophenyl, 4-fluorophenyl, 4-bromophenyl, 4-methylphenyl, 4-trifluoromethylphenyl, 2,3-dimethylphenyl, 2,4-dimethylphenyl, 2,5-dimethylphenyl, 4-chloro-2-methylphenyl, 4-chloro-3-methylphenyl, 3-chloropyridin-2-yl, 5-chloropyridin-3-yl, 6-trifluoromethylpyridin-3-yl, 3,5-dichloropyridin-2-yl, 3,5-dimethylpyridin-2-yl, 4,6-dimethylpyridin-3-yl, 5-chloro-3-methylpyridin-2-yl, 4,5-dimethylpyrazol-4-yl, 1,3,5-trimethylpyrazol-4-yl, 4,5-trimethylthiazol-2-yl, benzyl, 4-fluorobenzyl, phenoxy, 3-chlorophenoxy, 4-chlorophenoxy, 3-trifluoromethylphenoxy, 4-trifluoromethylphenoxy, 2,4-dichlorophenoxy or 2-chloro-4-trifluoromethylphenoxy.

More preferably still, $R^7$ is hydrogen and $R^8$ is phenyl, naphthyl, 2-methylphenyl, 2-ethylphenyl, 2-isopropylphenyl, 2-t-butoxymethylphenyl, 3-chlorophenyl, 4-chlorophenyl, 4-bromophenyl, 4-methylphenyl, 4-trifluoromethylphenyl, 2,3-dimethylphenyl, 2,5-dimethylphenyl, 4-chloro-2-methylphenyl, 4-chloro-3-methylphenyl, phenoxy, 3-chlorophenoxy, 4-chlorophenoxy, 3-trifluoromethylphenoxy, 4-trifluoromethylphenoxy, 2,4-dichlorophenoxy or 2-chloro-4-trifluoromethylphenoxy.

$R^{11}$ is halogen, cyano, C$_1$-C$_6$alkyl, C$_3$-C$_6$cycloalkyl, C$_1$-C$_6$haloalkyl, C$_1$-C$_6$alkoxy, C$_1$-C$_6$alkoxyC$_1$-C$_6$alkyl, C$_1$-C$_4$haloalkoxy or C$_1$-C$_6$alkylcarbonyl. Preferably, $R^{11}$ is halogen, C$_1$-C$_6$alkyl, C$_1$-C$_6$haloalkyl, C$_1$-C$_6$alkoxy or C$_1$-C$_4$alkoxyC$_1$-C$_4$alkyl. More preferably, $R^{11}$ is halogen, C$_1$-C$_3$alkyl, C$_1$-C$_3$haloalkyl, C$_1$-C$_3$alkoxy or C$_1$-C$_3$alkoxyC$_1$-C$_3$alkyl. Even more preferably, $R^{11}$ is chloro, fluoro, bromo, methyl, ethyl, isopropyl, trifluoromethyl, difluoromethyl, trichloromethyl, dichloromethyl, methoxy, ethoxy, isopropoxy, isopropoxymethyl or t-butoxymethyl. More preferably still, $R^{11}$ is chloro, fluoro, bromo, methyl, ethyl, isopropyl, trifluoromethyl or t-butoxymethyl. Most preferably, $R^{11}$ is chloro, fluoro, methyl or ethyl.

In a further set of embodiments, $R^7$ is hydrogen and $R^8$ is phenyl optionally substituted by 1 or 2 substituents, which may be the same or different, selected from $R^{11}$, wherein $R^{11}$ is halogen, C$_1$-C$_3$alkyl, C$_1$-C$_3$alkoxyC$_1$-C$_2$alkyl or C$_1$-C$_3$haloalkyl, or naphthyl, or pyridyl optionally substituted by 1 or 2 substituents, which may be the same or different, selected from $R^{11}$, wherein $R^{11}$ is halogen, C$_1$-C$_3$alkyl or C$_1$-C$_3$haloalkyl, or pyrazolyl optionally substituted by 1, 2 or 3 substituents, which may be the same or different, selected from $R^{11}$, wherein $R^{11}$ is C$_1$-C$_3$alkyl, or thiazolyl optionally substituted by 1 or 2 substituents, which may be the same or different, selected from $R^{11}$, wherein $R^{11}$ is C$_1$-C$_3$alkyl, or phenoxy optionally substituted by 1 or 2 substituents, which may be the same or different, selected from $R^{11}$, wherein $R^{11}$ is halogen or C$_1$-C$_6$alkyl, or benzyl, wherein the phenyl ring of the benzyl moiety is optionally substituted by a single $R^{11}$, wherein $R^{11}$ is halogen.

In another set of embodiments, $R^7$ is hydrogen and $R^8$ is phenyl optionally substituted by 1 or 2 substituents, which may be the same or different, selected from $R^{11}$, wherein $R^{11}$ is fluoro, chloro, bromo, methyl, ethyl, isopropyl, t-butoxymethyl or trifluoromethyl, or naphthyl, or pyridyl optionally substituted by 1 or 2 substituents, which may be the same or different, selected from $R^{11}$, wherein $R^{11}$ is choro, methyl or trifluoromethyl, or pyrazolyl optionally substituted with 1, 2 or 3 $R^{11}$ substituents, wherein $R^{11}$ is methyl, or thiazolyl optionally substituted with 1 or 2 $R^{11}$ substituents, wherein $R^{11}$ is methyl, or phenoxy optionally substituted with 1 or 2 substituents, which may be the same or different, selected from $R^{11}$, wherein $R^{11}$ is chloro or trifluoromethyl, or benzyl, wherein the phenyl ring of the benzyl moiety is optionally substituted by a single fluoro group.

In a further set of embodiments, $R^7$ is hydrogen and $R^8$ is phenyl optionally substituted with 1 or 2 substituents, which may be the same or different, selected from $R^{11}$, wherein $R^{11}$ is halogen, C$_1$-C$_3$alkyl, C$_1$-C$_3$alkoxyC$_1$-C$_2$alkyl or C$_1$-C$_3$haloalkyl, or naphthyl, or phenoxy optionally substituted with 1 or 2 substituents, which may be the same or different, selected from $R^{11}$, wherein $R^{11}$ is halogen or C$_1$-C$_3$haloalkyl.

In a further still set of embodiments, $R^7$ is hydrogen and $R^8$ is phenyl optionally substituted with 1 or 2 substituents, which may be the same or different, selected from $R^{11}$, wherein $R^{11}$ is chloro, bromo, methyl, ethyl, isopropyl, t-butoxymethyl or trifluoromethyl, or naphthyl, or phenoxy optionally substituted with 1 or 2 substituents, which may be the same or different, selected from $R^{11}$, wherein $R^{11}$ is chloro or trifluoromethyl.

In a compound of Formula (I) according to the present invention, preferably:

$R^1$ is C$_1$-C$_6$alkyl or C$_1$-C$_6$haloalkyl;

$R^2$ is hydroxy, C$_2$-C$_6$acyloxy or C$_2$-C$_6$acyloxyC$_1$-C$_6$alkoxy;

$R^3$ is hydrogen;

$R^4$ and $R^5$ are both methyl;

$R^6$, $R^9$ and $R^{10}$ are all hydrogen;

$R^7$ and $R^8$ are each independently hydrogen, aryl, heteroaryl, arylC$_1$-C$_3$alkyl, heteroarylC$_1$-C$_3$alkyl, aryloxy, or heteroaryloxy, wherein the heteroaryl moiety is a 5- or 6-membered aromatic ring which comprises 1, 2, 3 or 4 heteroatoms individually selected from N, O and S, and wherein the aryl and heteroaryl moieties are each optionally substituted by 1, 2 or 3 substituents, which may be the same or different, selected from $R^{11}$; and $R^{11}$ is halogen, cyano, $C_1$-$C_6$alkyl, $C_3$-$C_6$cycloalkyl, $C_1$-$C_6$haloalkyl, $C_1$-$C_6$alkoxy, $C_1$-$C_6$alkoxyC$_1$-C$_6$alkyl, $C_1$-$C_4$haloalkoxy or $C_1$-$C_6$alkylcarbonyl.

In a further compound of Formula (I) according to the present invention, preferably:

$R^1$ is $C_1$-$C_6$alkyl or $C_1$-$C_6$haloalkyl;

$R^2$ is hydroxy, $C_2$-$C_6$acyloxy or $C_2$-$C_6$acyloxyC$_1$-C$_6$alkoxy;

$R^3$ is hydrogen;

$R^4$ and $R^5$ are both methyl;

$R^6$, $R^7$, $R^9$ and $R^{10}$ are all hydrogen;

$R^8$ is hydrogen, aryl, heteroaryl, arylC$_1$-C$_3$alkyl, heteroarylC$_1$-C$_3$alkyl, aryloxy, or heteroaryloxy, wherein the heteroaryl moiety is a 5- or 6-membered aromatic ring which comprises 1, 2, 3 or 4 heteroatoms individually selected from N, O and S, and wherein the aryl and heteroaryl moieties are each optionally substituted by 1, 2 or 3 substituents, which may be the same or different, selected from $R^{11}$; and $R^{11}$ is halogen, cyano, $C_1$-$C_6$alkyl, $C_3$-$C_6$cycloalkyl, $C_1$-$C_6$haloalkyl, $C_1$-$C_6$alkoxy, $C_1$-$C_6$alkoxyC$_1$-C$_6$alkyl, $C_1$-$C_4$haloalkoxy or $C_1$-$C_6$alkylcarbonyl.

In a still further compound of Formula (I) according to the present invention, preferably:

$R^1$ is $C_1$-$C_6$alkyl or $C_1$-$C_6$haloalkyl;

$R^2$ is hydroxy, $C_2$-$C_6$acyloxy or $C_2$-$C_6$acyloxyC$_1$-C$_6$alkoxy;

$R^3$ is hydrogen;

$R^4$ and $R^5$ are both methyl;

$R^6$, $R^8$, $R^9$ and $R^{10}$ are all hydrogen;

$R^7$ is hydrogen, aryl, heteroaryl, arylC$_1$-C$_3$alkyl, heteroarylC$_1$-C$_3$alkyl, aryloxy, or heteroaryloxy, wherein the heteroaryl moiety is a 5- or 6-membered aromatic ring which comprises 1, 2, 3 or 4 heteroatoms individually selected from N, O and S, and wherein the aryl and heteroaryl moieties are each optionally substituted by 1, 2 or 3 substituents, which may be the same or different, selected from $R^{11}$; and $R^{11}$ is halogen, cyano, $C_1$-$C_6$alkyl, $C_3$-$C_6$cycloalkyl, $C_1$-$C_6$haloalkyl, $C_1$-$C_6$alkoxy, $C_1$-$C_6$alkoxyC$_1$-C$_6$alkyl, $C_1$-$C_4$haloalkoxy or $C_1$-$C_6$alkylcarbonyl.

More preferably, $R^1$ is methyl or ethyl;

$R^2$ is hydroxy, acetoxy or 2-methylpropanoyloxymethoxy;

$R^3$ is hydrogen;

$R^4$ and $R^5$ are both methyl;

$R^6$, $R^9$ and $R^{10}$ are all hydrogen;

$R^7$ and $R^8$ are each independently hydrogen, aryl, heteroaryl, arylC$_1$-C$_3$alkyl, heteroarylC$_1$-C$_3$alkyl, aryloxy, or heteroaryloxy, wherein the heteroaryl moiety is a 5- or 6-membered aromatic ring which comprises 1, 2, 3 or 4 heteroatoms individually selected from N, O and S, and wherein the aryl and heteroaryl moieties are each optionally substituted by 1, 2 or 3 substituents, which may be the same or different, selected from $R^{11}$; and $R^{11}$ is halogen, cyano, $C_1$-$C_6$alkyl, $C_3$-$C_6$cycloalkyl, $C_1$-$C_6$haloalkyl, $C_1$-$C_6$alkoxy, $C_1$-$C_6$alkoxyC$_1$-C$_6$alkyl, $C_1$-$C_4$haloalkoxy or $C_1$-$C_6$alkylcarbonyl.

Even more preferably, $R^1$ is methyl;

$R^2$ is hydroxy, acetoxy or 2-methylpropanoyloxymethoxy;

$R^3$ is hydrogen;

$R^4$ and $R^5$ are both methyl;

$R^6$, $R^9$ and $R^{10}$ are all hydrogen;

$R^7$ and $R^8$ are each independently hydrogen, aryl, heteroaryl, arylC$_1$-C$_3$alkyl or aryloxy, wherein the heteroaryl moiety is a 5- or 6-membered aromatic ring which comprises 1 or 2 heteroatoms individually selected from N and S, and wherein the aryl and heteroaryl moieties are each optionally substituted by 1, 2 or 3 substituents, which may be the same or different, selected from $R^{11}$; and $R^{11}$ is chloro, bromo, methyl, ethyl, isopropyl, trifluoromethyl or t-butoxymethyl.

In one embodiment of the invention, in a compound of Formula (I):

$R^1$ is methyl or ethyl;

$R^2$ is hydroxy, $C_2$-$C_6$acyloxy or $C_2$-$C_6$acyloxyC$_1$-C$_6$alkoxy;

$R^3$ is hydrogen or methoxy;

$R^4$ and $R^5$ are each independently methyl, ethyl or trifluoromethyl;

$R^6$, $R^8$, $R^9$ and $R^{10}$ are all hydrogen;

$R^7$ is phenyl, benzyl or phenoxy, wherein the phenyl moiety of each $R^7$ group is optionally substituted with 1 substituent selected from $R^{11}$; and $R^{11}$ is chloro, fluoro, methyl, isopropyl or t-butoxymethyl.

In another embodiment of the invention, in a compound of formula (I):

$R^1$ is methyl or ethyl;

$R^2$ is hydroxy, $C_2$-$C_6$acyloxy or $C_2$-$C_6$acyloxyC$_1$-C$_6$alkoxy;

$R^3$ is hydrogen or methoxy;

$R^4$ and $R^5$ are each independently methyl, ethyl or trifluoromethyl;

$R^6$, $R^7$, $R^9$ and $R^{10}$ each independently hydrogen or fluoro;

$R^8$ is phenyl, naphthyl, pyridyl, thienyl, pyrazolyl, thiazolyl, benzyl or phenoxy, wherein the phenyl, pyridyl, thienyl, pyrazolyl and thiazolyl moieties are each optionally substituted with 1, 2 or 3 substituents, which may be the same or different, selected from $R^{11}$; and $R^{11}$ is chloro, fluoro, bromo, methyl, ethyl, methoxy or trifluoromethyl.

In another embodiment of the invention, in a compound of formula (I):

$R^1$ is methyl or ethyl;

$R^2$ is hydroxy, $C_2$-$C_6$acyloxy or $C_2$-$C_6$acyloxyC$_1$-C$_6$alkoxy;

$R^3$ is hydrogen or methoxy;

$R^4$ and $R^5$ are each independently methyl, ethyl or trifluoromethyl;

$R^6$, $R^7$, $R^9$ and $R^{10}$ each independently hydrogen or fluoro;

$R^8$ is phenyl, naphthyl, pyridyl, pyrazolyl, thiazolyl, benzyl or phenoxy, wherein the phenyl, pyridyl, pyrazolyl and thiazolyl moieties are each optionally substituted with 1, 2 or 3 substituents, which may be the same or different, selected from $R^{11}$; and $R^{11}$ is chloro, fluoro, bromo, methyl, ethyl or trifluoromethyl.

In a further embodiment of the invention, in a compound of Formula (I):

$R^1$ is methyl;

$R^2$ is hydroxy;

$R^3$ is hydrogen;

$R^4$ and $R^5$ are both methyl;

$R^6$, $R^8$, $R^9$ and $R^{10}$ are all hydrogen;

$R^7$ is phenyl or phenoxy, wherein the phenyl moiety of each $R^8$ group is optionally substituted with 1 chloro group.

In a further still embodiment of the invention, in a compound of formula (I):
$R^1$ is methyl;
$R^2$ is hydroxy or acetoxy;
$R^3$ is hydrogen;
$R^4$ and $R^5$ are both methyl;
$R^6$, $R^7$, $R^9$ and $R^{10}$ each independently hydrogen or fluoro;
$R^8$ is phenyl, naphthyl or phenoxy, wherein the phenyl moiety of each $R^8$ group is optionally substituted with 1 or 2 substituents, which may be the same or different, selected from $R^{11}$; and
$R^{11}$ is chloro, bromo, methyl, ethyl, isopropyl, trifluoromethyl or t-butoxymethyl.

Compounds of the present invention can be made as shown in the following schemes 1 to 10, in which, unless otherwise stated, the definition of each variable is as defined above for a compound of formula (I).

The compounds of formula (I) according to the invention, wherein $R^1$, $R^2$, $R^3$, $R^4$, $R^5$, $R^6$, $R^7$, $R^8$, $R^9$ and $R^{10}$ are as defined for formula (I), can be obtained by transformation of a compound of formula (II), wherein $R^1$ and $R^2$ are as defined for formula (I) and $R^{12}$ is hydroxyl or halogen, with a compound of formula (III), wherein $R^3$, $R^4$, $R^5$, $R^6$, $R^7$, $R^8$, $R^9$ and $R^{10}$ are as defined for formula (I), with a base or a peptide coupling reagent. This is shown in Scheme 1 below.

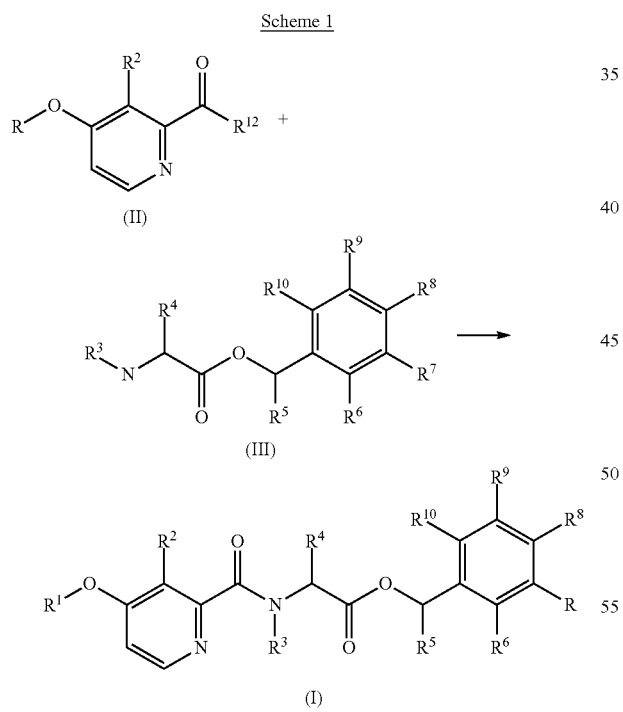

Alternatively, the compounds of formula (I), wherein $R^1$, $R^2$, $R^3$, $R^4$, $R^5$, $R^6$, $R^7$, $R^8$, $R^9$ and $R^{10}$ are as defined for formula (I), can be obtained by transformation of a compound of formula (IV), wherein $R^1$, $R^2$, $R^3$, and $R^4$ are as defined for formula (I) and $R^{12}$ is hydroxyl or halogen, with a compound of formula (V), wherein $R^5$, $R^6$, $R^7$, $R^8$, $R^9$ and $R^{10}$ are as defined for formula (I), with an acid or a base.

This is shown in Scheme 2 below.

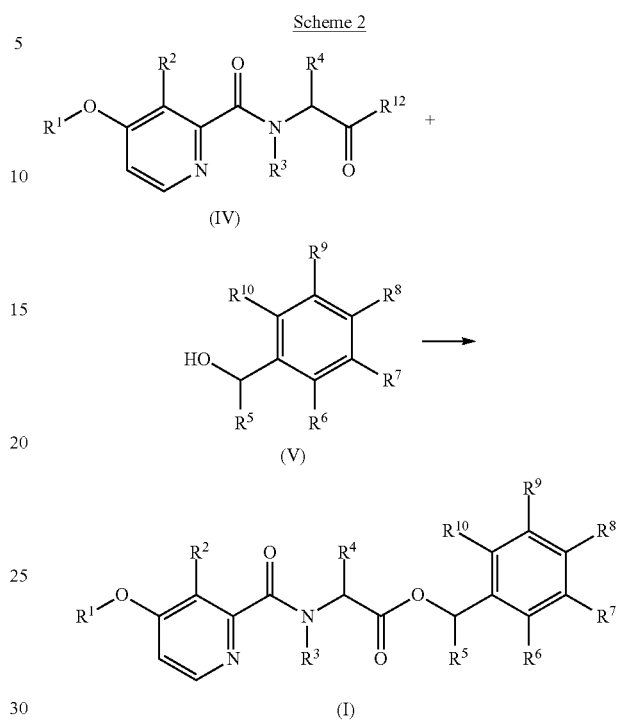

The compounds of formula (III), wherein $R^3$, $R^4$, $R^5$, $R^6$, $R^7$, $R^8$, $R^9$ and $R^{10}$ are as defined for formula (I), can be obtained by transformation of a compound of formula (VI), wherein $R^3$, $R^4$, $R^5$, $R^6$, $R^7$, $R^8$, $R^9$ and $R^{10}$ are as defined for formula (I) and $R^{13}$ is $C_1$-$C_6$alkoxycarbonyl, with an acid. This is shown in Scheme 3 below.

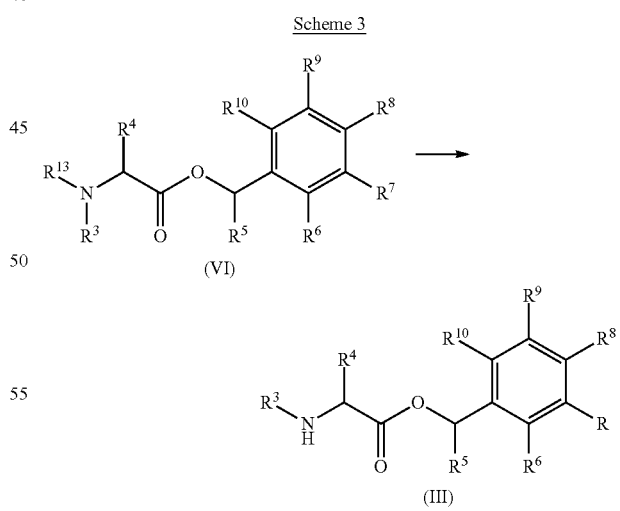

The compounds of formula (VI), wherein $R^3$, $R^4$, $R^5$, $R^6$, $R^7$, $R^8$, $R^9$ and $R^{10}$ are as defined for formula (I) and $R^{13}$ is $C_1$-$C_6$alkoxycarbonyl, can be obtained by transformation of a compound of formula (VII), wherein $R^3$ and $R^4$ are as defined for formula (I), $R^{12}$ is hydroxyl or halogen and $R^{13}$ is $C_1$-$C_6$alkoxycarbonyl, with a compound of formula (V), wherein $R^5$, $R^6$, $R^7$, $R^8$, $R^9$ and $R^{10}$ are as defined for formula (I), with an acid or a base. This is shown in Scheme 4 below.

This is shown in Scheme 6 below.

Scheme 6

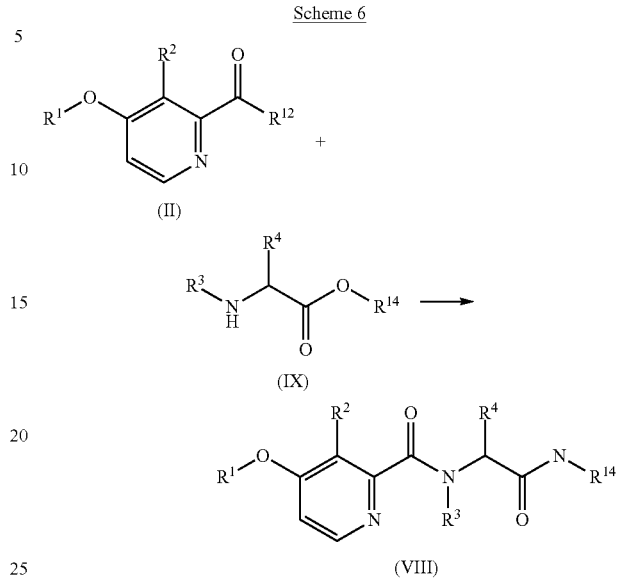

The compounds of formula (V), wherein $R^5$, $R^6$, $R^9$ and $R^{10}$ are as defined for formula (I) and at least one of $R^7$ and $R^8$ is aryl, heteroaryl, arylC$_1$-C$_3$alkyl, heteroarylC$_1$-C$_3$alkyl, aryloxy or heteroaryloxy, can be obtained by transformation of a compound of formula (X), wherein $R^5$, $R^6$, $R^9$ and $R^{10}$ are as defined for formula (I), and $R^{15}$ and $R^{16}$ are hydrogen or halogen, wherein $R^{15}$ and $R^{16}$ cannot both be hydrogen, under the conditions of transition-metal catalysis. This is shown in Scheme 7 below.

Scheme 4

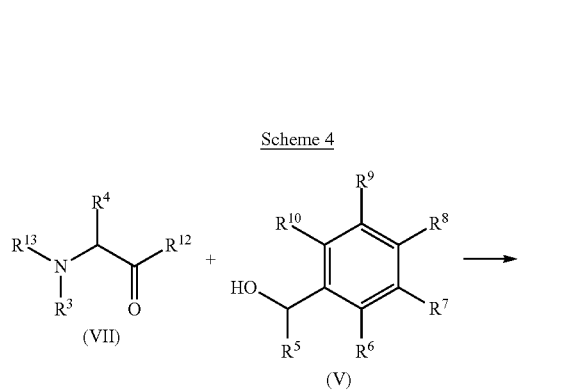

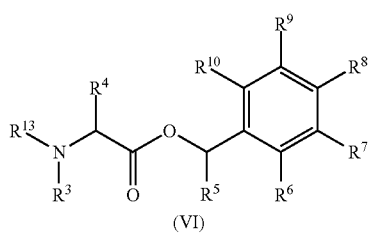

The compounds of formula (IV), wherein $R^1$, $R^2$, $R^3$, and $R^4$ are as defined for formula (I) and $R^{12}$ is hydroxyl or halogen, can be obtained by transformation of a compound of formula (VIII), wherein $R^1$, $R^2$, $R^3$, and $R^4$ are as defined for formula (I) and $R^{14}$ is C$_1$-C$_6$alkyl, with a base or a halogenation agent. This is shown in Scheme 5 below.

Scheme 7

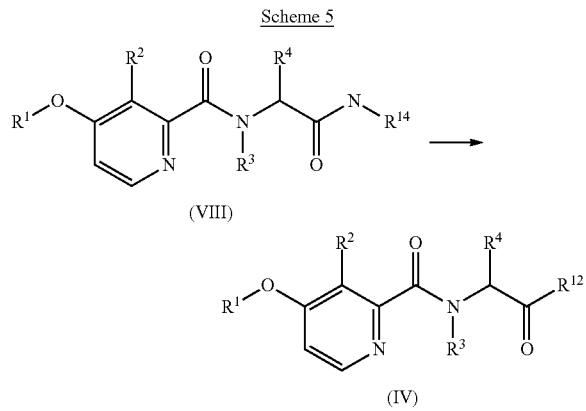

Scheme 5

The compounds of formula (I-A), wherein $R^1$, $R^3$, $R^4$, $R^5$, $R^6$, $R^7$, $R^8$, $R^9$ and $R^{10}$ are as defined for formula (I), and $R^{17}$ is C$_1$-C$_6$acyloxy, C$_1$-C$_6$haloacyloxy, C$_1$-C$_6$alkoxyC$_1$-C$_6$alkoxy, C$_1$-C$_6$haloalkoxyC$_1$-C$_6$alkoxy, C$_1$-C$_6$alkoxyC$_1$-C$_6$haloalkoxy, C$_1$-C$_6$acyloxyC$_1$-C$_6$alkoxy, C$_1$-C$_6$haloacyloxyC$_1$-C$_6$alkoxy, or C$_1$-C$_6$acyloxyC$_1$-C$_6$haloalkoxy, can be obtained by transformation of a compound of formula (I-B), wherein $R^1$, $R^3$, $R^4$, $R^5$, $R^6$, $R^7$, $R^8$, $R^9$ and $R^{10}$ are as defined for formula (I), with a compound of formula (XI), wherein $R^{17}$ is C$_1$-C$_6$acyloxy, C$_1$-C$_6$haloacyloxy, C$_1$-C$_6$alkoxyC$_1$-C$_6$alkoxy, C$_1$-C$_6$haloalkoxyC$_1$-C$_6$alkoxy, C$_1$-C$_6$alkoxyC$_1$-C$_6$haloalkoxy, C$_1$-C$_6$acyloxyC$_1$-C$_6$alkoxy, C$_1$-C$_6$haloacyloxyC$_1$-C$_6$alkoxy, or C$_1$-C$_6$acyloxyC$_1$-C$_6$haloalkoxy, and $R^{18}$ is halogen, with a base. This is shown in Scheme 8 below.

The compounds of formula (VIII), wherein $R^1$, $R^2$, $R^3$, and $R^4$ are as defined for formula (I) and $R^{14}$ is C$_1$-C$_6$alkyl, can be obtained by transformation of a compound of formula (II), wherein $R^1$ and $R^2$ are as defined for formula (I) and $R^{12}$ is hydroxyl or halogen, with a compound of formula (IX), wherein $R^3$ and $R^4$ are as defined for formula (I) and $R^{14}$ is C$_1$-C$_6$alkyl, with a base or a peptide coupling reagent.

Scheme 8

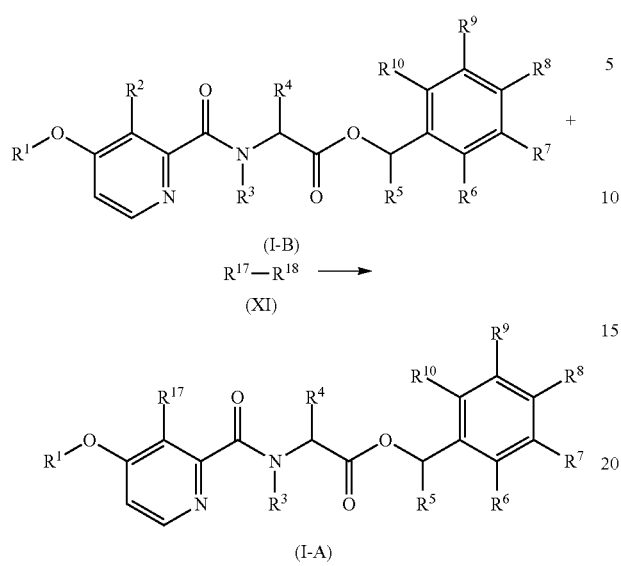

The compounds of formula (I-B), wherein $R^1$, $R^3$, $R^4$, $R^5$, $R^6$, $R^7$, $R^8$, $R^9$ and $R^{10}$ are as defined for formula (I), can be obtained by transformation of a compound of formula (II-B), wherein $R^1$ is as defined for formula (I) and $R^{12}$ is hydroxyl or halogen, with a compound of formula (III), wherein $R^3$, $R^4$, $R^5$, $R^6$, $R^7$, $R^8$, $R^9$ and $R^{10}$ are as defined for formula (I), with a base or a peptide coupling reagent. This is shown in Scheme 9 below.

Scheme 9

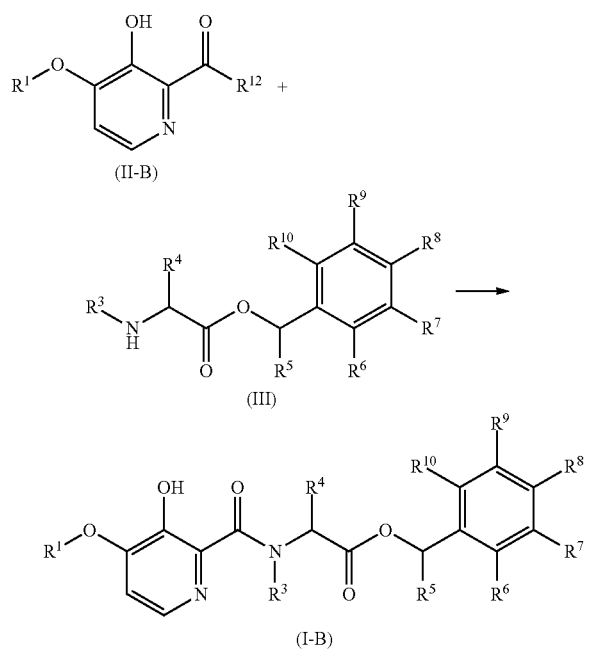

Alternatively, the compounds of formula (I-B), wherein $R^1$, $R^3$, $R^4$, $R^5$, $R^6$, $R^7$, $R^8$, $R^9$ and $R^{10}$ are as defined for formula (I), can be obtained by transformation of a compound of formula (IV-B), wherein $R^1$, $R^3$, and $R^4$ are as defined for formula (I) and $R^{12}$ is hydroxyl or halogen, with a compound of formula (V), wherein $R^5$, $R^6$, $R^7$, $R^8$, $R^9$ and $R^{10}$ are as defined for formula (I), with an acid or a base. This is shown in Scheme 10 below.

Scheme 10

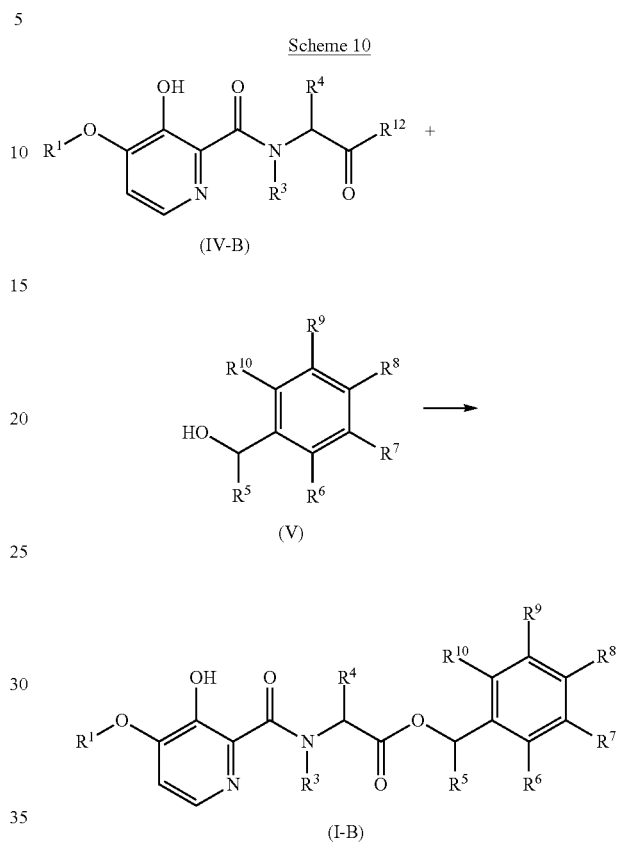

The compounds of formula (I) according to the present invention may possess two chiral centres at carbon atoms A and B as outlined below in formula (A).

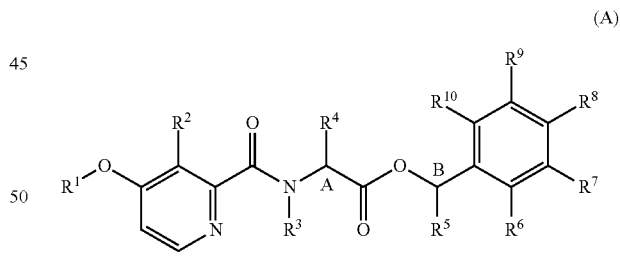

The compounds of formula (I) may exist in various diastereomeric forms, i.e., with (S,S)-, (S,R)-, (R,R)-, or (R,S)-configurations present at the A and B carbons, respectively.

Each of these stereochemical configurations as described for formula (A) may be evident for compounds of formula (I) in relation to the specific combinations of definitions for $R^1$, $R^2$, $R^3$, $R^4$, $R^5$, $R^6$, $R^7$, $R^8$, $R^9$, $R^{10}$ and $R^{11}$ for each compound described in Table 1 (a compound of formulae (1.a.001-1.a.126 to (1.bb.001-1.bb.126)) or a compound of formula (I) described in Table 2 (below).

In a preferable embodiment of the invention, the compounds of Formula (I) exist in the (S,S)-configuration.

In some embodiments of the invention, the compound of Formula (I) may be the compound of Formula (IA).

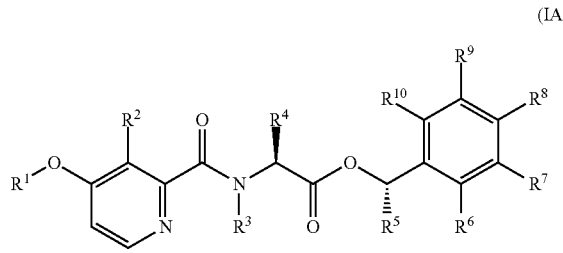

(IA)

The compounds of formula (I) can be used in the agricultural sector and related fields of use, e.g., as active ingredients for controlling plant pests or on non-living materials for control of spoilage microorganisms or organisms potentially harmful to humans. The compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use the compounds of formula (I) as a fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seeds, such as fruits, tubers or grains, or plant cuttings (e.g., rice), for the protection against fungal infections, as well as against phytopathogenic fungi occurring in the soil. The propagation material can be treated with a composition comprising a compound of formula (I) before planting: seeds, e.g., can be dressed before being sown.

The active ingredients according to the invention can also be applied to grains (coating), either by impregnating the seeds in a liquid formulation or by coating them with a solid formulation. The composition can also be applied to the planting site when the propagation material is being planted, e.g., to the seed furrow during sowing. The invention relates also to such methods of treating plant propagation material and to the plant propagation material so treated.

Furthermore, the compounds according to the present invention can be used for controlling fungi in related areas, for example in the protection of technical materials, including wood and wood related technical products, in food storage, in hygiene management.

In addition, the invention could be used to protect non-living materials from fungal attack, e.g., lumber, wall boards and paint.

The compounds of formula (I) may be, for example, effective against fungi and fungal vectors of disease as well as phytopathogenic bacteria and viruses. These fungi and fungal vectors of disease as well as phytopathogenic bacteria and viruses are for example:

Absidia corymbifera, Alternaria spp, Aphanomyces spp, Ascochyta spp, Aspergillus spp. including A. flavus, A. fumigatus, A. nidulans, A. niger, A. terrus, Aureobasidium spp. including A. pullulans, Blastomyces dermatitidis, Blumeria graminis, Bremia lactucae, Botryosphaeria spp. including B. dothidea, B. obtusa, Botrytis spp. including B. cinerea, Candida spp. including C. albicans, C. glabrata, C. krusei, C. lusitaniae, C. parapsilosis, C. tropicalis, Cephaloascus fragrans, Ceratocystis spp, Cercospora spp. including C. arachidicola, Cercosporidium personatum, Cladosporium spp, Claviceps purpurea, Coccidioides immitis, Cochliobolus spp, Colletotrichum spp. including C. musae, Cryptococcus neoformans, Diaporthe spp, Didymella spp, Drechslera spp, Elsinoe spp, Epidermophyton spp, Erwinia amylovora, Erysiphe spp. including E. cichoracearum, Eutypa lata, Fusarium spp. including F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium spp, Hemileia spp, Histoplasma spp. including H. capsulatum, Laetisaria fuciformis, Leptographium lindbergi, Leveillula taurica, Lophodermium seditiosum, Microdochium nivale, Microsporum spp, Monilinia spp, Mucor spp, Mycosphaerella spp. including M. graminicola, M. pomi, Oncobasidium theobromaeon, Ophiostoma piceae, Paracoccidioides spp, Penicillium spp. including P. digitatum, P. italicum, Petriellidium spp, Peronosclerospora spp. Including P. maydis, P. philippinensis and P. sorghi, Peronospora spp, Phaeosphaeria nodorum, Phakopsora pachyrhizi, Phellinus igniarus, Phialophora spp, Phoma spp, Phomopsis viticola, Phytophthora spp. including P. infestans, Plasmopara spp. including P. halstedii, P. viticola, Pleospora spp., Podosphaera spp. including P. leucotricha, Polymyxa graminis, Polymyxa betae, Pseudocercosporella herpotrichoides, Pseudomonas spp, Pseudoperonospora spp. including P. cubensis, P. humuli, Pseudopeziza tracheiphila, Puccinia Spp. including P. hordei, P. recondita, P. striiformis, P. triticina, Pyrenopeziza spp, Pyrenophora spp, Pyricularia spp. including P. oryzae, Pythium spp. including P. ultimum, Ramularia spp, Rhizoctonia spp, Rhizomucor pusillus, Rhizopus arrhizus, Rhynchosporium spp, Scedosporium spp. including S. apiospermum and S. prolificans, Schizothyrium pomi, Sclerotinia spp, Sclerotium spp, Septoria spp, including S. nodorum, S. tritici, Sphaerotheca macularis, Sphaerotheca fusca (Sphaerotheca fuliginea), Sporothorix spp, Stagonospora nodorum, Stemphylium spp., Stereum hirsutum, Thanatephorus cucumeris, Thielaviopsis basicola, Tilletia spp, Trichoderma spp., including T. harzianum, T. pseudokoningii, T. viride, Trichophyton spp, Typhula spp, Uncinula necator, Urocystis spp, Ustilago spp, Venturia spp. including V. inaequalis, Verticillium spp, and Xanthomonas spp.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus Bacillus.

Examples of such plants are: YieldGard® (maize variety that expresses a CryA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins from Bacillus cereus or Bacillus popilliae; or insecticidal proteins from Bacillus thuringiensis, such as b-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example Photorhabdus spp. or Xenorhabdus spp., such as Photorhabdus luminescens, Xenorhabdus nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by b-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cr3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard I® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603 x MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end, they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g., for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be, e.g., fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as above-defined, in free form or in agrochemically usable salt form, and at least one of the above-mentioned adjuvants.

The invention provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably, said composition may comprise at least one or more pesticidally active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichlorophenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2, 5-dimethylphenoxymethyl) phenyl]-2-methoxy-iminoacetamide, 4-bromo-2-cyano-N, N-dimethyl-6-trifluoromethylbenzimidazole-1-sulphonamide, a-[N-(3-chloro-2, 6-xylyl)-2-methoxyacetamido]-y-butyrolactone, 4-chloro-2-cyano-N, -dimethyl-5-p-tolylimidazole-1-sulfonamide, N-allyl-4, 5,-dimethyl-2-trimethylsilylthiophene-3-carboxamide, N-(I-cyano-1,2-dimethylpropyl)-2-(2,4-dichlorophenoxy) propionamide, N-(2-methoxy-5-pyridyl)-cyclopropane carboxamide, (.+.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4'-trifluoromethyl-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy) pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy) pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy) phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl]-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy) phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy) phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy] phenyl]-3-methoxyacrylate, methyl (E)-2-[2-[(3-methyl-pyridin-2-yloxymethyl)phenyl]-3-methoxyacrylate, methyl (E)-2-[2-[6-(2-methyl-phenoxy)pyrimidin-4-yloxy]phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy]phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-{2-(3-methoxyphenyl) methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy] phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2 (5H)-furanone; 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1, 1'-dioxide, dichlofluanid, diclomezine, dichlone, dicloran, dichlorophen, dichlozoline, diclobutrazol, diclocymet, diethofencarb, difenoconazole, difenzoquat, diflumetorim, O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)-N-benzyl-N([methyl (methyl-thioethylideneamino-oxycarbonyl) amino] thio)-ß-alaninate, etridiazole, famoxadone, fenamidone, fenaminosulf, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-iso-propyl, nuarimol, octhilinone, ofurace, organomercury compounds, orysastrobin, osthol, oxadixyl, oxasulfuron, oxathiapiprolin, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-Al, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in WO 95/19363 or WO 04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

Another aspect of invention is related to the use of a compound of formula (I) or of a preferred individual compound as above-defined, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g., harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g. harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g., in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula (I) per kg of seed, preferably from 0.01 to 10 g per kg of seed are generally sufficient.

The following mixtures of the compounds of formula (I) with active ingredients are preferred. The abbreviation "TX" means one compound selected from the group of compounds 1.a.001-1.a.126 to 1.bb.001-1.bb.126 described in Table 1, and the compounds described in Table 2 (below):

a compound selected from the group of substances consisting of petroleum oils+TX, 1,1-bis(4-chlorophenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, abamectin+TX, acequinocyl+TX, acetoprole+TX, acrinathrin+TX, aldicarb+TX, aldoxycarb+TX, alpha-cypermethrin+TX, amidithion+TX, amidoflumet+TX, amidothioate+TX, amiton+TX, amiton hydrogen oxalate+TX, amitraz+TX, aramite+TX, arsenous oxide+TX, azinphos-ethyl+TX, azinphos-methyl+TX, azobenzene+TX, azocyclotin+TX, azothoate+TX, benomyl+TX, benoxafos+TX, benzoximate+TX, benzyl benzoate+TX, bifenazate+TX, bifenthrin+TX, binapacryl+TX, bixafen+TX, brofenvalerate+TX, bromocyclen+TX, bromophos+TX, bromophos-ethyl+TX, bromopropylate+TX, buprofezin+TX, butocarboxim+TX, butoxycarboxim+TX, butylpyridaben+TX, calcium polysulfide+TX, camphechlor+TX, carbanolate+TX, carbaryl+TX, carbofuran+TX, carbophenothion+TX, cymiazole+TX, chino-methionat+TX, chlorbenside+TX, chlordimeform+TX, chlordimeform hydrochloride+TX, chlorfenapyr+TX, chlorfenethol+TX, chlorfenson+TX, chlorfensulfide+TX, chlorfenvinphos+TX, chlorobenzilate+TX, chloromebuform+TX, chloromethiuron+TX, chloropropylate+TX, chlorpyrifos+TX, chlorpyrifos-methyl+TX, chlorthiophos+TX, cinerin I+TX, cinerin II+TX, cinerins+TX, clofentezine+TX, closantel+TX, coumaphos+TX, crotamiton+TX, crotoxyphos+TX, cufraneb+TX, cyanthoate+TX, cyflumetofen+TX, cyhalothrin+TX, cyhexatin+TX, cypermethrin+TX, DCPM+TX, DDT+TX, demephion+TX, demephion-O+TX, demephion-S+TX, demeton+TX, demeton-methyl+TX, demeton-O+TX, demeton-O-methyl+TX, demeton-S+TX, demeton-S-methyl+TX, demeton-S-methylsulfon+TX, diafenthiuron+TX, dialifos+TX, diazinon+TX, dichlofluanid+TX, dichlorvos+TX, dicliphos+TX, dicofol+TX, dicrotophos+TX, dienochlor+TX, dimefox+TX, dimethoate+TX, dinactin+TX, dinex+TX, dinex-diclexine+TX, dinobuton+TX, dinocap+TX, dinocap-4+TX, dinocap-6+TX, dinocton+TX, dinopenton+TX, dinosulfon+TX, dinoterbon+TX, dioxathion+TX, diphenyl sulfone+TX, disulfiram+TX, disulfoton+TX, DNOC+TX, dofenapyn+TX, doramectin+TX, endosulfan+TX, endothion+TX, EPN+TX, eprinomectin+TX, ethion+TX, ethoate-methyl+TX, etoxazole+TX, etrimfos+TX, fenazaflor+TX, fenazaquin+TX, fenbutatin oxide+TX, fenothiocarb+TX, fenpropathrin+TX, fenpyrad+TX, fenpyroximate+TX, fenpyrazamine+TX, fenson+TX, fentrifanil+TX, fenvalerate+TX, fipronil+TX, fluacrypyrim+TX, fluazuron+TX, flubenzimine+TX, flucycloxuron+TX, flucythrinate+TX, fluenetil+TX, flufenoxuron+TX, flumethrin+TX, fluorbenside+TX, fluvalinate+TX, FMC 1137+TX, formetanate+TX, formetanate hydrochloride+TX, formothion+TX, formparanate+TX, gamma-HCH+TX, glyodin+TX, halfenprox+TX, heptenophos+TX, hexadecyl cyclopropanecarboxylate+TX, hexythiazox+TX, iodomethane+TX, isocarbophos+TX, jasmolin I+TX, jasmolin II+TX, jodfenphos+TX, lindane+TX, lufenuron+TX, malathion+TX, malonoben+TX, mecarbam+TX, mephosfolan+TX, mesulfen+TX, methacrifos+TX, methamidophos+TX, methidathion+TX, methiocarb+TX, methomyl+TX, methyl bromide+TX, metolcarb+TX, mevinphos+TX, mexacarbate+TX, milbemectin+TX, milbemycin oxime+TX, mipafox+TX, monocrotophos+TX, morphothion+TX, moxidectin+TX, naled+TX, 4-chloro-2-(2-chloro-2-methylpropyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TXomethoate+TX, oxamyl+TX, oxydeprofos+TX, oxydisulfoton+TX, pp'-DDT+TX, parathion+TX, permethrin+TX, phenkapton+TX, phenthoate+TX, phorate+TX, phosalone+TX, phosfolan+TX, phosmet+TX, phosphamidon+TX, phoxim+TX, pirimiphos-methyl+TX, polychloroterpenes+TX, polynactins+TX, proclonol+TX, profenofos+TX, promacyl+TX, propargite+TX, propetamphos+TX, propoxur+TX, prothidathion+TX, prothoate+TX, pyrethrin I+TX, pyrethrin II+TX, pyrethrins+TX, pyridaben+TX, pyridaphenthion+TX, pyrimidifen+TX, pyrimitate+TX, quinalphos+TX, quintiofos+TX, R-1492+TX, phosglycin+TX, rotenone+TX, schradan+TX, sebufos+TX, selamectin+TX, sophamide+TX, spirodiclofen+TX, spiromesifen+TX, SSI-121+TX, sulfiram+TX, sulfluramid+TX, sulfotep+TX, sulfur+TX, diflovidazin+TX, tau-fluvalinate+TX, tebufenpyrad+TX, TEPP+TX, terbam+TX, tetrachlorvinphos+TX, tetradifon+TX, tetranactin+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trichlorfon+TX, trifenofos+TX, trinactin+TX, vamidothion+TX, vaniliprole, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, emamectin+TX, emamectin benzoate+TX, piperazine+TX, spinosad+TX, thiophanate+TX, chloralose+TX, endrin+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, +TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis(dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus firmus*+TX, *Bacillus sphaericus* Neide+TX, *Bacillus thuringiensis* Berliner+TX, *Bacillus thuringiensis* subsp. *aizawai*+TX, *Bacillus thuringiensis* subsp. *israelensis*+TX, *Bacillus thuringiensis* subsp. *japonensis*+TX, *Bacillus thuringiensis* subsp. *kurstaki*+TX, *Bacillus thuringiensis* subsp. *tenebrionis*+TX, *Beauveria bassiana*+TX, *Beauveria brongniartii*+TX, *Chrysoperla carnea*+TX, *Cryptolaemus montrouzieri*+TX, *Cydia pomonella* GV+TX, *Dacnusa*

*sibirica*+TX, *Diglyphus isaea*+TX, *Encarsia formosa*+TX, *Eretmocerus eremicus*+TX, *Helicoverpa zea* NPV+TX, *Heterorhabditis bacteriophora* and *H. megidis*+TX, *Hippolomia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, *Neodiprion sertifer* NPV and *N. lecontei* NPV+TX, *Orius* spp.+TX, *Paecilomyces fumosoroseus*+TX, *Phytoseiulus persimilis*+TX, *Spodoptera exigua* multicapsid nuclear polyhedrosis virus+TX, *Steinernema bibionis*+TX, *Steinernema carpocapsae*+TX, *Steinernema feltiae*+TX, *Steinernema glaseri*+TX, *Steinernema riobrave*+TX, *Steinernema riobravis*+TX, *Steinernema scapterisci*+TX, *Steinernema* spp.+TX, *Trichogramma* spp.+TX, *Typhlodromus occidentalis*+TX, *Verticillium lecanii*+TX, apholate+TX, bisazir+TX, busulfan+TX, diflubenzuron+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-o with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, gossyplure+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure B$_1$+TX, trimedlure B$_2$+TX, trimedlure C, trunc-call+TX, 2-(octylthio)-ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquinbutyl+TX, methylneodecanamide+TX, oxamate+TX, picaridin+TX, 1-dichloro-1-nitroethane+TX, 1,1-dichloro-2,2-bis(4-ethylphenyl)ethane+TX, 1,2-dichloropropane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl)aminophenyl methylcarbamate+TX, 2-thiocyanatoethyl laurate+TX, 3-bromo-1-chloroprop-1-ene+TX, 3-methyl-1-phenylpyrazol-5-yl dimethylcarbamate+TX, 4-methyl(prop-2-ynyl)amino-3,5-xylyl methylcarbamate+TX, 5,5-dimethyl-3-oxocyclohex-1-enyl dimethylcarbamate+TX, acephate+TX, acetamiprid+TX, acethion+TX, acrylonitrile+TX, alanycarb+TX, aldrin+TX, allethrin+TX, allosamidin+TX, allyxycarb+TX, alpha-ecdysone+TX, aluminium phosphide+TX, aminocarb+TX, anabasine+TX, athidathion+TX, azadirachtin+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, bendiocarb+TX, benfuracarb+TX, bensultap+TX, beta-cyfluthrin+TX, beta-cypermethrin+TX, bioallethrin+TX, bioallethrin S-cyclopentenyl isomer+TX, bioethanomethrin+TX, biopermethrin+TX, bioresmethrin+TX, bis(2-chloroethyl)ether+TX, bistrifluron+TX, borax+TX, bromfenvinfos+TX, bromo-DDT+TX, bufencarb+TX, butacarb+TX, butathiofos+TX, butonate+TX, cadusafos+TX, calcium arsenate+TX, calcium cyanide+TX, carbon disulfide+TX, carbon tetrachloride+TX, carbosulfan+TX, cartap+TX, cartap hydrochloride+TX, cevadine+TX, chlorbicyclen+TX, chlordane+TX, chlordecone+TX, chlorethoxyfos+TX, chlorfluazuron+TX, chlormephos+TX, chloroform+TX, chloropicrin+TX, chlorphoxim+TX, chlorprazophos+TX, chromafenozide+TX, cis-resmethrin+TX, cismethrin+TX, clocythrin+TX, cloethocarb+TX, clothianidin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cycloprothrin+TX, cyfluthrin+TX, cyphenothrin+TX, cyromazine+TX, cythioate+TX, d-limonene+TX, d-tetramethrin+TX, DAEP+TX, dazomet+TX, decarbofuran+TX, deltamethrin+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, dinotefuran+TX, diofenolan+TX, dioxabenzofos+TX, dioxacarb+TX, dithicrofos+TX, DSP+TX, ecdysterone+TX, EI 1642+TX, EMPC+TX, empenthrin+TX, EPBP+TX, epofenonane+TX, esfenvalerate+TX, etaphos+TX, ethiofencarb+TX, ethiprole+TX, ethoprophos+TX, ethyl formate+TX, ethylene dibromide+TX, ethylene dichloride+TX, ethylene oxide+TX, etofenprox+TX, EXD+TX, famphur+TX, fenamiphos+TX, fenchlorphos+TX, fenethacarb+TX, fenfluthrin+TX, fenitrothion+TX, fenobucarb+TX, fenoxacrim+TX, fenoxycarb+TX, fenpirithrin+TX, fensulfothion+TX, fenthion-ethyl+TX, flonicamid+TX, flubendiamide+TX, flucofuron+TX, flufenerim+TX, flufenprox+TX, fonofos+TX, fosmethilan+TX, fospirate+TX, fosthiazate+TX, fosthietan+TX, furathiocarb+TX, furethrin+TX, gamma-cyhalothrin+TX, guazatine+TX, guazatine acetates+TX, sodium tetrathiocarbonate+TX, halfenprox+TX, halofenozide+TX, HCH+TX, HEOD+TX, heptachlor+TX, heterophos+TX, hexaflumuron+TX, HHDN+TX, hydramethylnon+TX, hydrogen cyanide+TX, hydroprene+TX, hyquincarb+TX, imidacloprid+TX, imiprothrin+TX, indoxacarb+TX, IPSP+TX, isazofos+TX, isobenzan+TX, isodrin+TX, isofenphos+TX, isolane+TX, isoprocarb+TX, isoprothiolane+TX, isothioate+TX, isoxathion+TX, juvenile hormone I+TX, juvenile hormone II+TX, juvenile hormone III+TX, kelevan+TX, kinoprene+TX, lambda-cyhalothrin+TX, lead arsenate+TX, lepimectin+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metaflumizone+TX, metam+TX, metam-potassium+TX, metam-sodium+TX, methanesulfonyl fluoride+TX, methocrotophos+TX, methoprene+TX, methothrin+TX, methoxychlor+TX, methoxyfenozide+TX, methyl isothiocyanate+TX, methylchloroform+TX, methylene chloride+TX, metofluthrin+TX, metoxadiazone+TX, mirex+TX, naftalofos+TX, naphthalene+TX, NC-170+TX, nicotine+TX, nicotine sulfate+TX, nitenpyram+TX, nithiazine+TX, nornicotine+TX, novaluron+TX, noviflumuron+TX, O-5-dichloro-4-iodophenyl O-ethyl ethylphosphonothioate+TX, O,O-diethyl O-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, oxydemeton-methyl+TX, para-dichlorobenzene+TX, parathion-methyl+TX, pentachlorophenol+TX, pentachlorophenyl laurate+TX, permethrin+TX, PH 60-38+TX, phenkapton+TX, phenothrin+TX, phosnichlor+TX, phosphine+TX, phoxim-methyl+TX, pirimetaphos+TX, pirimicarb+TX, pirimiphos-ethyl+TX, polychlorodicyclopentadiene isomers+TX, potassium arsenite+TX, potassium thiocyanate+TX, prallethrin+TX, precocene I+TX, precocene II+TX, precocene III+TX, primidophos+TX, profluthrin+TX, promecarb+TX, propaphos+TX, prothiofos+TX, protrifenbute+TX, pymetrozine+TX, pyraclofos+TX, pyrazophos+TX, pyresmethrin+TX, pyridalyl+TX, pyriproxyfen+TX, quassia+TX, quinalphos-methyl+TX, quinothion+TX, rafoxanide+TX, resmethrin+TX, rotenone+TX, kadethrin+TX, ryania+TX, ryanodine+TX, sabadilla)+TX, schradan+TX, sebufos+TX, selamectin+TX, SI-0009+TX, silafluofen+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, spirotetramat+TX, sulcofuron+TX, sulcofuron-sodium+TX, sulfuryl fluoride+TX, sulprofos+TX, tar oils+TX, tazimcarb+TX, TDE+TX, tebufenozide+TX, tebupirimfos+TX, teflubenzuron+TX, tefluthrin+TX, temephos+TX, terallethrin+TX, terbufos+TX, tetrachloroethane+TX, tetramethrin+TX, theta-cypermethrin+TX, thiacloprid+TX, thiamethoxam+TX, thicrofos+TX, thiocyclam+TX, thiocyclam hydrogen oxalate+TX, thiodicarb+TX, thionazin+TX, thiosultap+TX, thiosultap-sodium+TX, tolfenpyrad+TX, tralomethrin+TX, transfluthrin+TX, transpermethrin+TX, triazamate+TX, trichlormetaphos-3+TX, trichloronat+TX, triflumuron+TX, trimethacarb+TX, tolprocarb+TX, triclopyricarb+TX, triprene+TX, veratridine+TX, veratrine+TX, XMC+TX, xylylcarb+TX, zeta-cypermethrin+TX, zetamethrin+TX, zinc phosphide+TX, zolaprofos+TX, and brofluthrinate+TX, cyantraniliprole+TX, chlorantraniliprole+TX, cyenopyrafen+TX, pyrifluquinazon+TX, spinetoram+TX, sulfoxaflor+TX, flufiprole+TX, meperfluthrin+TX, tetramethylfluthrin+TX, triflumezopyrim+TX,bis(tributyltin) oxide+TX, bromoacetamide+TX, ferric phosphate+TX, metaldehyde+TX, niclosamide+TX, niclosamide-olamine+TX, tributyltin oxide+TX, pyrimorph+TX, trifenmorph+TX, pyriprole+TX, imicyafos+TX, 1,2-dibromo-3-chloropropane+TX, 1,3-dichloropropene+TX, 3,4-dichlorotetrahydrothiophene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, benclothiaz+TX, cytokinins+TX, DCIP+TX, furfural+TX, isamidofos+TX, kinetin+TX, *Myrothecium verrucaria* composition+TX, phosphocarb+TX, tetrachlorothiophene+TX, xylenols+TX, zeatin+TX, fluensulfone+TX,potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride)+TX, norbormide+TX, phosacetim+TX, phosphorus+TX, pindone+TX, pyrinuron+TX, scilliroside+TX, sodium fluoroacetate+TX, thallium sulfate+TX, warfarin+TX, 2-(2-butoxyethoxy) ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene)+TX, thiram+TX, zinc naphthenate+TX, ziram+TX, imanin+TX, ribavirin+TX, mercuric oxide+TX, thiophanate-methyl+TX, azaconazole+TX, bitertanol+TX, bromuconazole+TX, cyproconazole+TX, difenoconazole+TX, diniconazole+TX, epoxiconazole+TX, fenbuconazole+TX, fluquinconazole+TX, flusilazole+TX, flutriafol+TX, furametpyr+TX, hexaconazole+TX, imazalil+TX, imibenconazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, simeconazole+TX, tebuconazole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidine+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, metalaxyl+TX, R-metalaxyl+TX, ofurace+TX, oxadixyl+TX, carbendazim+TX, debacarb+TX, fuberidazole+TX, thiabendazole+TX, chlozolinate+TX, dichlozoline+TX, iprodione+TX, myclozoline+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, f fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb+TX, chlorothalonil+TX, cyflufenamid+TX, cymoxanil+TX, diclocymet+TX, diclomezine+TX, dicloran+TX, diethofencarb+TX, dimethomorph+TX, flumorph+TX, dithianon+TX, ethaboxam+TX, etridiazole+TX, famoxadone+TX, fenamidone+TX, fenoxanil+TX, ferimzone+TX, fluazinam+TX, fluopicolide+TX, flusulfamide+TX, fluxapyroxad+TX, fenhexamid+TX, fosetyl-aluminium+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, afidopyropen+ TX,pyflubumide+TX, isoflucypram+TX, isotianil+TX, dipymetitrone+TX, 6-ethyl-5,7-dioxo-pyrrolo[4,5][1,4] dithiino[1,2-c]isothiazole-3-carbonitrile+TX, 2-(difluoromethyl)-N-[3-ethyl-1,1-dimethyl-indan-4-yl]pyridine-3-carboxamide+TX, 4-(2,6-difluorophenyl)-6-methyl-5-phenylpyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+ TX, 4-(2-Bromo-4-fluorophenyl)-N-(2-chloro-6-fluorophenyl)-1,3-dimethyl-1H-pyrazol-5-amine+TX, fluindapyr+TX, jiaxiangjunzhi+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl] propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, pyraziflumid+TX, inpyrfluxam+ TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+ TX, N'-(2,5-dimethyl-4-phenoxy-phenyl)-N-ethyl-N-methyl-formamidine+TX, N'-[4-(4,5-dichlorothiazol-2-yl) oxy-2,5-dimethyl-phenyl]-N-ethyl-N-methyl-formamidine+ TX, [2-[3-[2-[1-[2-[3,5-bis(difluoromethyl)pyrazol-1-yl] acetyl]-4-piperidyl]thiazol-4-yl]-4,5-dihydroisoxazol-5-yl]-3-chloro-phenyl] methanesulfonate+TX, but-3-ynyl N-[6-[[[(Z)-[(1-methyltetrazol-5-yl)-phenyl-methylene]amino] oxymethyl]-2-pyridyl]carbamate+TX, methyl N-[[5-[4-(2,4-dimethylphenyl)triazol-2-yl]-2-methyl-phenyl]methyl] carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl] pyrazole-4-carboxamide+TX, 1-[2-[[1-(4-chlorophenyl) pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flutianil+ TX, fluopimomide+TX, pyrapropoyne+TX, picarbutrazox+ TX, 2-(difluoromethyl)-N-(3-ethyl-1,1-dimethyl-indan-4-yl)pyridine-3-carboxamide+TX, 2-(difluoromethyl)-N-((3R)-1,1,3-trimethylindan-4-yl)pyridine-3-carboxamide+ TX, 4-[[6-[2-(2,4-difluorophenyl)-1,1-difluoro-2-hydroxy-3-(1,2,4-triazol-1-yl)propyl]-3-pyridyl]oxy]benzonitrile+ TX, metyltetraprole+TX, 2-(Difluororethyl)-N-((3R)-1,1,3-trimethylindan-4-yl)pyridine-3-carboxamide+TX, α-(1,1-dimethylethyl)-α-[4'-(trifluoromethoxy)[1,1'-biphenyl]-4-yl]-5-pyrimidinemethanol+TX, Fluoxapiprolin+TX, Enoxastrobin+TX, 4-[[6-[2-(2,4-difluorophenyl)-1,1-difluoro-2-hydroxy-3-(1,2,4-triazol-1-yl)propyl]-3-pyridyl] oxy] benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy] benzonitrile+TX, 4-[[6-[2-(2,4-difluoromethyl)-1,1-difluoro-2-hydroxy-3-(5-thioxo-4H-1,2,4-triazol-1-yl)propyl]-3-pyridyl]oxy]benzonitrile+TX, trinexapac+TX, coumoxystrobin+TX, N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl] propanamide+TX, N-ethyl-2-methyl-N-[[4-[5-(trifluoromethyl)-1,2,4-oxadiazol-3-yl]phenyl]methyl] propanamide+TX, 1-methoxy-3-methyl-1-[[4-[5-(trifluoromethyl)-1,2,4-oxadiazol-3-yl]phenyl]methyl] urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl] phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl] phenyl]methyl]isoxazolidin-3-one+TX, 5,5-dimethyl-2-[[4-[5-(trifluoromethyl)-1,2,4-oxadiazol-3-yl]phenyl]methyl] isoxazolidin-3-one+TX, ethyl 1-[[4-[5-(trifluoromethyl)-1,2,4-oxadiazol-3-yl]phenyl]methyl]pyrazole-4-carboxylate+ TX, N,N-dimethyl-1-[[4-[5-(trifluoromethyl)-1,2,4-oxadiazol-3-yl]phenyl]methyl]-1,2,4-triazol-3-amine+TX.

The compounds in this paragraph may be prepared from the methods described in WO 2017/055473, WO 2017/055469, WO 2017/093348 and WO 2017/118689.

The above described mixing partners are known. Where the active ingredients are included in "The Online Pesticide Manual" under the internet address http://www.bcpc.org. Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed.

The active ingredient mixture of the compounds of formula (I) selected from a compound 1.a.001-1.a.126 to 1.bb.001-1.bb.126 described in Table 1, and the compounds described in Table 2 (below), and an active ingredient as described above are preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from one of compounds 1.a.001-1.a.126 to 1.bb.001-1.bb.126 described in Table 1, and the compounds described in Table 2 (below), and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from a compound 1.a.001-1.a.126 to 1.bb.001-1.bb.126 described in Table 1, and the compounds described in Table 2 (below), and the active ingredient(s) as described above, is not essential for working the present invention.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g., by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g., as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Table 1 below illustrates examples of individual compounds of formula (I) according to the invention.

TABLE 1

Individual compounds of formula (I) according to the invention

| Compound No. | $R^1$ | $R^2$ | $R^3$ | $R^4$ | $R^5$ |
|---|---|---|---|---|---|
| 001 | $CH_3$ | OH | H | $CH_3$ | $CH_3$ |
| 002 | $CH_3$ | OH | H | $CH_3$ | $CH_2CH_3$ |
| 003 | $CH_3$ | OH | H | $CH_3$ | $CF_3$ |
| 004 | $CH_3$ | OH | H | $CH_2CH_3$ | $CH_3$ |
| 005 | $CH_3$ | OH | H | $CH_2CH_3$ | $CH_2CH_3$ |
| 006 | $CH_3$ | OH | H | $CH_2CH_3$ | $CF_3$ |
| 007 | $CH_3$ | OH | H | $CF_3$ | $CH_3$ |
| 008 | $CH_3$ | OH | H | $CF_3$ | $CH_2CH_3$ |
| 009 | $CH_3$ | OH | H | $CF_3$ | $CF_3$ |
| 010 | $CH_3$ | OH | $OCH_3$ | $CH_3$ | $CH_3$ |
| 011 | $CH_3$ | OH | $OCH_3$ | $CH_3$ | $CH_2CH_3$ |
| 012 | $CH_3$ | OH | $OCH_3$ | $CH_3$ | $CF_3$ |
| 013 | $CH_3$ | OH | $OCH_3$ | $CH_2CH_3$ | $CH_3$ |
| 014 | $CH_3$ | OH | $OCH_3$ | $CH_2CH_3$ | $CH_2CH_3$ |
| 015 | $CH_3$ | OH | $OCH_3$ | $CH_2CH_3$ | $CF_3$ |
| 016 | $CH_3$ | OH | $OCH_3$ | $CF_3$ | $CH_3$ |
| 017 | $CH_3$ | OH | $OCH_3$ | $CF_3$ | $CH_2CH_3$ |
| 018 | $CH_3$ | OH | $OCH_3$ | $CF_3$ | $CF_3$ |
| 019 | $CH_3$ | $OC(=O)CH_3$ | H | $CH_3$ | $CH_3$ |
| 020 | $CH_3$ | $OC(=O)CH_3$ | H | $CH_3$ | $CH_2CH_3$ |
| 021 | $CH_3$ | $OC(=O)CH_3$ | H | $CH_3$ | $CF_3$ |
| 022 | $CH_3$ | $OC(=O)CH_3$ | H | $CH_2CH_3$ | $CH_3$ |
| 023 | $CH_3$ | $OC(=O)CH_3$ | H | $CH_2CH_3$ | $CH_2CH_3$ |
| 024 | $CH_3$ | $OC(=O)CH_3$ | H | $CH_2CH_3$ | $CF_3$ |
| 025 | $CH_3$ | $OC(=O)CH_3$ | H | $CF_3$ | $CH_3$ |
| 026 | $CH_3$ | $OC(=O)CH_3$ | H | $CF_3$ | $CH_2CH_3$ |
| 027 | $CH_3$ | $OC(=O)CH_3$ | H | $CF_3$ | $CF_3$ |
| 028 | $CH_3$ | $OC(=O)CH_3$ | $OCH_3$ | $CH_3$ | $CH_3$ |
| 029 | $CH_3$ | $OC(=O)CH_3$ | $OCH_3$ | $CH_3$ | $CH_2CH_3$ |
| 030 | $CH_3$ | $OC(=O)CH_3$ | $OCH_3$ | $CH_3$ | $CF_3$ |
| 031 | $CH_3$ | $OC(=O)CH_3$ | $OCH_3$ | $CH_2CH_3$ | $CH_3$ |

TABLE 1-continued

Individual compounds of formula (I) according to the invention

| Compound No. | R¹ | R² | R³ | R⁴ | R⁵ |
|---|---|---|---|---|---|
| 032 | CH₃ | OC(=O)CH₃ | OCH₃ | CH₂CH₃ | CH₂CH₃ |
| 033 | CH₃ | OC(=O)CH₃ | OCH₃ | CH₂CH₃ | CF₃ |
| 034 | CH₃ | OC(=O)CH₃ | OCH₃ | CF₃ | CH₃ |
| 035 | CH₃ | OC(=O)CH₃ | OCH₃ | CF₃ | CH₂CH₃ |
| 036 | CH₃ | OC(=O)CH₃ | OCH₃ | CF₃ | CF₃ |
| 037 | CH₃ | OC(=O)CH₂CH₃ | H | CH₃ | CH₃ |
| 038 | CH₃ | OC(=O)CH₂CH₃ | H | CH₃ | CH₂CH₃ |
| 039 | CH₃ | OC(=OCH₂CH₃ | H | CH₃ | CF₃ |
| 040 | CH₃ | OC(=O)CH₂CH₃ | H | CH₂CH₃ | CH₃ |
| 041 | CH₃ | OC(=O)CH₂CH₃ | H | CH₂CH₃ | CH₂CH₃ |
| 042 | CH₃ | OC(=O)CH₂CH₃ | H | CH₂CH₃ | CF₃ |
| 043 | CH₃ | OC(=O)CH₂CH₃ | H | CF₃ | CH₃ |
| 044 | CH₃ | OC(=O)CH₂CH₃ | H | CF₃ | CH₂CH₃ |
| 045 | CH₃ | OC(=O)CH₂CH₃ | H | CF₃ | CF₃ |
| 046 | CH₃ | OC(=O)CH₂CH₃ | OCH₃ | CH₃ | CH₃ |
| 047 | CH₃ | OC(=O)CH₂CH₃ | OCH₃ | CH₃ | CH₂CH₃ |
| 048 | CH₃ | OC(=O)CH₂CH₃ | OCH₃ | CH₃ | CF₃ |
| 049 | CH₃ | OC(=O)CH₂CH₃ | OCH₃ | CH₂CH₃ | CH₃ |
| 050 | CH₃ | OC(=O)CH₂CH₃ | OCH₃ | CH₂CH₃ | CH₂CH₃ |
| 051 | CH₃ | OC(=O)CH₂CH₃ | OCH₃ | CH₂CH₃ | CF₃ |
| 052 | CH₃ | OC(=O)CH₂CH₃ | OCH₃ | CF₃ | CH₃ |
| 053 | CH₃ | OC(=O)CH₂CH₃ | OCH₃ | CF₃ | CH₂CH₃ |
| 054 | CH₃ | OC(=O)CH₂CH₃ | OCH₃ | CF₃ | CF₃ |
| 055 | CH₃ | OCH₂OC(=O)CH₃ | H | CH₃ | CH₃ |
| 056 | CH₃ | OCH₂OC(=O)CH₃ | H | CH₃ | CH₂CH₃ |
| 057 | CH₃ | OCH₂OC(=O)CH₃ | H | CH₃ | CF₃ |
| 058 | CH₃ | OCH₂OC(=O)CH₃ | H | CH₂CH₃ | CH₃ |
| 059 | CH₃ | OCH₂OC(=O)CH₃ | H | CH₂CH₃ | CH₂CH₃ |
| 060 | CH₃ | OCH₂OC(=O)CH₃ | H | CH₂CH₃ | CF₃ |
| 061 | CH₃ | OCH₂OC(=O)CH₃ | H | CF₃ | CH₃ |
| 062 | CH₃ | OCH₂OC(=O)CH₃ | H | CF₃ | CH₂CH₃ |
| 063 | CH₃ | OCH₂OC(=O)CH₃ | H | CF₃ | CF₃ |
| 064 | CH₃ | OCH₂OC(=O)CH₃ | OCH₃ | CH₃ | CH₃ |
| 065 | CH₃ | OCH₂OC(=O)CH₃ | OCH₃ | CH₃ | CH₂CH₃ |
| 066 | CH₃ | OCH₂OC(=O)CH₃ | OCH₃ | CH₃ | CF₃ |
| 067 | CH₃ | OCH₂OC(=O)CH₃ | OCH₃ | CH₂CH₃ | CH₃ |
| 068 | CH₃ | OCH₂OC(=O)CH₃ | OCH₃ | CH₂CH₃ | CH₂CH₃ |
| 069 | CH₃ | OCH₂OC(=O)CH₃ | OCH₃ | CH₂CH₃ | CF₃ |
| 070 | CH₃ | OCH₂OC(=O)CH₃ | OCH₃ | CF₃ | CH₃ |
| 071 | CH₃ | OCH₂OC(=O)CH₃ | OCH₃ | CF₃ | CH₂CH₃ |
| 072 | CH₃ | OCH₂OC(=O)CH₃ | OCH₃ | CF₃ | CF₃ |
| 073 | CH₃ | OCH₂OC(=O)CH₂CH₃ | H | CH₃ | CH₃ |
| 074 | CH₃ | OCH₂OC(=O)CH₂CH₃ | H | CH₃ | CH₂CH₃ |
| 075 | CH₃ | OCH₂OC(=O)CH₂CH₃ | H | CH₃ | CF₃ |
| 076 | CH₃ | OCH₂OC(=O)CH₂CH₃ | H | CH₂CH₃ | CH₃ |
| 077 | CH₃ | OCH₂OC(=O)CH₂CH₃ | H | CH₂CH₃ | CH₂CH₃ |
| 078 | CH₃ | OCH₂OC(=O)CH₂CH₃ | H | CH₂CH₃ | CF₃ |
| 079 | CH₃ | OCH₂OC(=O)CH₂CH₃ | H | CF₃ | CH₃ |
| 080 | CH₃ | OCH₂OC(=O)CH₂CH₃ | H | CF₃ | CH₂CH₃ |
| 081 | CH₃ | OCH₂OC(=O)CH₂CH₃ | H | CF₃ | CF₃ |
| 082 | CH₃ | OCH₂OC(=O)CH₂CH₃ | OCH₃ | CH₃ | CH₃ |
| 083 | CH₃ | OCH₂OC(=O)CH₂CH₃ | OCH₃ | CH₃ | CH₂CH₃ |
| 084 | CH₃ | OCH₂OC(=O)CH₂CH₃ | OCH₃ | CH₃ | CF₃ |
| 085 | CH₃ | OCH₂OC(=O)CH₂CH₃ | OCH₃ | CH₂CH₃ | CH₃ |
| 086 | CH₃ | OCH₂OC(=O)CH₂CH₃ | OCH₃ | CH₂CH₃ | CH₂CH₃ |
| 087 | CH₃ | OCH₂OC(=O)CH₂CH₃ | OCH₃ | CH₂CH₃ | CF₃ |
| 088 | CH₃ | OCH₂OC(=O)CH₂CH₃ | OCH₃ | CF₃ | CH₃ |
| 089 | CH₃ | OCH₂OC(=O)CH₂CH₃ | OCH₃ | CF₃ | CH₂CH₃ |
| 090 | CH₃ | OCH₂OC(=O)CH₂CH₃ | OCH₃ | CF₃ | CF₃ |
| 091 | CH₃ | OCH₂OC(=O)CH(CH₃)₂ | H | CH₃ | CH₃ |
| 092 | CH₃ | OCH₂OC(=O)CH(CH₃)₂ | H | CH₃ | CH₂CH₃ |
| 093 | CH₃ | OCH₂OC(=O)CH(CH₃)₂ | H | CH₃ | CF₃ |
| 094 | CH₃ | OCH₂OC(=O)CH(CH₃)₂ | H | CH₂CH₃ | CH₃ |
| 095 | CH₃ | OCH₂OC(=O)CH(CH₃)₂ | H | CH₂CH₃ | CH₂CH₃ |
| 096 | CH₃ | OCH₂OC(=O)CH(CH₃)₂ | H | CH₂CH₃ | CF₃ |
| 097 | CH₃ | OCH₂OC(=O)CH(CH₃)₂ | H | CF₃ | CH₃ |
| 098 | CH₃ | OCH₂OC(=O)CH(CH₃)₂ | H | CF₃ | CH₂CH₃ |
| 099 | CH₃ | OCH₂OC(=O)CH(CH₃)₂ | H | CF₃ | CF₃ |
| 100 | CH₃ | OCH₂OC(=O)CH(CH₃)₂ | OCH₃ | CH₃ | CH₃ |
| 101 | CH₃ | OCH₂OC(=O)CH(CH₃)₂ | OCH₃ | CH₃ | CH₂CH₃ |
| 102 | CH₃ | OCH₂OC(=O)CH(CH₃)₂ | OCH₃ | CH₃ | CF₃ |
| 103 | CH₃ | OCH₂OC(=O)CH(CH₃)₂ | OCH₃ | CH₂CH₃ | CH₃ |
| 104 | CH₃ | OCH₂OC(=O)CH(CH₃)₂ | OCH₃ | CH₂CH₃ | CH₂CH₃ |
| 105 | CH₃ | OCH₂OC(=O)CH(CH₃)₂ | OCH₃ | CH₂CH₃ | CF₃ |
| 106 | CH₃ | OCH₂OC(=O)CH(CH₃)₂ | OCH₃ | CF₃ | CH₃ |

TABLE 1-continued

Individual compounds of formula (I) according to the invention

| Compound No. | R¹ | R² | R³ | R⁴ | R⁵ |
|---|---|---|---|---|---|
| 107 | $CH_3$ | $OCH_2OC(=O)CH(CH_3)_2$ | $OCH_3$ | $CF_3$ | $CH_2CH_3$ |
| 108 | $CH_3$ | $OCH_2OC(=O)CH(CH_3)_2$ | $OCH_3$ | $CF_3$ | $CF_3$ |
| 109 | $CH_2CH_3$ | OH | H | $CH_3$ | $CH_3$ |
| 110 | $CH_2CH_3$ | OH | H | $CH_3$ | $CH_2CH_3$ |
| 111 | $CH_2CH_3$ | OH | H | $CH_3$ | $CF_3$ |
| 112 | $CH_2CH_3$ | OH | H | $CH_2CH_3$ | $CH_3$ |
| 113 | $CH_2CH_3$ | OH | H | $CH_2CH_3$ | $CH_2CH_3$ |
| 114 | $CH_2CH_3$ | OH | H | $CH_2CH_3$ | $CF_3$ |
| 115 | $CH_2CH_3$ | OH | H | $CF_3$ | $CH_3$ |
| 116 | $CH_2CH_3$ | OH | H | $CF_3$ | $CH_2CH_3$ |
| 117 | $CH_2CH_3$ | OH | H | $CF_3$ | $CF_3$ |
| 118 | $CH_3CH_2$ | OH | $OCH_3$ | $CH_3$ | $CH_3$ |
| 119 | $CH_2CH_3$ | OH | $OCH_3$ | $CH_3$ | $CH_2CH_3$ |
| 120 | $CH_2CH_3$ | OH | $OCH_3$ | $CH_3$ | $CF_3$ |
| 121 | $CH_2CH_3$ | OH | $OCH_3$ | $CH_2CH_3$ | $CH_3$ |
| 122 | $CH_2CH_3$ | OH | $OCH_3$ | $CH_2CH_3$ | $CH_2CH_3$ |
| 123 | $CH_3CH_2$ | OH | $OCH_3$ | $CH_2CH_3$ | $CF_3$ |
| 124 | $CH_2CH_3$ | OH | $OCH_3$ | $CF_3$ | $CH_3$ |
| 125 | $CH_2CH_3$ | OH | $OCH_3$ | $CF_3$ | $CH_2CH_3$ |
| 126 | $CH_3CH_2$ | OH | $OCH_3$ | $CF_3$ | $CF_3$ |

Wherein there are:

a) 126 Compounds of Formula (I.a):

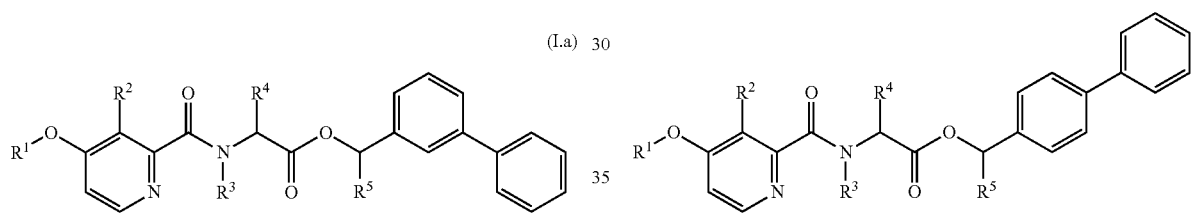

wherein $R^1$, $R^2$, $R^3$, $R^4$, and $R^5$ are as defined in Table 1.

b) 126 Compounds of Formula (I.b):

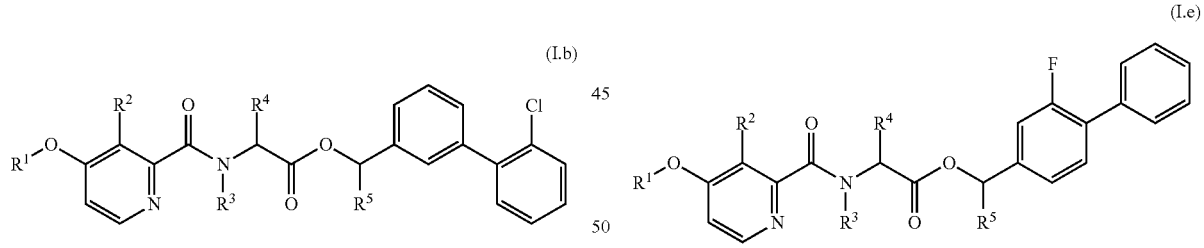

wherein $R^1$, $R^2$, $R^3$, $R^4$, and $R^5$ are as defined in Table 1.

c) 126 Compounds of Formula (I.c):

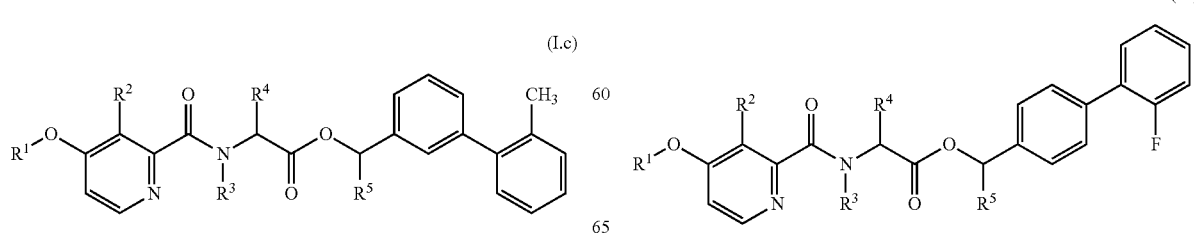

wherein $R^1$, $R^2$, $R^3$, $R^4$, and $R^5$ are as defined in Table 1.

d) 126 Compounds of Formula (I.d):

(I.d)

wherein $R^1$, $R^2$, $R^3$, $R^4$, and $R^5$ are as defined in Table 1.

e) 126 Compounds of Formula (I.e):

(I.e)

wherein $R^1$, $R^2$, $R^3$, $R^4$, and $R^5$ are as defined in Table 1.

f) 126 Compounds of Formula (I.f):

(I.f)

wherein $R^1$, $R^2$, $R^3$, $R^4$, and $R^5$ are as defined in Table 1.

g) 126 Compounds of Formula (I.g):

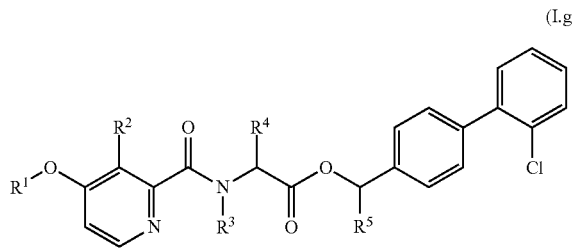

wherein $R^1$, $R^2$, $R^3$, $R^4$, and $R^5$ are as defined in Table 1.

h) 126 Compounds of Formula (I.h):

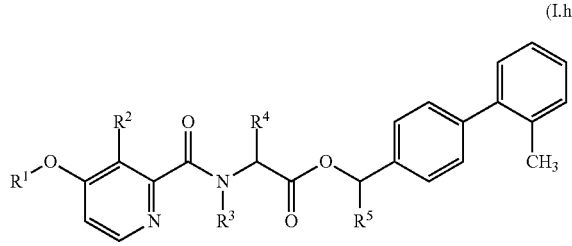

wherein $R^1$, $R^2$, $R^3$, $R^4$, and $R^5$ are as defined in Table 1.

i) 126 Compounds of Formula (I.i):

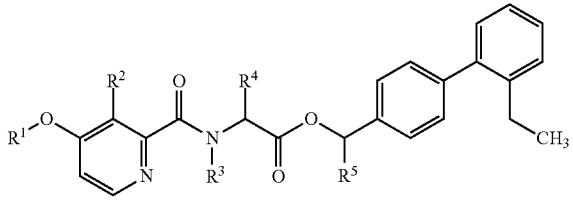

wherein $R^1$, $R^2$, $R^3$, $R^4$, and $R^5$ are as defined in Table 1.

j) 126 Compounds of Formula (I.j):

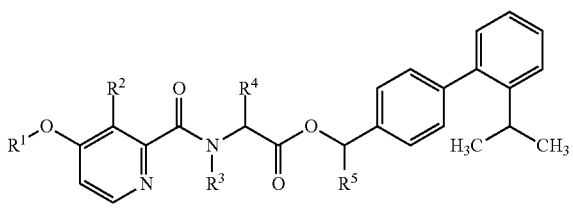

wherein $R^1$, $R^2$, $R^3$, $R^4$, and $R^5$ are as defined in Table 1.

k) 126 Compounds of Formula (I.k):

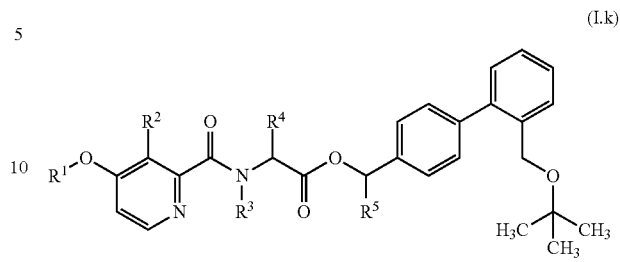

wherein $R^1$, $R^2$, $R^3$, $R^4$, and $R^5$ are as defined in Table 1.

m) 126 Compounds of Formula (I.m):

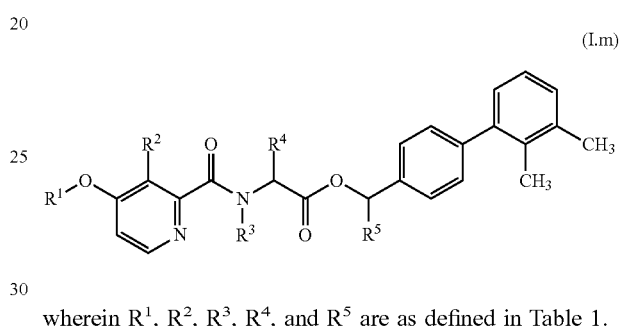

wherein $R^1$, $R^2$, $R^3$, $R^4$, and $R^5$ are as defined in Table 1.

n) 126 Compounds of Formula (I.n):

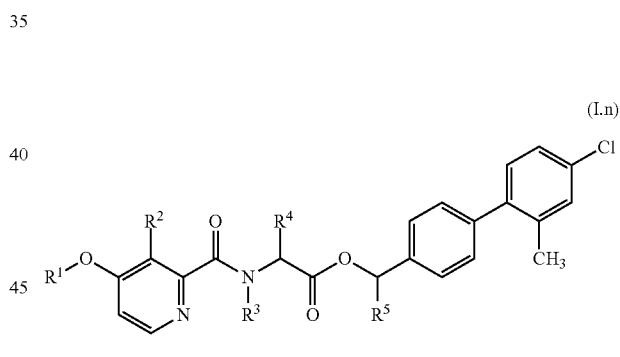

wherein $R^1$, $R^2$, $R^3$, $R^4$, and $R^5$ are as defined in Table 1.

o) 126 Compounds of Formula (I.o):

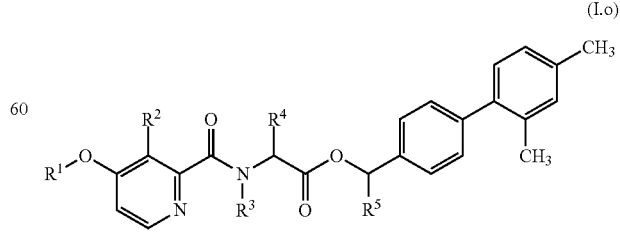

wherein $R^1$, $R^2$, $R^3$, $R^4$, and $R^5$ are as defined in Table 1.

p) 126 Compounds of Formula (I.p):

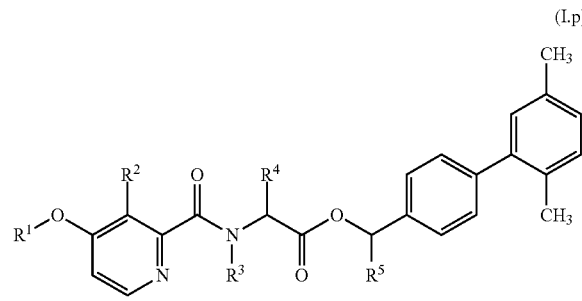

wherein $R^1$, $R^2$, $R^3$, $R^4$, and $R^5$ are as defined in Table 1.

q) 126 Compounds of Formula (I.q):

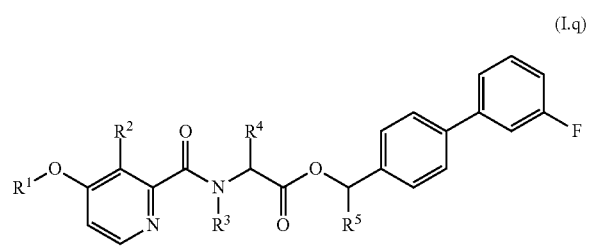

wherein $R^1$, $R^2$, $R^3$, $R^4$, and $R^5$ are as defined in Table 1.

r) 126 Compounds of Formula (I.r):

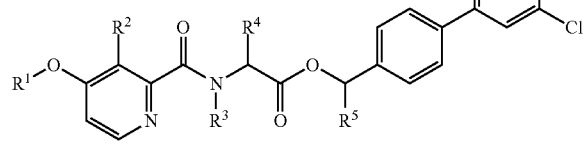

wherein $R^1$, $R^2$, $R^3$, $R^4$ and $R^5$ are as defined in Table 1.

s) 126 Compounds of Formula (I.s):

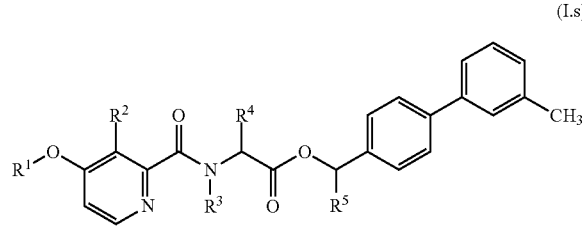

wherein $R^1$, $R^2$, $R^3$, $R^4$, and $R^5$ are as defined in Table 1.

t) 126 Compounds of Formula (I.t):

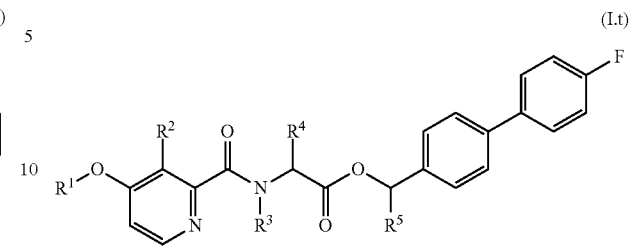

wherein $R^1$, $R^2$, $R^3$, $R^4$, and $R^5$ are as defined in Table 1.

u) 126 Compounds of Formula (I.u):

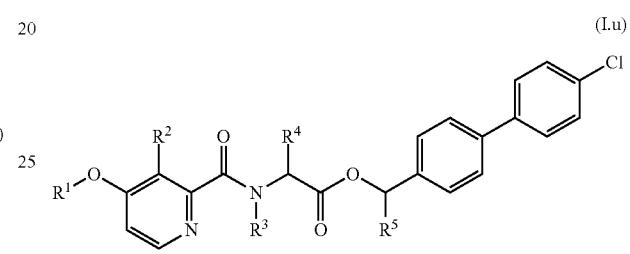

wherein $R^1$, $R^2$, $R^3$, $R^4$, and $R^5$ are as defined in Table 1.

v) 126 Compounds of Formula (I.v):

wherein $R^1$, $R^2$, $R^3$, $R^4$, and $R^5$ are as defined in Table 1.

w) 126 Compounds of Formula (I.w):

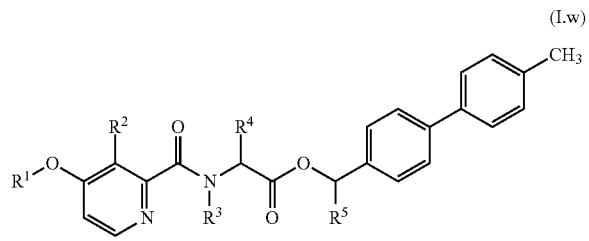

wherein $R^1$, $R^2$, $R^3$, $R^4$, and $R^5$ are as defined in Table 1.

x) 126 Compounds of Formula (I.x):

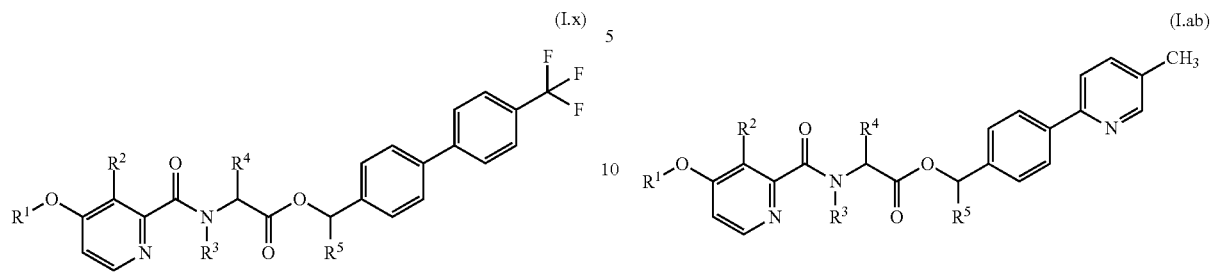

wherein $R^1$, $R^2$, $R^3$, $R^4$, and $R^5$ are as defined in Table 1.
y) 126 Compounds of Formula (I.y):

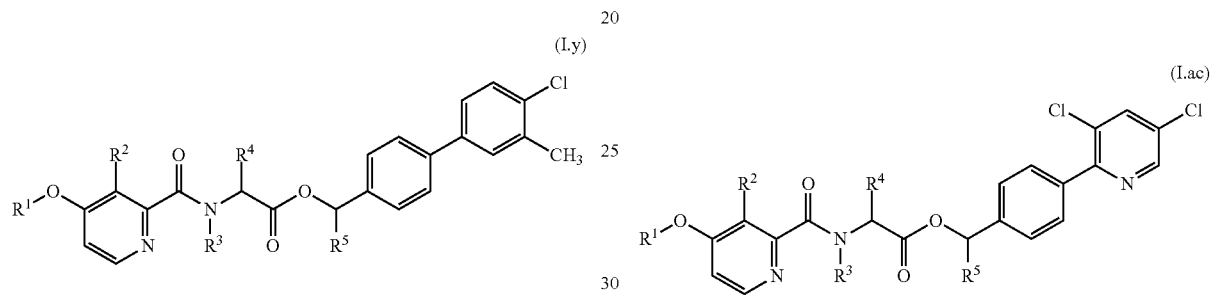

wherein $R^1$, $R^2$, $R^3$, $R^4$, and $R^5$ are as defined in Table 1.
z) 126 Compounds of Formula (I.z):

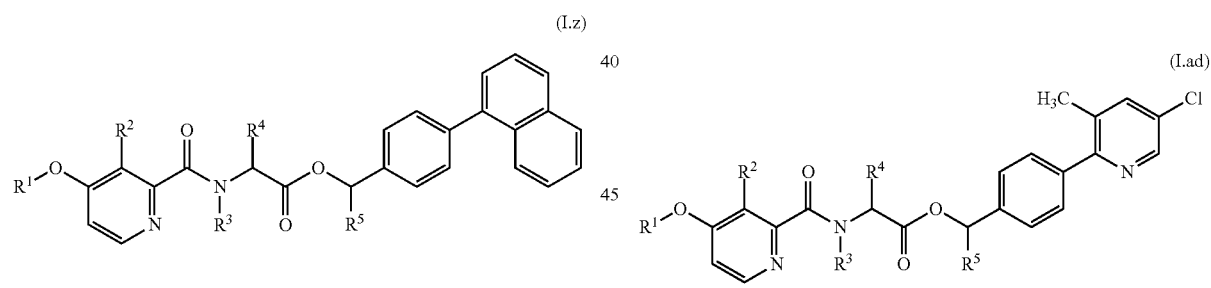

wherein $R^1$, $R^2$, $R^3$, $R^4$, and $R^5$ are as defined in Table 1.
aa) 126 Compounds of Formula (I.aa):

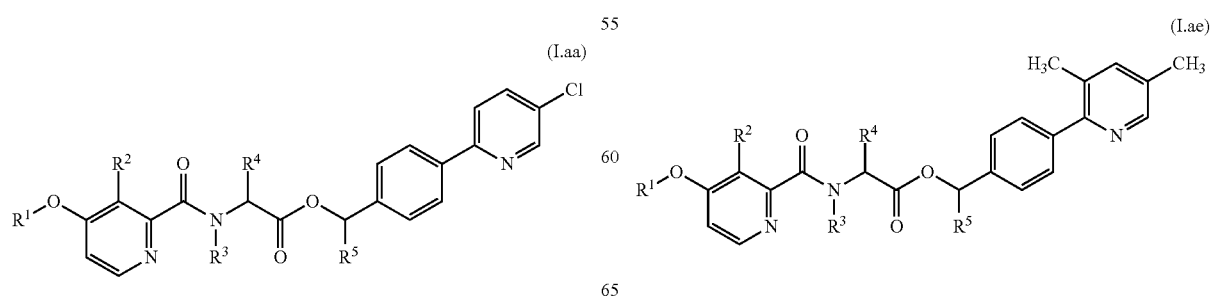

wherein $R^1$, $R^2$, $R^3$, $R^4$, and $R^5$ are as defined in Table 1.

ab) 126 Compounds of Formula (I.ab):

wherein $R^1$, $R^2$, $R^3$, $R^4$, and $R^5$ are as defined in Table 1.
ac) 126 Compounds of Formula (I.ac):

wherein $R^1$, $R^2$, $R^3$, $R^4$, and $R^5$ are as defined in Table 1.
ad) 126 Compounds of Formula (I.ad):

wherein $R^1$, $R^2$, $R^3$, $R^4$, and $R^5$ are as defined in Table 1.
ae) 126 Compounds of Formula (I.ae):

wherein $R^1$, $R^2$, $R^3$, $R^4$, and $R^5$ are as defined in Table 1.

af) 126 Compounds of Formula (I.af):

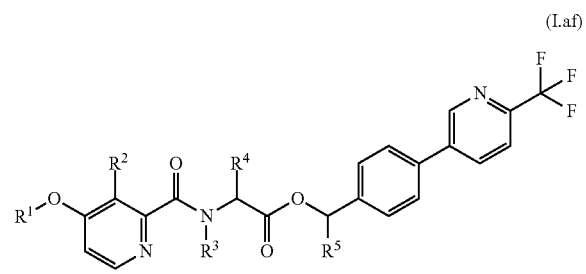

wherein $R^1$, $R^2$, $R^3$, $R^4$, and $R^5$ are as defined in Table 1.

ag) 126 Compounds of Formula (I.ag):

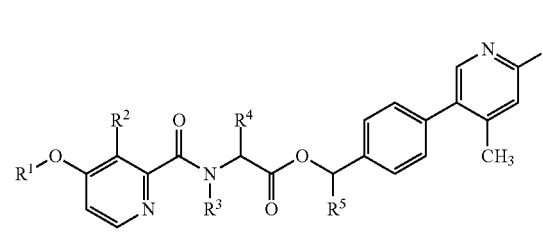

wherein $R^1$, $R^2$, $R^3$, $R^4$, and $R^5$ are as defined in Table 1.

ah) 126 Compounds of Formula (I.ah):

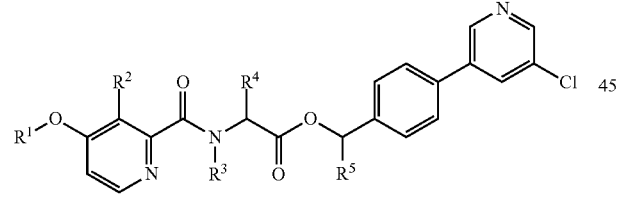

wherein $R^1$, $R^2$, $R^3$, $R^4$, and $R^5$ are as defined in Table 1.

ai) 126 Compounds of Formula (I.ai):

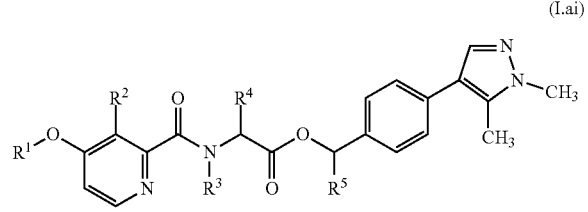

wherein $R^1$, $R^2$, $R^3$, $R^4$, and $R^5$ are as defined in Table 1.

aj) 126 Compounds of Formula (I.aj):

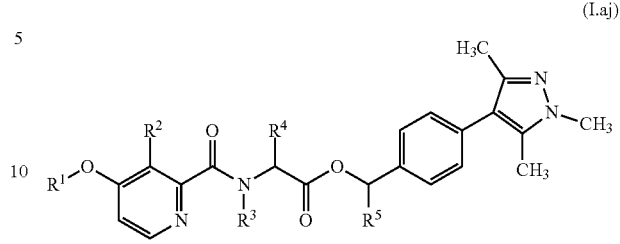

wherein $R^1$, $R^2$, $R^3$, $R^4$, and $R^5$ are as defined in Table 1.

ak) 126 Compounds of Formula (I.ak):

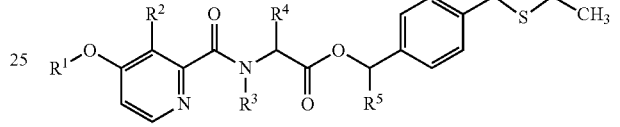

wherein $R^1$, $R^2$, $R^3$, $R^4$, and $R^5$ are as defined in Table 1.

am) 126 Compounds of Formula (I.am):

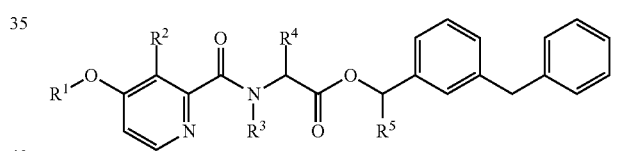

wherein $R^1$, $R^2$, $R^3$, $R^4$, and $R^5$ are as defined in Table 1.

an) 126 Compounds of Formula (Ian):

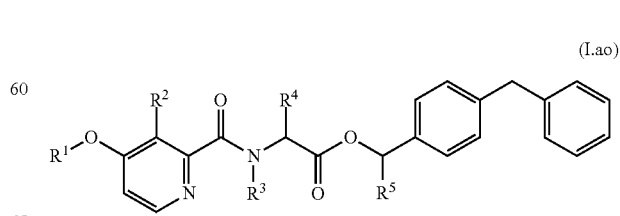

wherein $R^1$, $R^2$, $R^3$, $R^4$, and $R^5$ are as defined in Table 1.

ao) 126 Compounds of Formula (I.ao):

wherein $R^1$, $R^2$, $R^3$, $R^4$, and $R^5$ are as defined in Table 1.

ap) 126 Compounds of Formula (I.ap):

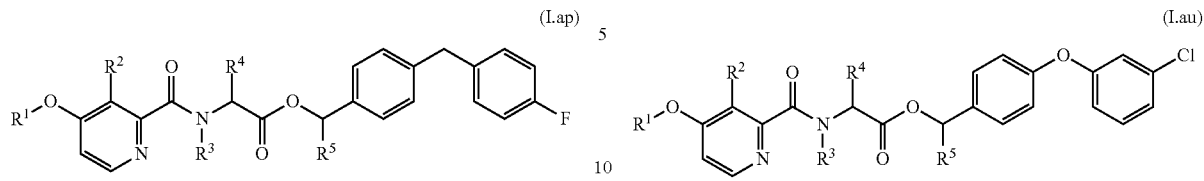
(I.ap)

wherein $R^1$, $R^2$, $R^3$, $R^4$, and $R^5$ are as defined in Table 1.

aq) 126 Compounds of Formula (I.aq):

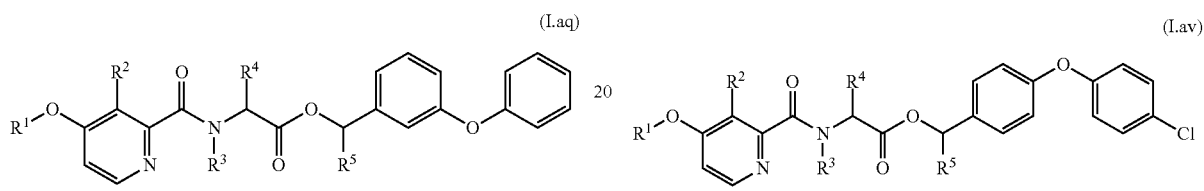
(I.aq)

wherein $R^1$, $R^2$, $R^3$, $R^4$, and $R^5$ are as defined in Table 1.

ar) 126 Compounds of Formula (I.ar):

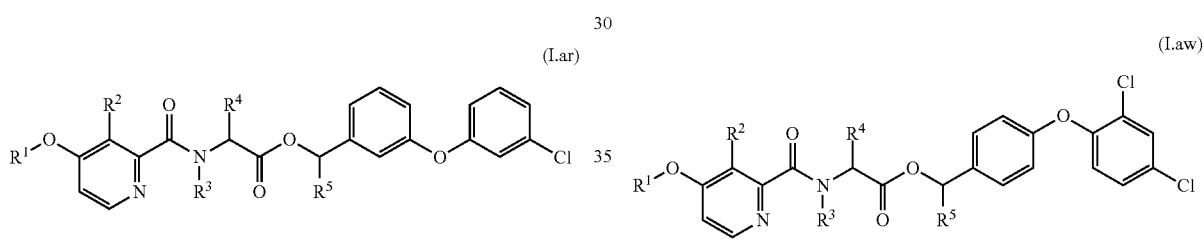
(I.ar)

wherein $R^1$, $R^2$, $R^3$, $R^4$, and $R^5$ are as defined in Table 1.

as) 126 Compounds of Formula (I.as):

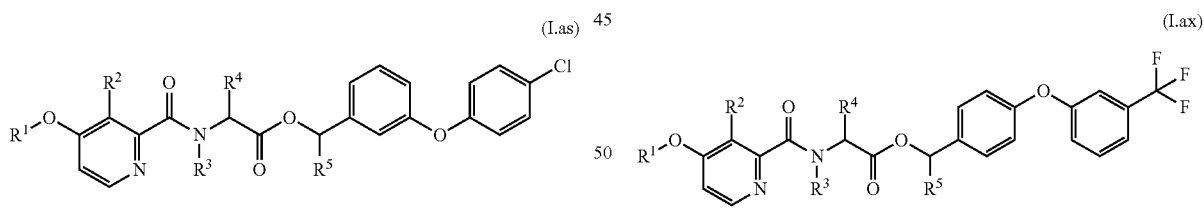
(I.as)

wherein $R^1$, $R^2$, $R^3$, $R^4$, and $R^5$ are as defined in Table 1.

at) 126 Compounds of Formula (I.at):

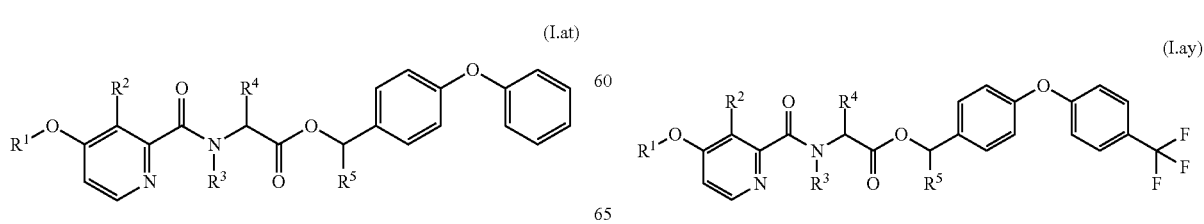
(I.at)

wherein $R^1$, $R^2$, $R^3$, $R^4$, and $R^5$ are as defined in Table 1.

au) 126 Compounds of Formula (I.au):

(I.au)

wherein $R^1$, $R^2$, $R^3$, $R^4$, and $R^5$ are as defined in Table 1.

av) 126 Compounds of Formula (.av):

(I.av)

wherein $R^1$, $R^2$, $R^3$, $R^4$, and $R^5$ are as defined in Table 1.

aw) 126 Compounds of Formula (I.aw):

(I.aw)

wherein $R^1$, $R^2$, $R^3$, $R^4$, and $R^5$ are as defined in Table 1.

ax) 126 Compounds of Formula (I.ax):

(I.ax)

wherein $R^1$, $R^2$, $R^3$, $R^4$, and $R^5$ are as defined in Table 1.

ay) 126 Compounds of Formula (I.ay):

(I.ay)

wherein $R^1$, $R^2$, $R^3$, $R^4$, and $R^5$ are as defined in Table 1.

az) 126 Compounds of Formula (I.az):

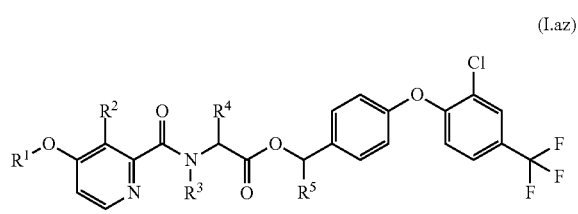

wherein $R^1$, $R^2$, $R^3$, $R^4$, and $R^5$ are as defined in Table 1.

ba) 126 Compounds of Formula (I.ba):

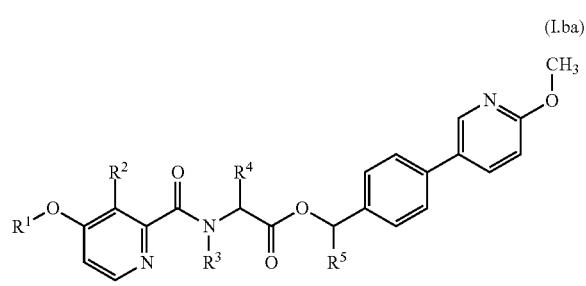

wherein $R^1$, $R^2$, $R^3$, $R^4$, and $R^5$ are as defined in Table 1.

bb) 126 Compounds of Formula (I.bb):

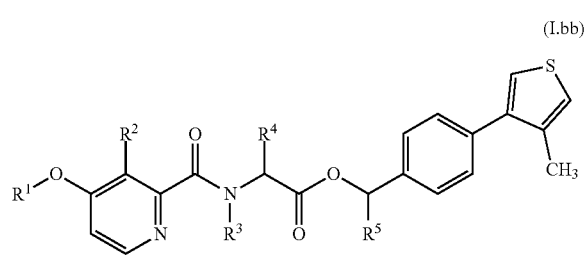

wherein $R^1$, $R^2$, $R^3$, $R^4$, and $R^5$ are as defined in Table 1.

Formulation Examples

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | 0) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |

-continued

| Suspension concentrate | |
|---|---|
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinyl alcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Compounds of formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

LIST OF ABBREVIATIONS

° C.=degrees Celsius
$CDCl_3$=chloroform-d
DMAP=4-dimethylaminopyridine
M=molar
m=multiplet
MHz=megahertz
PyBOP=benzotriazol-1-yl-oxytripyrrolidinophosphonium hexafluorophosphate
q=quartet
s=singlet Example 1: This example illustrates the preparation of [(1S)-1-[4-(o-tolyl)phenyl]ethyl] (2S)-2-[(3-hydroxy-4-methoxy-pyridine-2-carbonyl)amino]propanoate (Compound 1.h.001)

a) Preparation of (1S)-1-[4-(o-tolyl)phenyl]ethanol

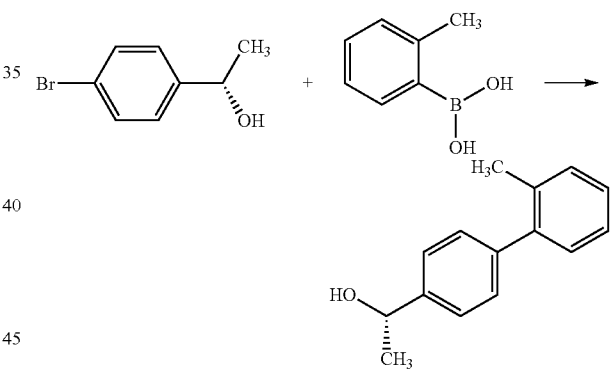

(S)-1-(4-Bromophenyl)ethanol (900 mg, 4.25 mmol, 1 equiv.) and 2-methylphenyl boronic acid (649 mg, 4.68 mmol, 1.1 equiv.) were dissolved in a mixture of 1,2-dimethoxyethane (22.4 mL) and water (11.2 mL) at room temperature. Potassium carbonate (3 g, 21.3 mmol, 5 equiv.), tri(o-tolyl)phosphine (92.5 mg, 0.298 mmol, 0.07 equiv.) and tetrakis(triphenylphosphine) palladium (355 mmol, 0.298 mmol, 0.07 equiv.) were added in sequence and the orange suspension was stirred for 90 minutes at 80° C. After consumption of the starting material, the reaction was cooled to room temperature, diluted with water and extracted with ethyl acetate. The combined organic phases were washed with water and brine, dried over sodium sulfate and the solvent was removed under vacuum.

Column chromatography on silica gel (cyclohexene/ethylacetate) afforded the desired (1S)-1-[4-(o-tolyl)phenyl]ethanol as a yellow oil (640 mg, 3.02 mmol, 71% yield). $^1$H-NMR (400 MHz, $CDCl_3$): δ=7.52-7.20 (m, 8H), 5.05-4.95 (m, 1H), 2.30 (s, 3H), 1.83 (d, 1H), 1.60 (d, 3H).

b) Preparation of [(1S)-1-[4-(o-tolyl)phenyl]ethyl] (2S)-2-(tert-butoxycarbonylamino)propanoate

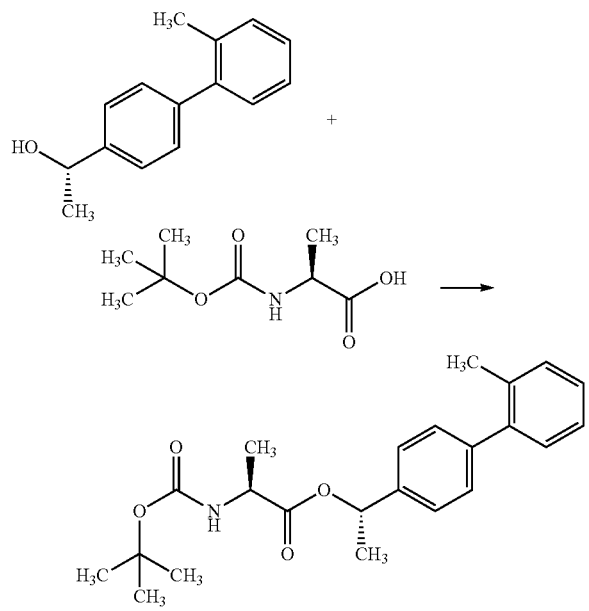

(2S)-2-(tert-butoxycarbonylamino)propanoic acid (627 mg, 3.316 mmol, 1.1 equiv.), DMAP (37 mg, 0.302 mmol, 0.1 equiv.) and N-(3-dimethylaminopropyl)-N'-ethylcarbodiimide hydrochloride (1.179 g, 6.029 mmol, 2 equiv.) were added in sequence to a stirred solution of (1S)-1-[4-(o-tolyl) phenyl]ethanol (640 mg, 3.02 mmol, 1 equiv.) in dichloromethane (22.6 mL) at 0° C. The reaction was allowed to reach room temperature and was further stirred for 16 hours. Then the mixture was diluted with dichloromethane and washed twice with an aqueous NaHCO₃ saturated solution. The organic phase was further washed with water and then dried over sodium sulfate. Removal of the volatiles by rotatory evaporation provided the desired product [(1S)-1-[4-(o-tolyl)phenyl]ethyl] (2S)-2-(tert-butoxycarbonylamino)propanoate (1.17 g, 3.02 mmol, quantitative yield). The compound was used in the next step without any further purification. ¹H-NMR (400 MHz, CDCl₃): δ=7.48-7.20 (m, 8H), 6.02-5.95 (q, 1H), 5.10-5.00 (m, 1H), 4.45-4.35 (m, 1H), 2.30 (s, 3H), 1.63 (d, 3H), 1.47 (s, 9H), 1.40 (d, 3H).

c) Preparation of [(1S)-1-[4-(o-tolyl)phenyl]ethyl] (2S)-2-[(3-hydroxy-4-methoxy-pyridine-2-carbonyl) amino]propanoate (Compound 1.h.001)

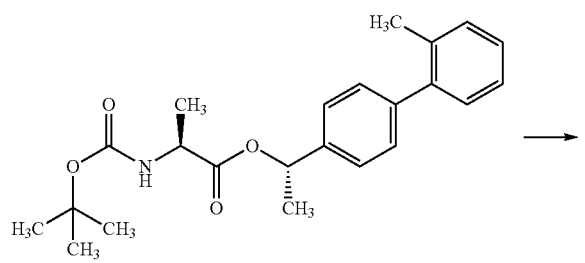

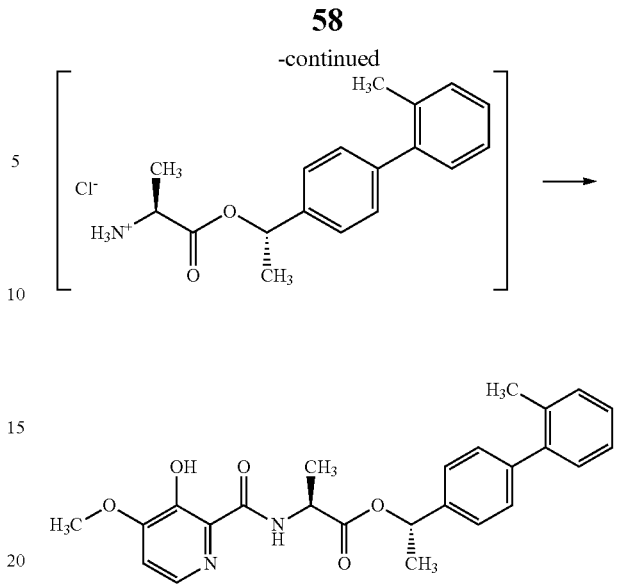

A 4M HCl solution in dioxane (7.6 mL, 30.2 mmol, 10 equiv.) was slowly added to a stirred solution of [(1S)-1-[4-(o-tolyl)phenyl]ethyl] (2S)-2-(tert-butoxycarbonylamino) propanoate (1.17 g, 3.02 mmol, 1 equiv.) in dichloromethane (15.1 mL). The reaction was stirred at room temperature for 4.5 h and then the solvent was removed under vacuum. The intermediate hydrochloride was obtained in quantitative yield (1.02 g, 3.02 mmol) and directly employed in the following amidation reaction.

N,N-diisopropylethylamine (0.57 mL, 3.30 mmol, 3.3 equiv.) was added to a stirred solution of [(1S)-1-methyl-2-[(1S)-1-[4-(o-tolyl)phenyl]ethoxy]-2-oxo-ethyl]ammonium chloride (337 mg, 1.00 mmol, 1 equiv.) in dichloromethane (10 mL). Then 3-hydroxy-4-methoxy-pyridine-2-carboxylic acid (186 mg, 1.1 mmol, 1.1 equiv.) and PyBOP (584 mg, 1.1 mmol, 1.1 equiv.) were added in sequence and the reaction was stirred at room temperature for 1 hour. The mixture was diluted with dichloromethane, washed with an aqueous NaHCO₃ saturated solution, water and brine and the organic phase was eventually dried over sodium sulfate. Evaporation of the solvent and purification by column chromatography on silica gel afforded the desired [(1S)-1-[4-(o-tolyl)phenyl]ethyl] (2S)-2-[(3-hydroxy-4-methoxy-pyridine-2-carbonyl)amino]propanoate (Compound 1.h.001, 140 mg, 0.32 mmol, 32% yield). ¹H-NMR (400 MHz, CDCl₃): δ=12.13 (s, 1H), 8.52 (d, 1H), 8.00 (d, 1H), 7.48-7.15 (m, 8H), 6.88 (d, 1H), 6.04 (q, 1H), 4.80 (m, 1H), 3.97 (s, 3H), 2.28 (s, 3H), 1.69 (d, 3H), 1.60 (d, 3H).

Throughout this description, temperatures are given in degrees Celsius (° C.) and "m.p." means melting point. LC/MS means Liquid Chromatography Mass Spectrometry and the description of the apparatus and the method is: (ACQUITY UPLC from Waters, Phenomenex Gemini C18, 3 μm particle size, 110 Angström, 30×3 mm column, 1.7 mL/min., 60° C., H₂O+0.05% HCOOH (95%)/CH₃CN/ MeOH 4:1+0.04% HCOOH (5%)–2 min.–CH₃CN/MeOH 4:1+0.04% HCOOH (5%)–0.8 min., ACQUITY SQD Mass Spectrometer from Waters, ionization method: electrospray (ESI), Polarity: positive ions, Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700)).

TABLE 2

Melting point and LC/MS data (Rt = Retention time) for selected compounds of Table 1

| No. | Compound Name | Structure | Mp (° C.) | LC/MS |
|---|---|---|---|---|
| I.a.001 | [(1S)-1-(3-phenylphenyl)ethyl] (2S)-2-[(3-hydroxy-4-methoxy-pyridine-2-carbonyl)amino] propanoate | 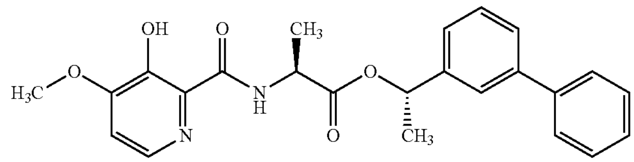 [SMILES: COc1ccnc(C(=O)N[C@@H](C)C(=O)O[C@@H](C)c2cccc(-c3ccccc3)c2)c1O] | | Rt = 1.81 min; MS: m/z = 422 (M + 1) |
| I.b.001 | [(1S)-1-[3-(2-chlorophenyl)phenyl]ethyl] (2S)-2-[(3-hydroxy-4-methoxy-pyridine-2-carbonyl)amino] propanoate | 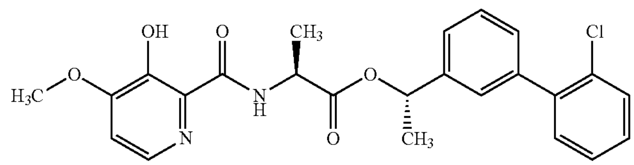 [SMILES: COc1ccnc(C(=O)N[C@@H](C)C(=O)O[C@@H](C)c2cccc(-c3ccccc3Cl)c2)c1O] | | Rt = 1.90 min; MS: m/z = 455 (M + 1) |
| I.d.001 | [(1S)-1-(4-phenylphenyl)ethyl] (2S)-2-[(3-hydroxy-4-methoxy-pyridine-2-carbonyl)amino] propanoate | 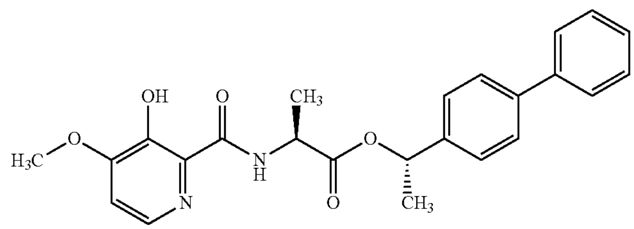 [SMILES: COc1ccnc(C(=O)N[C@@H](C)C(=O)O[C@@H](C)c2ccc(-c3ccccc3)cc2)c1O] | | Rt = 1.85 min; MS: m/z = 421 (M + 1) |
| I.d.019 | [(1S)-1-(4-phenylphenyl)ethyl] (2S)-2-[(3-acetoxy-4-methoxy-pyridine-2-carbonyl)amino] propanoate | 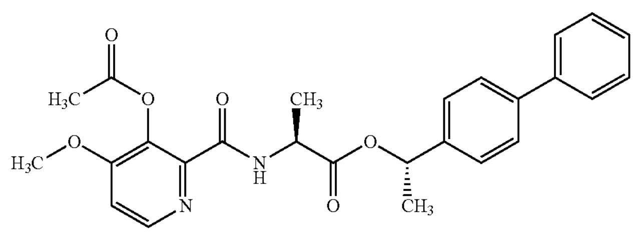 [SMILES: COc1ccnc(C(=O)N[C@@H](C)C(=O)O[C@@H](C)c2ccc(-c3ccccc3)cc2)c1OC(C)=O] | | Rt = 1.87 min; MS: m/z = 463 (M + 1) |
| I.e.001 | [(1S)-1-(3-fluoro-4-phenyl-phenyl)ethyl] (2S)-2-[(3-hydroxy-4-methoxy-pyridine-2-carbonyl)amino] propanoate | 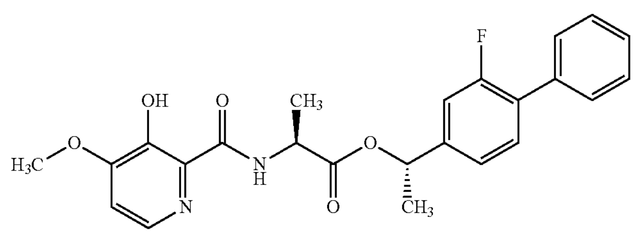 [SMILES: COc1ccnc(C(=O)N[C@@H](C)C(=O)O[C@@H](C)c2ccc(-c3ccccc3)c(F)c2)c1O] | | Rt = 1.13 min; MS: m/z = 439 (M + 1) |
| I.h.001 | [(1S)-1-[4-(o-tolyl)phenyl]ethyl] (2S)-2-[(3-hydroxy-4-methoxy-pyridine-2-carbonyl)amino] propanoate | 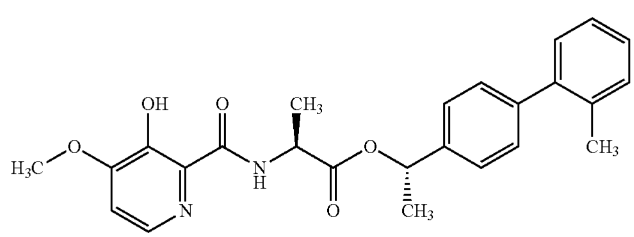 [SMILES: COc1ccnc(C(=O)N[C@@H](C)C(=O)O[C@@H](C)c2ccc(-c3ccccc3C)cc2)c1O] | | Rt = 2.00 min; MS: m/z = 435 (M + 1) |
| I.i.001 | [(1S)-1-[4-(2-ethylphenyl)phenyl]ethyl] (2S)-2-[(3-hydroxy-4-methoxy-pyridine-2-carbonyl)amino] propanoate | 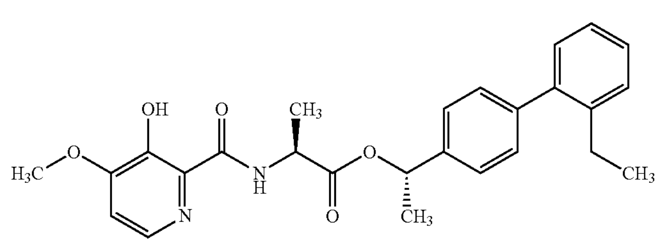 [SMILES: CCc1ccccc1-c1ccc([C@H](C)OC(=O)[C@H](C)NC(=O)c2nccc(OC)c2O)cc1] | | Rt = 1.23 min; MS: m/z = 449 (M + 1) |

TABLE 2-continued

Melting point and LC/MS data (Rt = Retention time) for selected compounds of Table 1

| No. | Compound Name | Structure | Mp (° C.) | LC/MS |
|---|---|---|---|---|
| I.j.001 | [(1S)-1-[4-(2-isopropylphenyl)phenyl]ethyl] (2S)-2-[(3-hydroxy-4-methoxy-pyridine-2-carbonyl)amino]propanoate | 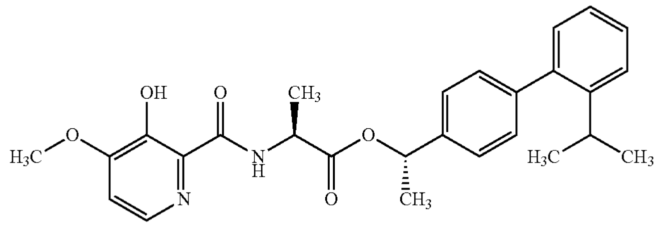 [SMILES: COc1ccnc(C(=O)N[C@@H](C)C(=O)O[C@@H](C)c2ccc(-c3ccccc3C(C)C)cc2)c1O] | | Rt = 1.26 min; MS: m/z = 463 (M + 1) |
| I.k.001 | [(1S)-1-[4-[2-(tert-butoxymethyl)phenyl]phenyl]ethyl] (2S)-2-[(3-hydroxy-4-methoxy-pyridine-2-carbonyl)amino]propanoate | 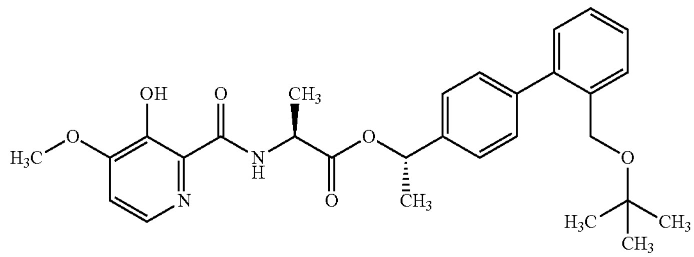 [SMILES: COc1ccnc(C(=O)N[C@@H](C)C(=O)O[C@@H](C)c2ccc(-c3ccccc3COC(C)(C)C)cc2)c1O] | | Rt = 1.25 min; MS: m/z = 507 (M + 1) |
| I.m.001 | [(1S)-1-[4-(2,3-dimethylphenyl)phenyl]ethyl] (2S)-2-[(3-hydroxy-4-methoxy-pyridine-2-carbonyl)amino]propanoate | 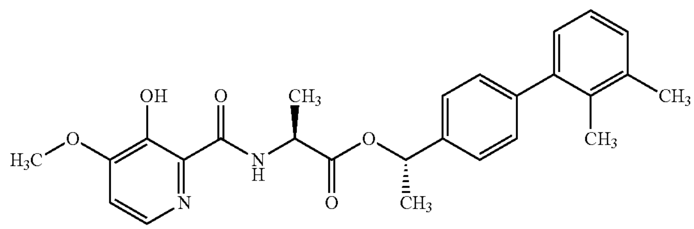 | | Rt = 2.08 min; MS: m/z = 449 (M + 1) |
| I.n.001 | [(1S)-1-[4-(4-chloro-2-methyl-phenyl)phenyl]ethyl] (2S)-2-[(3-hydroxy-4-methoxy-pyridine-2-carbonyl)amino]propanoate | 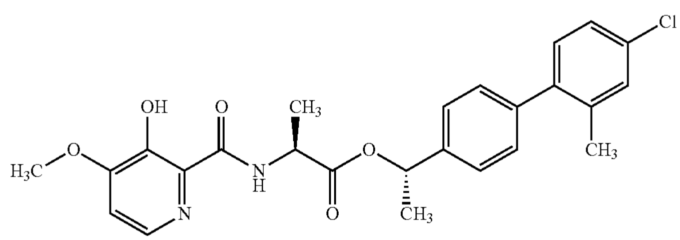 [SMILES: COc1ccnc(C(=O)N[C@@H](C)C(=O)O[C@@H](C)c2ccc(-c3ccc(Cl)cc3C)cc2)c1O] | | Rt = 2.16 min; MS: m/z = 469 (M + 1) |
| I.p.001 | [(1S)-1-[4-(2,5-dimethylphenyl)phenyl]ethyl] (2S)-2-[(3-hydroxy-4-methoxy-pyridine-2-carbonyl)amino]propanoate | 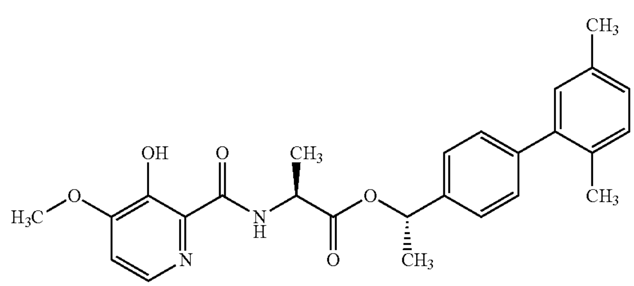 [SMILES: COc1ccnc(C(=O)N[C@@H](C)C(=O)O[C@@H](C)c2ccc(-c3cc(C)ccc3C)cc2)c1O] | | Rt = 1.23 min; MS: m/z = 450 (M + 1) |
| I.r.001 | [(1SS)-1-[4-(3-chlorophenyl)phenyl]ethyl] (2S)-2-[(3-hydroxy-4-methoxy-pyridine-2-carbonyl)amino]propanoate | 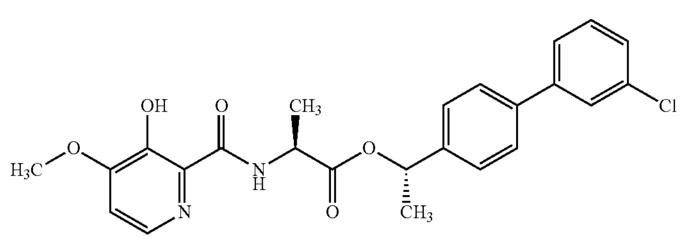 [SMILES: COc1ccnc(C(=O)N[C@@H](C)C(=O)O[C@@H](C)c2ccc(-c3cccc(Cl)c3)cc2)c1O] | | Rt = 1.20 min; MS: m/z = 455 (M + 1) |

TABLE 2-continued

Melting point and LC/MS data (Rt = Retention time) for selected compounds of Table 1

| Compound No. | Name | Structure | Mp (° C.) | LC/MS |
|---|---|---|---|---|
| I.u.001 | [(1S)-1-[4-(4-chlorophenyl)phenyl]ethyl] (2S)-2-[(3-hydroxy-4-methoxy-pyridine-2-carbonyl)amino]propanoate | 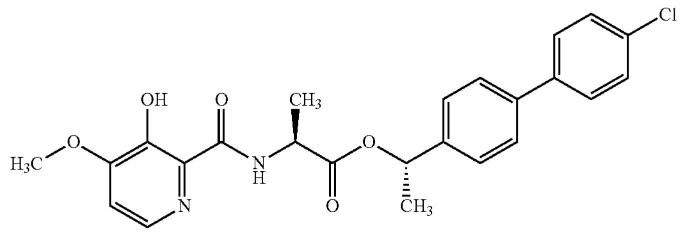 | | Rt = 1.20 min; MS: m/z = 455 (M + 1) |
| I.v.001 | [(1S)-1-[4-(4-bromophenyl)phenyl]ethyl] (2S)-2-[(3-hydroxy-4-methoxy-pyridine-2-carbonyl)amino]propanoate | 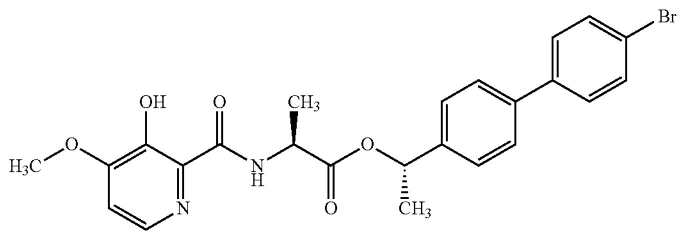 | | Rt = 2.04 min; MS: m/z = 500 (M + 1) |
| I.v.019 | [(1S)-1-[4-(4-bromophenyl)phenyl]ethyl] (2S)-2-[(3-acetoxy-4-methoxy-pyridine-2-carbonyl)amino]propanoate | 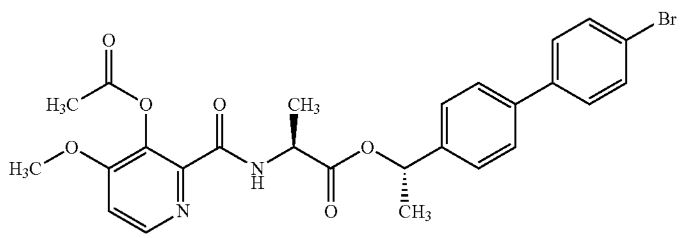 [SMILES: COc1ccnc(C(=O)N[C@@H](C)C(=O)O[C@@H](C)c2ccc(-c3ccc(Br)cc3)cc2)c1OC(C)=O] | | Rt = 2.04 min; MS: m/z = 543 (M + 1) |
| I.w.001 | [(1S)-1-[4-(p-tolyl)phenyl]ethyl] (2S)-2-[(3-hydroxy-4-methoxy-pyridine-2-carbonyl)amino]propanoate | 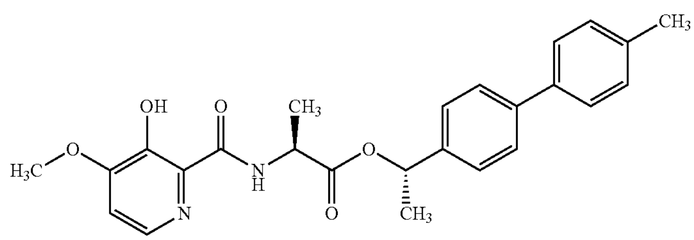 | | Rt = 1.19 min; MS: m/z = 435 (M + 1) |
| I.x.001 | [(1S)-1-[4-[4-(trifluoromethyl)phenyl]phenyl]ethyl] (2S)-2-[(3-hydroxy-4-methoxy-pyridine-2-carbonyl)amino]propanoate | 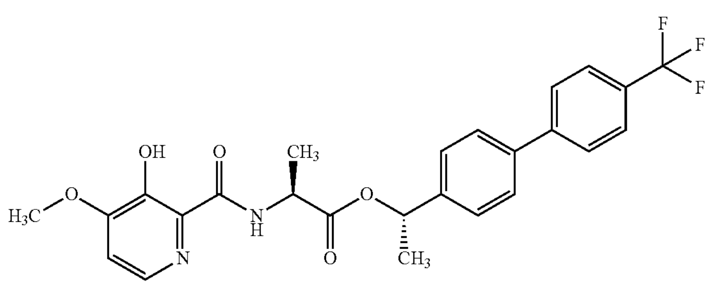 [SMILES: COc1ccnc(C(=O)N[C@@H](C)C(=O)O[C@@H](C)c2ccc(-c3ccc(C(F)(F)F)cc3)cc2)c1O] | | Rt = 1.21 min; MS: m/z = 489 (M + 1) |
| I.y.001 | [(1S)-1-[4-(4-chloro-3-methyl-phenyl)phenyl]ethyl] (2S)-2-[(3-hydroxy-4-methoxy-pyridine-2-carbonyl)amino]propanoate | 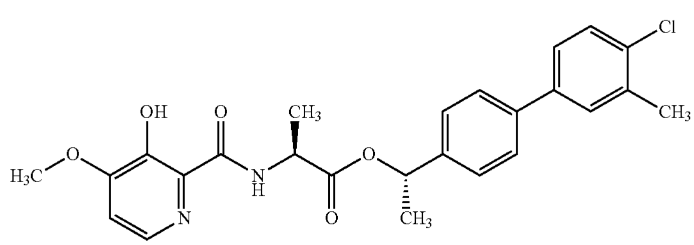 | | Rt = 1.26 min; MS: m/z = 469 (M + 1) |

TABLE 2-continued

Melting point and LC/MS data (Rt = Retention time) for selected compounds of Table 1

| No. | Compound Name | Structure | Mp (° C.) | LC/MS |
|---|---|---|---|---|
| I.z.001 | [(1S)-1-[4-(1-naphthyl)phenyl]ethyl] (2S)-2-[(3-hydroxy-4-methoxy-pyridine-2-carbonyl)amino] propanoate | 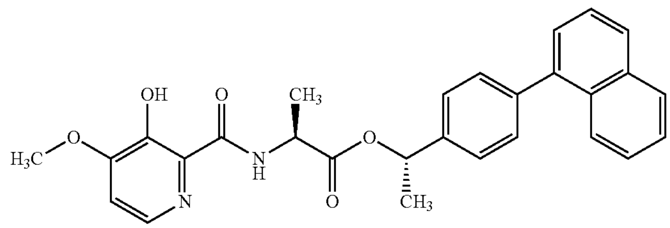 [SMILES: COc1ccnc(C(=O)N[C@@H](C)C(=O)O[C@@H](C)c2ccc(-c3cccc4ccccc34)cc2)c1O] | | Rt = 1.23 min; MS: m/z = 471 (M + 1) |
| I.aa.001 | [(1S)-1-[4-(5-chloro-2-pyridyl)phenyl]ethyl] (2S)-2-[(3-hydroxy-4-methoxy-pyridine-2-carbonyl)amino] propanoate | 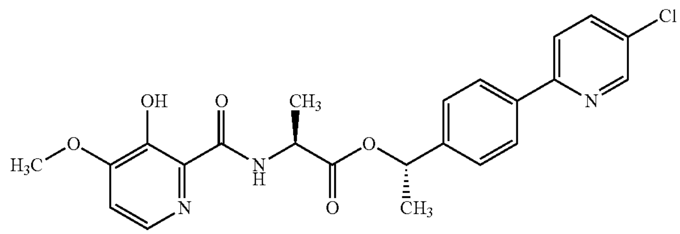 | 144-145 | Rt = 1.76 min; MS: m/z = 454 (M + 1) |
| I.af.001 | [(1S)-1-[4-[6-(trifluoromethyl)-3-pyridyl]phenyl]ethyl] (2S)-2-[(3-hydroxy-4-methoxy-pyridine-2-carbonyl)amino] propanoate | 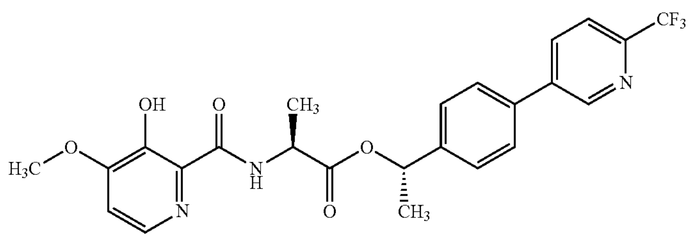 [SMILES: COc1ccnc(C(=O)N[C@@H](C)C(=O)O[C@@H](C)c2ccc(-c3ccc(C(F)(F)F)nc3)cc2)c1O] | | Rt = 1.76 min; MS: m/z = 490 (M + 1) |
| I.ah.001 | [(1S)-1-[4-(5-chloro-3-pyridyl)phenyl]ethyl] (2S)-2-[(3-hydroxy-4-methoxy-pyridine-2-carbonyl)amino] propanoate | 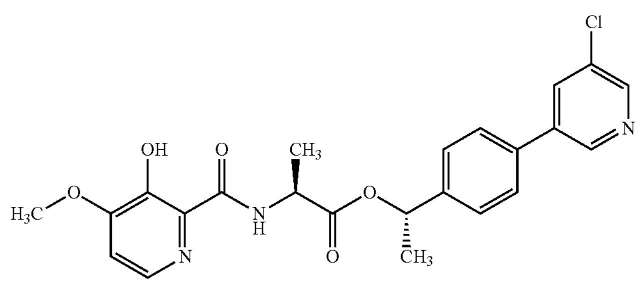 [SMILES: COc1ccnc(C(=O)N[C@@H](C)C(=O)O[C@@H](C)c2ccc(-c3cncc(Cl)c3)cc2)c1O] | | Rt = 1.63 min; MS: m/z = 454 (M + 1) |
| I.aq.001 | [(1S)-1-(3-phenoxyphenyl)ethyl] (2S)-2-[(3-hydroxy-4-methoxy-pyridine-2-carbonyl)amino] propanoate | 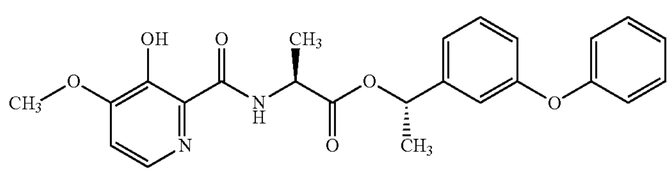 [SMILES: COc1ccnc(C(=O)N[C@@H](C)C(=O)O[C@@H](C)c2cccc(Oc3ccccc3)c2)c1O] | | Rt = 1.13 min; MS: m/z = 437 (M + 1) |
| I.ar.001 | [(1S)-1-[3-(3-chlorophenoxy)phenyl] ethyl] (2S)-2-[(3-hydroxy-4-methoxy-pyridine-2-carbonyl)amino] propanoate | 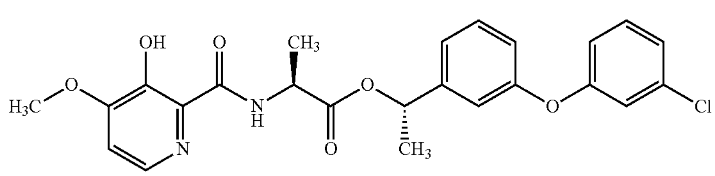 [SMILES: COc1ccnc(C(=O)N[C@@H](C)C(=O)O[C@@H](C)c2cccc(Oc3cccc(Cl)c3)c2)c1O] | | Rt = 1.19 min; MS: m/z = 471 (M + 1) |
| I.as.001 | [(1S)-1-[3-(4-chlorophenoxy)phenyl] ethyl] (2S)-2-[(3-hydroxy-4-methoxy-pyridine-2-carbonyl)amino] propanoate | 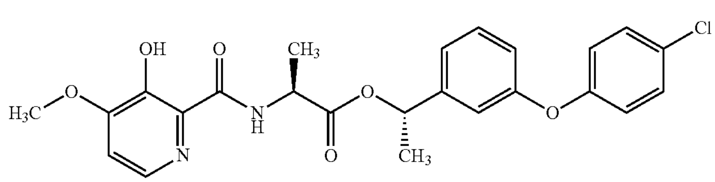 [SMILES: COc1ccnc(C(=O)N[C@@H](C)C(=O)O[C@@H](C)c2cccc(Oc3ccc(Cl)cc3)c2)c1O] | | Rt = 1.19 min; MS: m/z = 471 (M + 1) |

TABLE 2-continued

Melting point and LC/MS data (Rt = Retention time) for selected compounds of Table 1

| Compound No. | Name | Structure | Mp (° C.) | LC/MS |
|---|---|---|---|---|
| I.at.001 | [(1S)-1-(4-phenoxyphenyl)ethyl] (2S)-2-[(3-hydroxy-4-methoxy-pyridine-2-carbonyl)amino] propanoate | 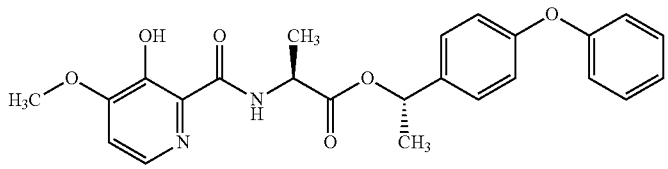 [SMILES: COc1ccnc(C(=O)N[C@@H](C)C(=O)O[C@@H](C)c2ccc(Oc3ccccc3)cc2)c1O] | | Rt = 1.85 min; MS: m/z = 437 (M + 1) |
| I.au.001 | [(1S)-1-[4-(3-chlorophenoxy)phenyl]ethyl] (2S)-2-[(3-hydroxy-4-methoxy-pyridine-2-carbonyl)amino] propanoate | 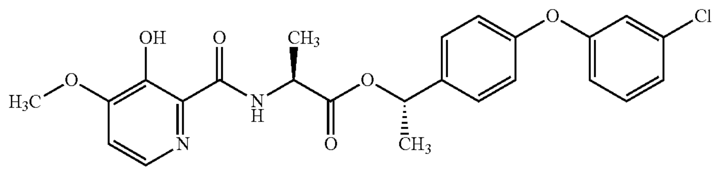 [SMILES: COc1ccnc(C(=O)N[C@@H](C)C(=O)O[C@@H](C)c2ccc(Oc3cccc(Cl)c3)cc2)c1O] | | Rt = 1.20 min; MS: m/z = 471 (M + 1) |
| I.av.001 | [(1S)-1-[4-(4-chlorophenoxy)phenyl]ethyl] (2S)-2-[(3-hydroxy-4-methoxy-pyridine-2-carbonyl)amino] propanoate | 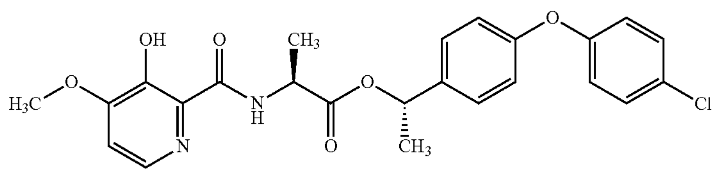 [SMILES: COc1ccnc(C(=O)N[C@@H](C)C(=O)O[C@@H](C)c2ccc(Oc3ccc(Cl)cc3)cc2)c1O] | | Rt = 2.01 min; MS: m/z = 471 (M + 1) |
| I.aw.001 | [(1S)-1-[4-(2,4-dichlorophenoxy)phenyl]ethyl] (2S)-2-[(3-hydroxy-4-methoxy-pyridine-2-carbonyl)amino] propanoate | 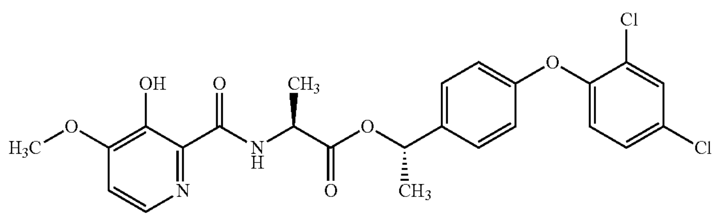 [SMILES: COc1ccnc(C(=O)N[C@@H](C)C(=O)O[C@@H](C)c2ccc(Oc3ccc(Cl)cc3Cl)cc2)c1O] | | Rt = 2.12 min; MS: m/z = 507 (M + 1) |
| I.ax.001 | [(1S)-1-[4-[3-(trifluoromethyl)phenoxy]phenyl]ethyl] (2S)-2-[(3-hydroxy-4-methoxy-pyridine-2-carbonyl)amino] propanoate | 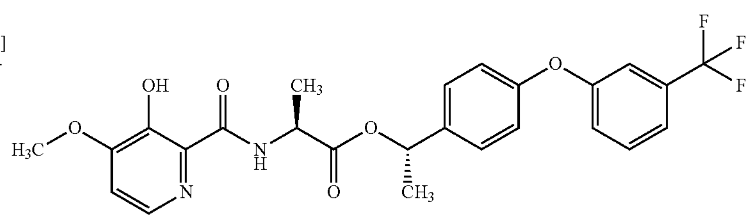 | | Rt = 2.05 min; MS: m/z = 505 (M + 1) |
| I.ay.001 | [(1S)-1-[4-[4-(trifluoromethyl)phenoxy]phenyl]ethyl] (2S)-2-[(3-hydroxy-4-methoxy-pyridine-2-carbonyl)amino] propanoate | 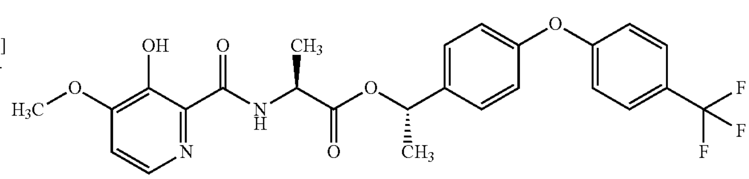 | | Rt = 1.21 min; MS: m/z = 505 (M + 1) |
| I.az.001 | [(1S)-1-[4-[2-chloro-4-(trifluoromethyl)phenoxy]phenyl]ethyl] (2S)-2-[(3-hydroxy-4-methoxy-pyridine-2-carbonyl)amino] propanoate | 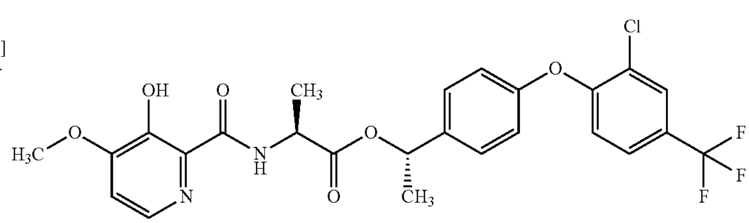 | | Rt = 2.16 min; MS: m/z = 539 (M + 1) |

TABLE 2-continued

Melting point and LC/MS data (Rt = Retention time) for selected compounds of Table 1

| Compound No. | Compound Name | Structure | Mp (° C.) | LC/MS |
|---|---|---|---|---|
| I.ba.001 | [(1S)-1-[4-(2-methoxy-4-pyridyl)phenyl]ethyl] (2S)-2-[(3-hydroxy-4-methoxy-pyridine-2-carbonyl)amino] propanoate | 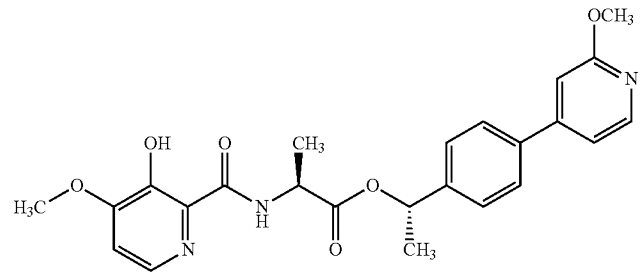 [SMILES: COc1cc(-c2ccc([C@H](C)OC(=O)[C@H](C)NC(=O)c3nccc(OC)c3O)cc2)ccn1] | | Rt = 1.64 min; MS: m/z = 452 (M + 1) |
| I.bb.001 | [(1S)-1-[4-(4-methyl-3-thienyl)phneyl]ethyl] (2S)-2-[(3-hydroxy-4-methoxy-pyridine-2-carbonyl)amino] propanoate | 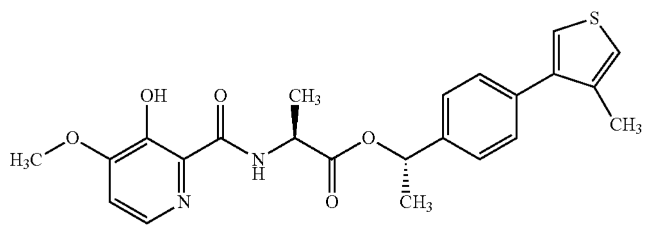 [SMILES: COc1ccnc(C(=O)N[C@@H](C)C(=O)O[C@@H](C)c2ccc(-c3cscc3C)cc2)c1O] | | Rt = 1.88 min; MS: m/z = 441 (M + 1) |

Biological Examples

*Botryotinia fuckeliana* (*Botrvtis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

Compounds I.a.001, I.b.001, I.d.001, I.e.001, I.h.001, I.k.001, I.m.001, I.n.001, I.p.001, I.r.001, I.u.001, I.v.001, I.x.001, I.z.001, I.aq.001 and I.as.001 at 200 ppm in the formulation give at least 80% disease control in this test when compared to untreated control leaf disks under the same conditions, which show extensive disease development.

*Glomerella lagenarium* (*Colletotrichum lagenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3 to 4 days after application.

Compounds I.a.001, I.d.001, I.e.001, I.h.001, I.i.001, I.j.001, I.k.001, I.m.001, I.n.001, I.p.001, I.r.001, I.u.001, I.v.001, I.w.001, I.x.001, I.y.001, I.z.001, I.aa.001, I.ah.001, I.af.001, I.aq.001, I.as.001, I.ar.001, I.at.001, I.au.001, I.av.001, I.aw.001, I.ax.001, I.ay.001, I.az.001, I.ba.001 and I.bb.001 at 200 ppm in the formulation give at least 80% disease control in this test when compared to untreated control leaf disks under the same conditions, which show extensive disease development.

*Magnaporthe grisea* (*Pyricularia oryzae*)/Rice/Leaf Disc Preventative (Rice Blast)

Rice leaf segments cv. Ballila are placed on agar in a multiwell plate (24-well format) and sprayed with the test compound formulated with DMSO and Tween20 and diluted in water. The leaf segments are inoculated with a spore suspension of the fungus 2 days after application. The inoculated leaf segments are incubated at 22° C. and 80% rh under a light regime of 24 h darkness followed by 12 h light/12 h darkness in a climate cabinet and the activity of a compound is assessed as percent disease control compared to untreated when an appropriate level of disease damage appears in untreated check leaf segments (5 to 7 days after application).

Compounds I.i.001, I.m.001, I.p.001, I.v.019, I.av.001 and I.ax.001 at 200 ppm in the formulation give at least 80% disease control in this test when compared to untreated control leaf disks under the same conditions, which show extensive disease development.

*Monographella nivalis* (*Microdochium nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.a.001, I.b.001, I.d.001, I.e.001, I.h.001, I.j.001, I.m.001, I.n.001, I.r.001, I.u.001, I.v.001, I.v.019, I.w.001, I.x.001, I.aa.001, I.ah.001, I.af.001, I.at.001, I.au.001, I.av.001, I.ay.001 and I.ba.001 and I.bb.001 at 200 ppm in the formulation give at least 80% disease control in this test when compared to untreated control leaf disks under the same conditions, which show extensive disease development.

*Mycosphaerella arachidis* (*Cercospora arachidicola*)/Liquid Culture (Early Leaf Spot)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.a.001, I.b.001, I.d.001, I.e.001, I.h.001, I.i.001, I.j.001, I.k.001, I.m.001, I.n.001, I.p.001, I.r.001, I.u.001, I.v.001, I.v.019, I.w.001, I.x.001, I.y.001, I.z.001, I.aa.001, I.ah.001, I.af.001, I.ar.001, I.as.001, I.at.001, I.au.001, I.av.001, I.aw.001, I.ax.001, I.ay.001, I.az.001 and I.ba.001 and I.bb.001 at 200 ppm in the formulation give at least 80% disease control in this test when compared to untreated control leaf disks under the same conditions, which show extensive disease development.

*Mycosphaerella graminicola* (*Septoria tritici*)/Liquid Culture (*Septoria* Blotch)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4 to 5 days after application.

Compounds I.a.001, I.b.001, I.d.001, I.d.019, I.e.001, I.h.001, I.i.001, I.j.001, I.k.001, I.m.001, I.n.001, I.p.001, I.r.001, I.u.001, I.v.001, I.v.019, I.w.001, I.x.001, I.y.001, I.z.001, I.aa.001, I.ah.001, I.af.001, I.aq.001, I.ar.001, I.as.001, I.at.001, I.au.001, I.av.001, I.aw.001, I.ax.001, I.ay.001, I.az.001 and I.ba.001 and I.bb.001 at 200 ppm in the formulation give at least 80% disease control in this test when compared to untreated control leaf disks under the same conditions, which show extensive disease development.

*Phaeosphaeria nodorum* (*Septoria nodorum*)/Wheat/Leaf Disc Preventative (Glume Blotch)

Wheat leaf segments cv. Kanzler are placed on agar in a multiwell plate (24-well format) and sprayed with the formulated test compound diluted in water. The leaf disks are inoculated with a spore suspension of the fungus 2 days after application. The inoculated test leaf disks are incubated at 20° C. and 75% rh under a light regime of 12 h light/12 h darkness in a climate cabinet and the activity of a compound is assessed as percent disease control compared to untreated when an appropriate level of disease damage appears in untreated check leaf disks (5-7 days after application).

Compounds I.d.019, I.h.001, I.i.001, I.k.001, I.m.001, I.n.001, I.v.001, I.v.019, I.w.001, Iaq.001, I.aw.001, I.ax.001, I.ay.001, I.az.001 and I.ba.001 at 200 ppm in the formulation give at least 80% disease control in this test when compared to untreated control leaf disks under the same conditions, which show extensive disease development.

*Puccinia recondita* f. sp. *tritici*/Wheat/Leaf Disc Preventative (Brown Rust)

Wheat leaf segments cv. Kanzler are placed on agar in multiwell plates (24-well format) and sprayed with the formulated test compound diluted in water. The leaf disks are inoculated with a spore suspension of the fungus 1 day after application. The inoculated leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (7-9 days after application).

Compounds I.b.001, I.d.001, I.d.019, I.e.001, I.h.001, I.i.001, I.j.001, I.k.001, I.m.001, I.n.001, I.p.001, I.r.001, I.u.001, I.v.001, I.v.019, I.w.001, I.x.001, I.y.001, I.z.001, I.aa.001, I.ah.001, I.af.001, I.aq.001, I.ar.001, I.as.001, I.at.001, I.au.001, I.av.001, I.aw.001, I.ax.001, I.ay.001 and I.ba.001 and I.bb.001 at 200 ppm in the formulation give at least 80% disease control in this test when compared to untreated c control leaf disks under the same conditions, which show extensive disease development.

The invention claimed is:

1. A compound of formula (I):

(I)

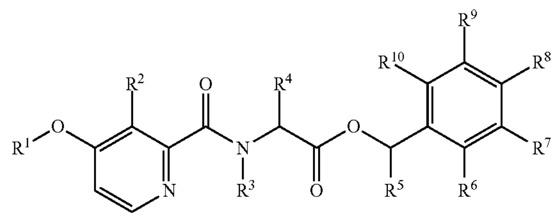

wherein, $R^1$ is $C_1$-$C_6$alkyl or $C_1$-$C_6$haloalkyl;

$R^2$ is hydroxy, $C_2$-$C_6$acyloxy, $C_2$-$C_6$haloacyloxy, $C_1$-$C_6$alkoxy$C_1$-$C_6$alkoxy, $C_1$-$C_6$haloalkoxy$C_1$-$C_6$alkoxy, $C_1$-$C_6$alkoxy$C_1$-$C_6$haloalkoxy, $C_2$-$C_6$acyloxy$C_1$-$C_6$alkoxy, $C_2$-$C_6$haloacyloxy$C_1$-$C_6$alkoxy or $C_2$-$C_6$acyloxy$C_1$-$C_6$haloalkoxy;

$R^3$ is hydrogen, $C_1$-$C_6$alkoxy or $C_3$-$C_8$cycloalkyl;

$R^4$ and $R^5$ are each independently $C_1$-$C_6$alkyl, $C_3$-$C_8$cycloalkyl or $C_1$-$C_6$haloalkyl;

$R^6$, $R^9$ and $R_{10}$ are each independently hydrogen, halogen or $C_1$-$C_6$alkyl;

$R^7$ and $R^8$ are each independently hydrogen, aryl, heteroaryl, aryl$C_1$-$C_3$alkyl, heteroaryl$C_1$-$C_3$alkyl, aryloxy, or heteroaryloxy, wherein the heteroaryl moiety is a 5- or 6-membered aromatic ring which comprises 1, 2, 3 or 4 heteroatoms individually selected from N, O and S, and wherein the aryl and heteroaryl moieties are each optionally substituted by 1, 2 or 3 substituents, which may be the same or different, selected from $R^{11}$;

$R^{11}$ is halogen, cyano, $C_1$-$C_6$alkyl, $C_3$-$C_6$cycloalkyl, $C_1$-$C_6$haloalkyl, $C_1$-$C_6$alkoxy, $C_1$-$C_6$alkoxy$C_1$-$C_6$alkyl, $C_1$-$C_4$haloalkoxy or $C_1$-$C_6$alkylcarbonyl;

or a salt or an N-oxide thereof.

2. The compound according to claim 1, wherein $R^1$ is methyl.

3. The compound according to claim 1, wherein $R^2$ is hydroxy, acetoxy or 2-methyl-propanoyloxymethoxy.

4. The compound according to claim 1, wherein $R^3$ is hydrogen.

5. The compound according to claim 1, wherein $R^4$ and $R^5$ are each independently $C_1$-$C_3$alkyl or $C_1$-$C_3$haloalkyl.

6. The compound according to claim 1, wherein $R^6$, $R^9$ and $R^{10}$ are each independently hydrogen or fluoro.

7. The compound according to claim 1, wherein $R^7$ and $R^8$ are each independently hydrogen, aryl, heteroaryl, aryl$C_1$-$C_3$alkyl, heteroaryl$C_1$-$C_3$alkyl, aryloxy or heteroaryloxy, wherein the heteroaryl moiety is a 5- or 6-membered aromatic ring which comprises 1 or 2 heteroatoms individually selected from N, O and S, and wherein the aryl and heteroaryl moieties are each optionally substituted by 1, 2 or 3 substituents, which may be the same or different, selected from $R^{11}$.

8. The compound according to claim 1, wherein $R^7$ is hydrogen and $R^8$ is aryl, heteroaryl, arylC$_1$-C$_3$alkyl or aryloxy, wherein the heteroaryl moiety is a 5- or 6-membered aromatic ring which comprises 1 or 2 heteroatoms individually selected from N and S, and wherein the aryl and heteroaryl moieties are each optionally substituted by 1, 2 or 3 substituents, which may be the same or different, selected from $R^{11}$.

9. The compound according to claim 1, wherein $R^7$ is hydrogen; and
   $R^8$ is phenyl optionally substituted by 1 or 2 substituents, which may be the same or different, selected from $R^{11}$, wherein $R^{11}$ is halogen, C$_1$-C$_3$alkyl, C$_1$-C$_3$alkoxyC$_1$-C$_2$alkyl or C$_1$-C$_3$haloalkyl, or
   naphthyl, or
   pyridyl optionally substituted by 1 or 2 substituents, which may be the same or different, selected from $R^{11}$, wherein $R^{11}$ is halogen, C$_1$-C$_3$alkyl or C$_1$-C$_3$haloalkyl, or
   pyrazolyl optionally substituted by 1, 2 or 3 substituents, which may be the same or different, selected from $R^{11}$, wherein $R^{11}$ is C$_1$-C$_3$alkyl, or
   thiazolyl optionally substituted by 1 or 2 substituents, which may be the same or different, selected from $R^{11}$, wherein $R^{11}$ is C$_1$-C$_3$alkyl, or
   phenoxy optionally substituted by 1 or 2 substituents, which may be the same or different, selected from $R^{11}$, wherein $R^{11}$ is halogen or C$_1$-C$_3$alkyl, or
   benzyl, wherein the phenyl ring of the benzyl moiety is optionally substituted by a single $R^{11}$, wherein $R^{11}$ is halogen.

10. The compound according to claim 1, wherein $R^7$ is phenyl, benzyl or phenoxy, wherein the phenyl moiety of each $R^7$ group is optionally substituted by 1 or 2 substituents, which may be the same or different, selected from $R^{11}$; and
    $R^8$ is hydrogen.

11. The compound according to claim 1, wherein $R^{11}$ is chloro, fluoro, bromo, methyl, ethyl, isopropyl, trifluoromethyl, difluoromethyl, trichloromethyl, dichloromethyl, methoxy, ethoxy, isopropoxy, isopropoxymethyl or t-butoxymethyl.

12. An agrochemical composition comprising a fungicidally effective amount of a compound of formula (I) according to claim 1.

13. The composition according to claim 12, further comprising at least one additional active ingredient and/or an agrochemically-acceptable diluent or carrier.

14. A method of controlling or preventing infestation of plants by phytopathogenic fungi, comprising: applying a fungicidally effective amount of a compound of formula (I) according to claim 1 to the plants, to parts thereof or the locus thereof.

15. A compound selected from the group consisting of:

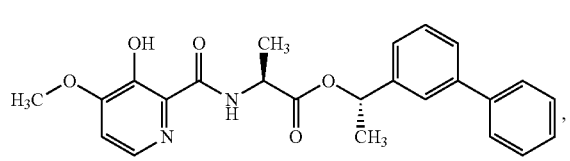

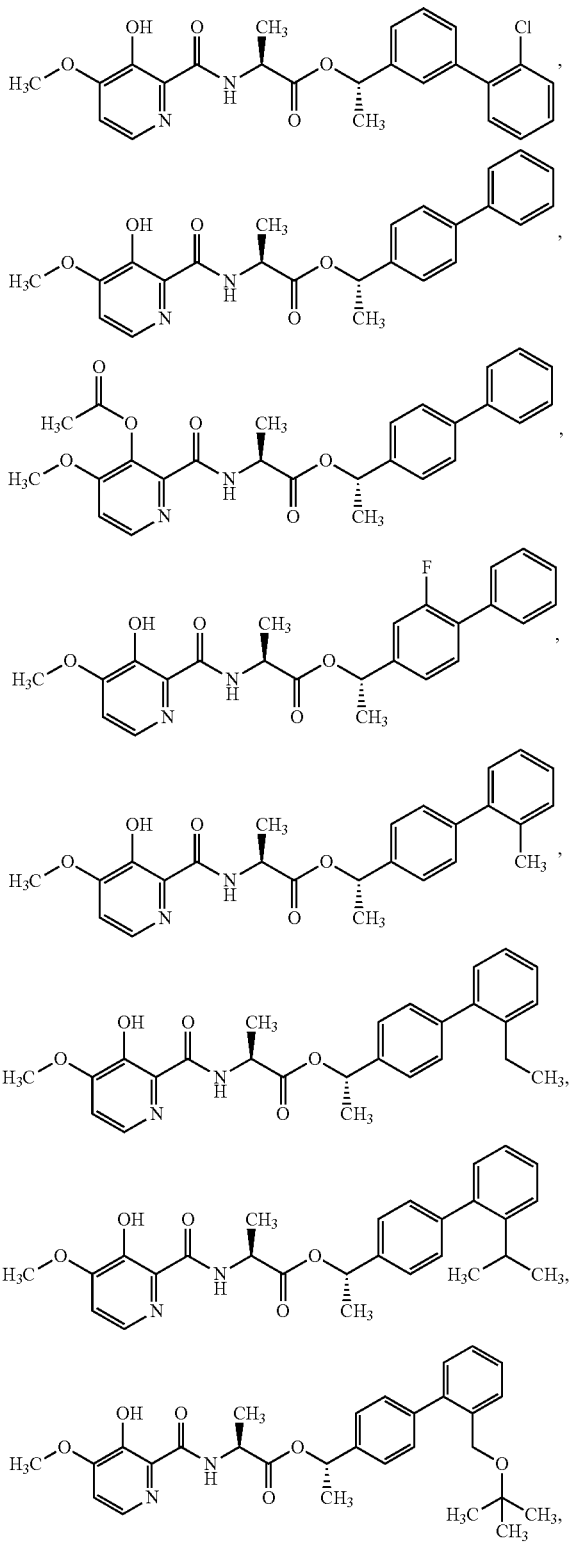

75
-continued
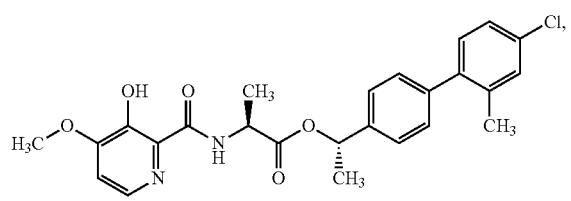
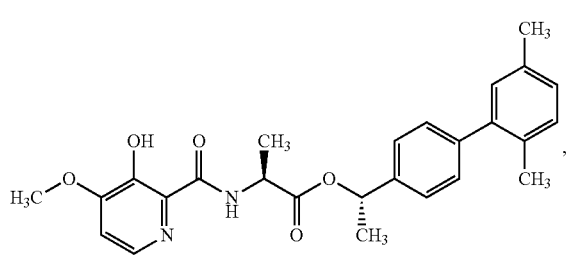
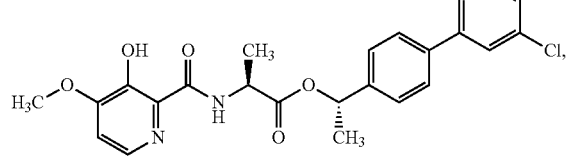
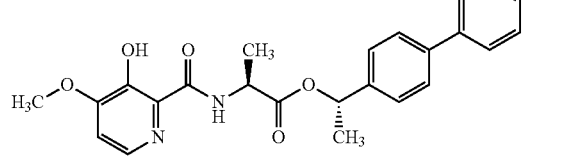
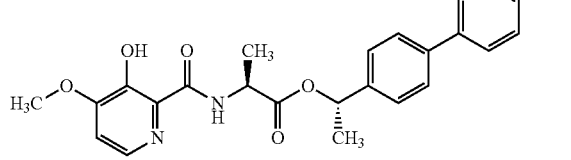
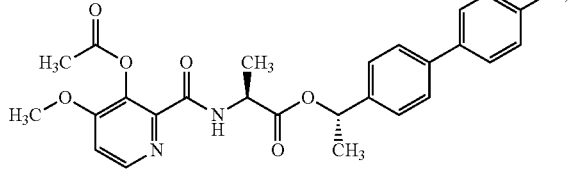
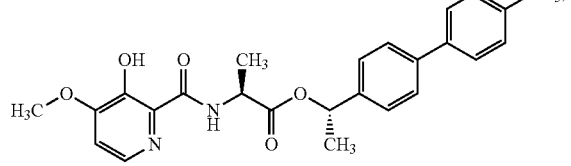
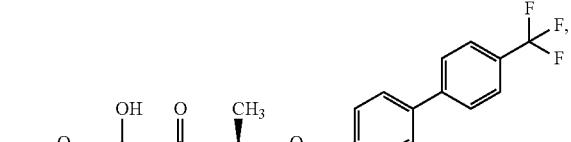
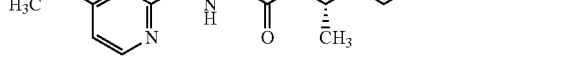
76
-continued
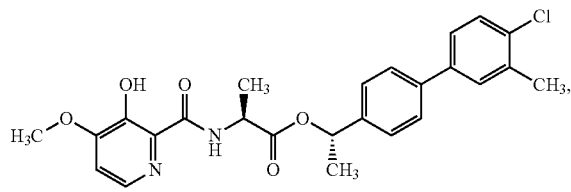
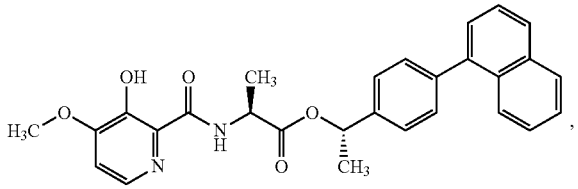
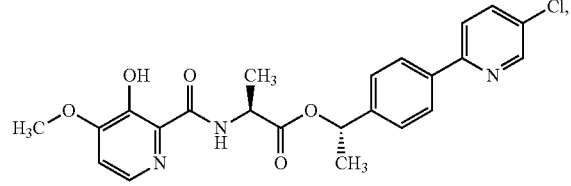
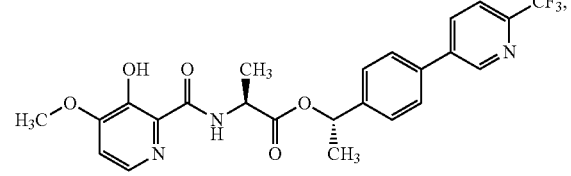
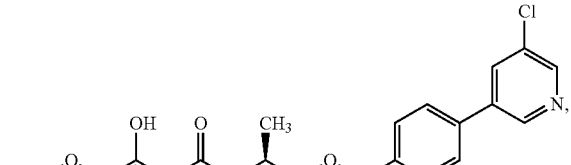
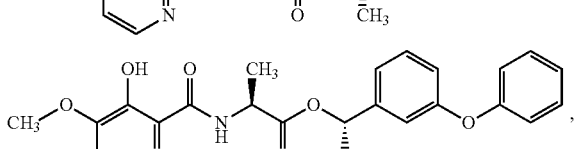
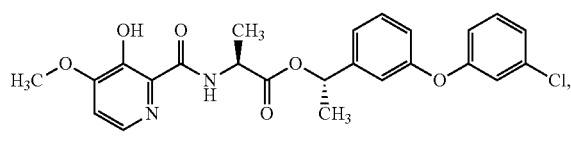
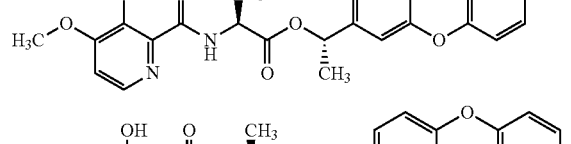
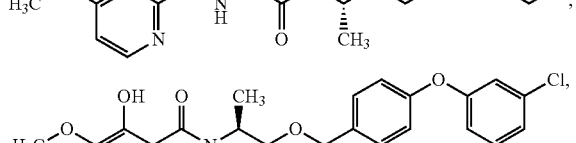
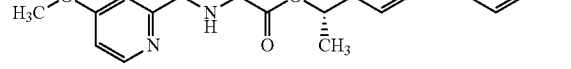

77
-continued
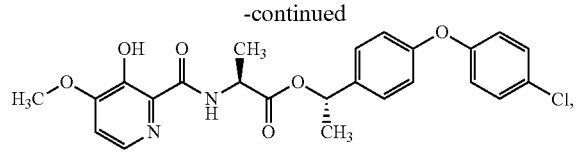
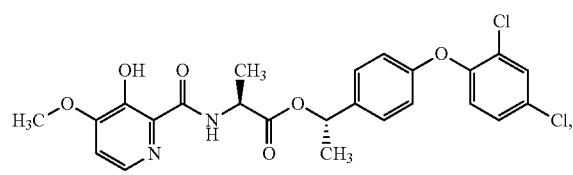
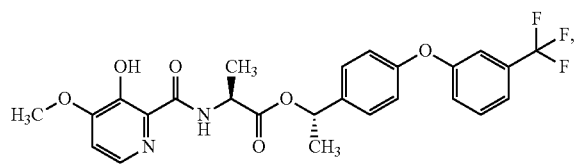
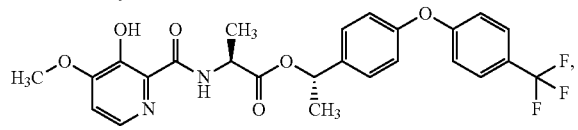
78
-continued
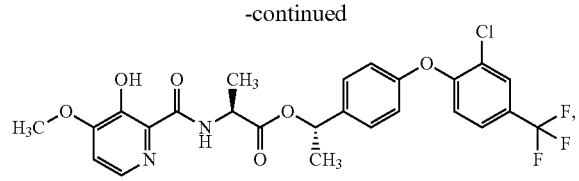
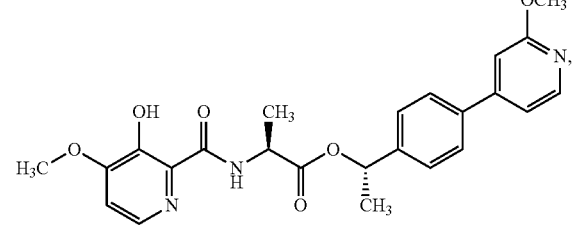
and
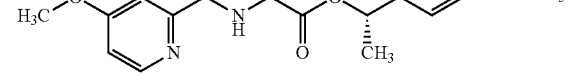
* * * * *